(12) United States Patent
Johnson et al.

(10) Patent No.: US 10,363,123 B2
(45) Date of Patent: Jul. 30, 2019

(54) DISTAL PROTECTION SYSTEMS AND METHODS WITH PRESSURE AND ULTRASOUND FEATURES

(71) Applicant: VOLCANO CORPORATION, San Diego, CA (US)

(72) Inventors: Eric Johnson, San Diego, CA (US); Gilbert Laroya, San Diego, CA (US); Paul Do, San Diego, CA (US); Jeremy Stigall, Carlsbad, CA (US); Joseph Lauinger, San Diego, CA (US)

(73) Assignee: VOLCANO CORPORATION, San Diego, CA (US)

( * ) Notice: Subject to any disclaimer, the term of this patent is extended or adjusted under 35 U.S.C. 154(b) by 267 days.

(21) Appl. No.: 14/773,574

(22) PCT Filed: Mar. 17, 2014

(86) PCT No.: PCT/US2014/030240
§ 371 (c)(1),
(2) Date: Sep. 8, 2015

(87) PCT Pub. No.: WO2014/145469
PCT Pub. Date: Sep. 18, 2014

(65) Prior Publication Data
US 2017/0165046 A1    Jun. 15, 2017

Related U.S. Application Data

(60) Provisional application No. 61/794,222, filed on Mar. 15, 2013.

(51) Int. Cl.
*A61F 2/01* (2006.01)
*A61B 8/12* (2006.01)
(Continued)

(52) U.S. Cl.
CPC .............. *A61F 2/013* (2013.01); *A61B 5/026* (2013.01); *A61B 8/06* (2013.01); *A61B 8/12* (2013.01);
(Continued)

(58) Field of Classification Search
CPC ........................................................ A61F 2/013
See application file for complete search history.

(56) References Cited

U.S. PATENT DOCUMENTS

| 4,265,251 A | 5/1981 | Tickner |
| 4,276,885 A | 7/1981 | Tickner et al. |

(Continued)

FOREIGN PATENT DOCUMENTS

| WO | 2006062725 A1 | 6/2006 |
| WO | 2006074163 A2 | 7/2006 |

(Continued)

OTHER PUBLICATIONS

Kahraman, H. et al, "The Diameters of the Aorta and Its Major Branches in Patients with Isolated Coronary Artery Ectasia", Tex Hears Inst. J. 2006; 33:463-8.

*Primary Examiner* — Rochelle D Turchen

(57) ABSTRACT

Embodiments of the invention relate generally to devices and methods for providing filtration of debris within a body lumen. More particularly, embodiments of the invention related to devices and methods for providing distal protection to a medical procedure by filtration of debris generated by the medical procedure using filters having a frame with a slidable crossover point.

16 Claims, 39 Drawing Sheets

(51) Int. Cl.
  *A61F 2/00* (2006.01)
  *A61L 31/18* (2006.01)
  *A61B 34/20* (2016.01)
  *A61B 90/00* (2016.01)
  *A61B 5/026* (2006.01)
  *A61B 8/06* (2006.01)
  *A61B 8/00* (2006.01)
  *A61M 25/00* (2006.01)
  *A61M 25/01* (2006.01)
  *A61M 25/09* (2006.01)

(52) U.S. Cl.
  CPC .............. *A61B 8/445* (2013.01); *A61B 34/20* (2016.02); *A61B 90/39* (2016.02); *A61F 2/0077* (2013.01); *A61F 2/01* (2013.01); *A61L 31/18* (2013.01); *A61B 2090/3784* (2016.02); *A61B 2090/3966* (2016.02); *A61F 2002/0081* (2013.01); *A61F 2002/011* (2013.01); *A61F 2250/0096* (2013.01); *A61F 2250/0098* (2013.01); *A61M 2025/0002* (2013.01); *A61M 2025/0183* (2013.01); *A61M 2025/09183* (2013.01)

(56) References Cited

U.S. PATENT DOCUMENTS

| | | |
|---|---|---|
| 4,401,124 A | 8/1983 | Guess et al. |
| 4,442,843 A | 4/1984 | Rasor et al. |
| 4,466,442 A | 8/1984 | Hilmann et al. |
| 4,572,203 A | 2/1986 | Feinstein |
| 4,718,433 A | 1/1988 | Feinstein |
| 5,081,997 A | 1/1992 | Bosley et al. |
| 5,201,314 A | 4/1993 | Bosley et al. |
| 5,289,831 A | 3/1994 | Bosley |
| 5,327,891 A | 7/1994 | Rammler |
| 5,921,933 A | 7/1999 | Sarkis et al. |
| 6,106,476 A | 8/2000 | Corl et al. |
| 6,440,077 B1 | 8/2002 | June et al. |
| 6,485,502 B2 | 11/2002 | Michael et al. |
| 6,645,152 B1 | 11/2003 | Jung et al. |
| 6,780,157 B2 | 8/2004 | Stephens et al. |
| 7,789,892 B2 | 9/2010 | Johnson et al. |
| 7,806,906 B2 | 10/2010 | Michael |
| 8,277,386 B2 | 10/2012 | Ahmed et al. |
| 2004/0230119 A1 | 11/2004 | Brustad et al. |
| 2004/0243175 A1 | 12/2004 | Don Michael |
| 2006/0100658 A1 | 5/2006 | Obana et al. |
| 2008/0004687 A1 | 1/2008 | Barbut et al. |
| 2008/0147111 A1 | 6/2008 | Johnson et al. |
| 2009/0024153 A1 | 1/2009 | Don Michael |
| 2010/0130963 A1 | 5/2010 | Ebert et al. |
| 2012/0172915 A1 | 7/2012 | Fifer et al. |

FOREIGN PATENT DOCUMENTS

| | | |
|---|---|---|
| WO | 2006084156 A2 | 8/2006 |
| WO | 2009029861 A1 | 3/2009 |
| WO | 2011112463 A1 | 9/2011 |

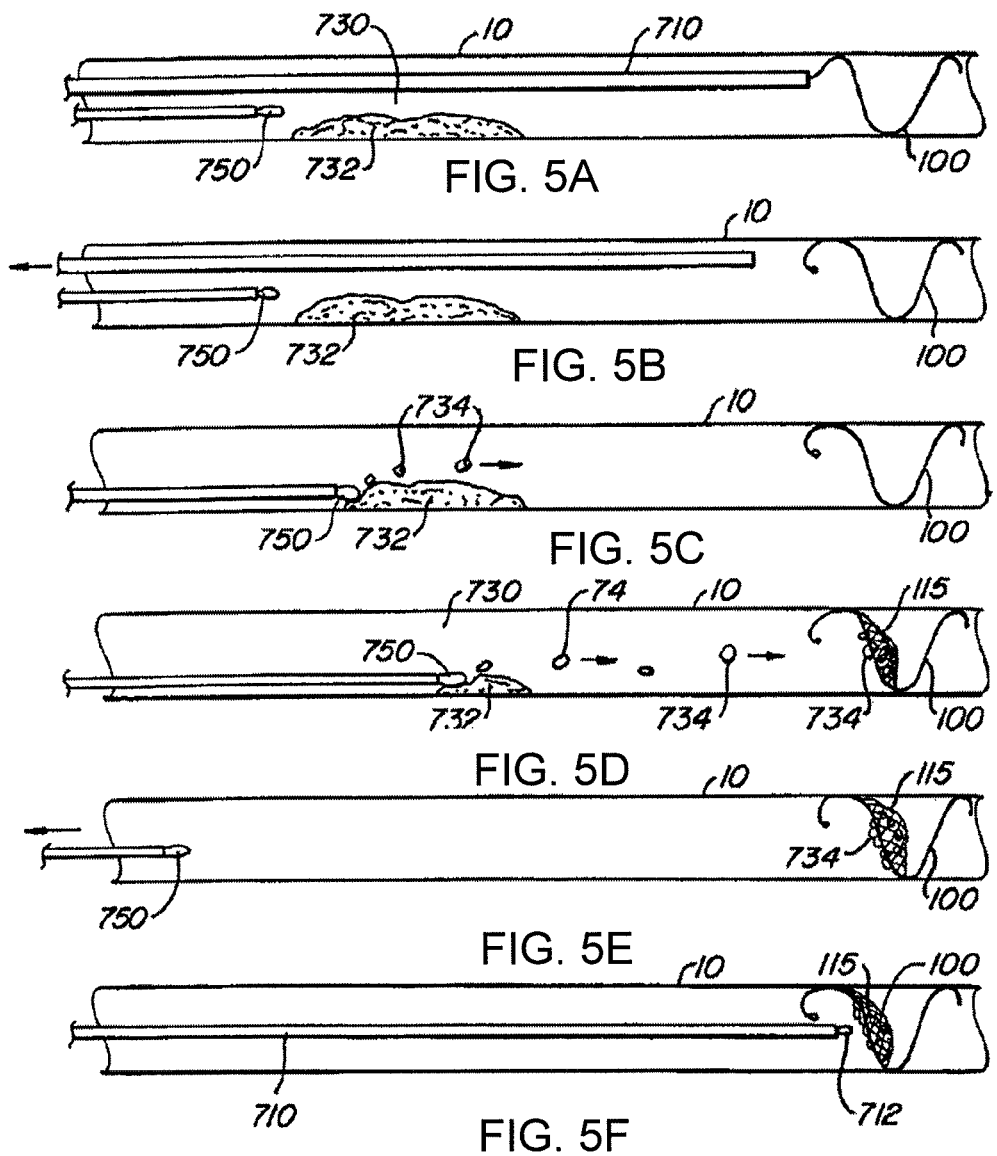

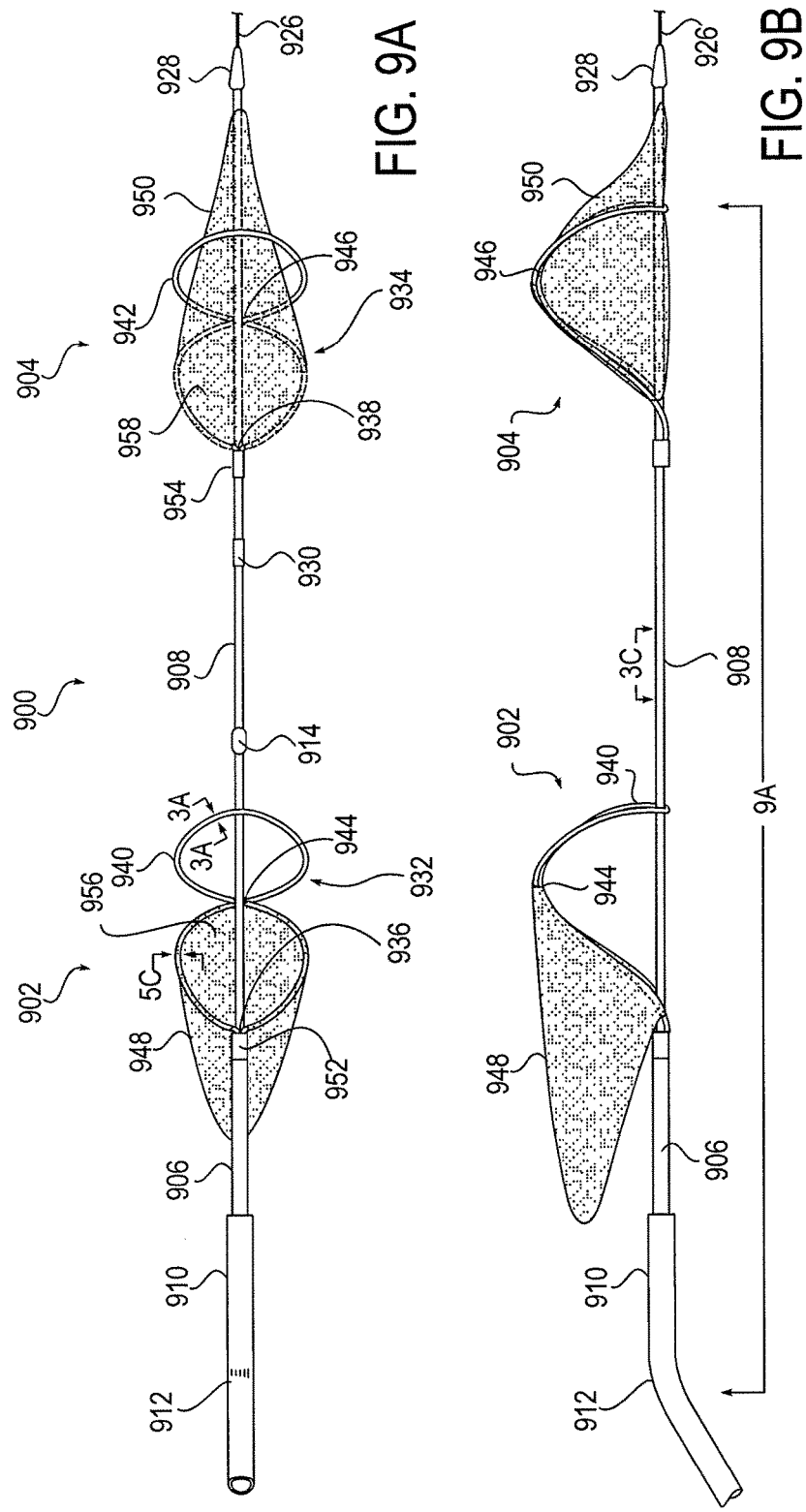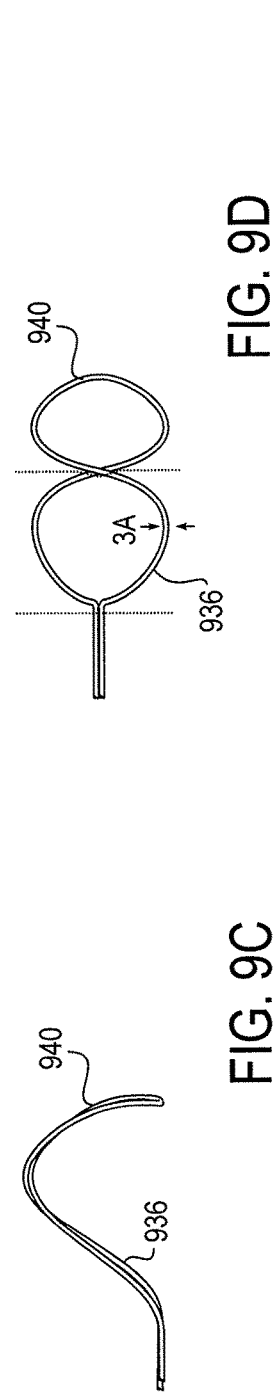

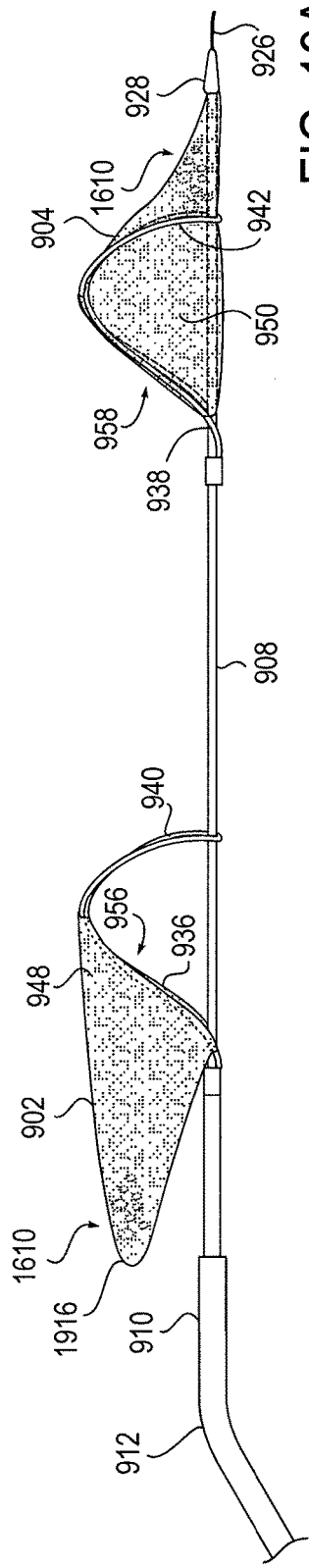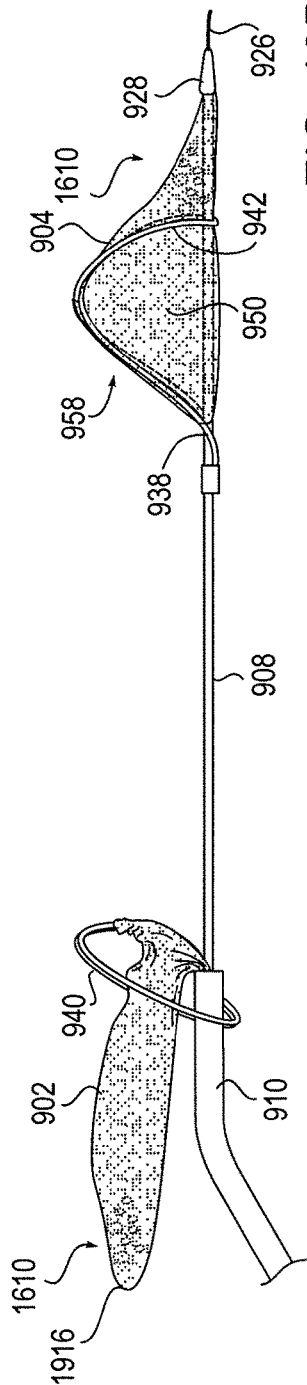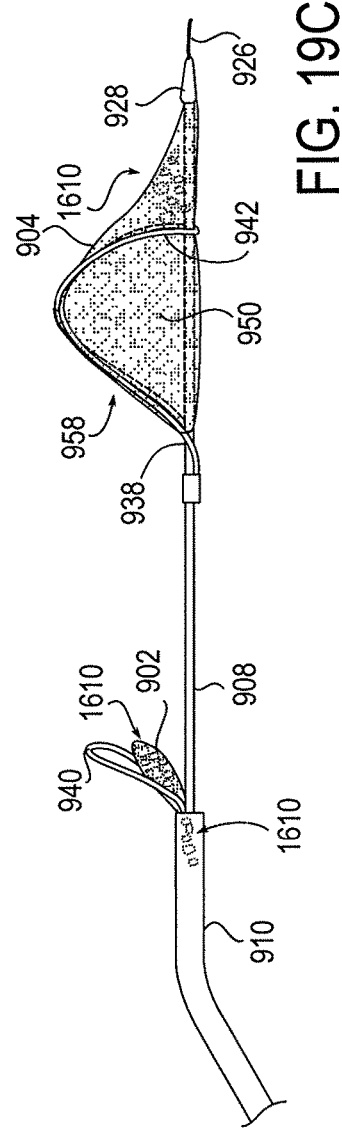

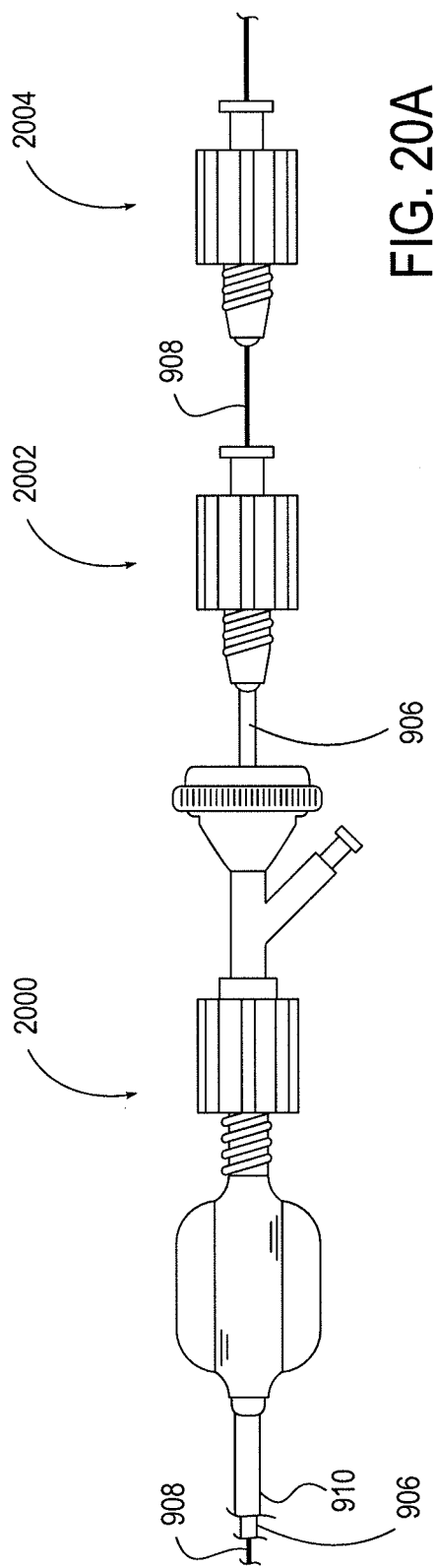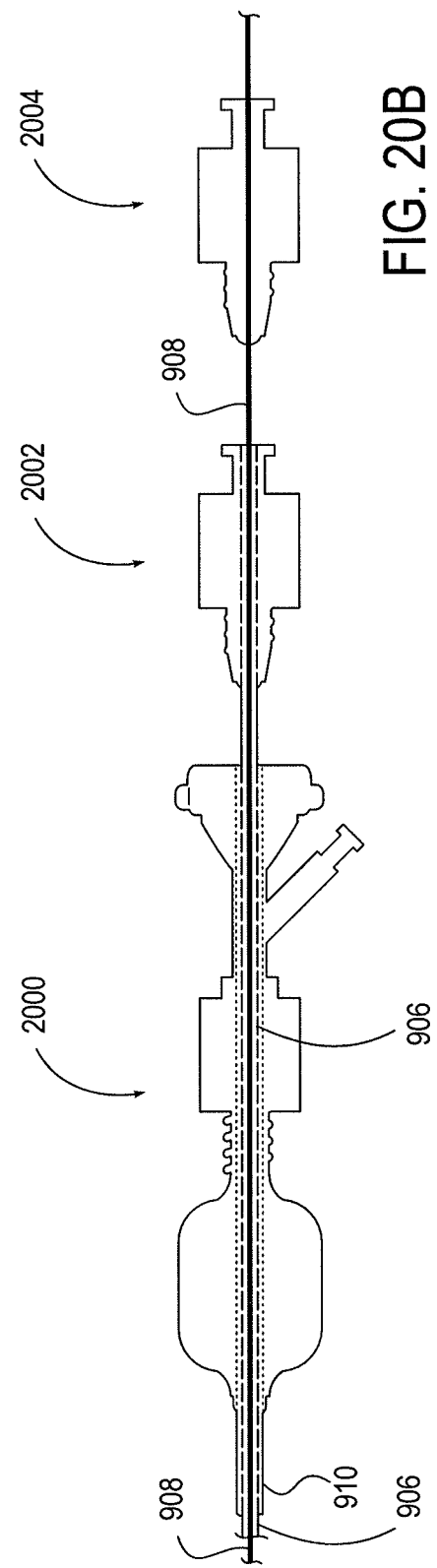
FIG. 20A
FIG. 20B

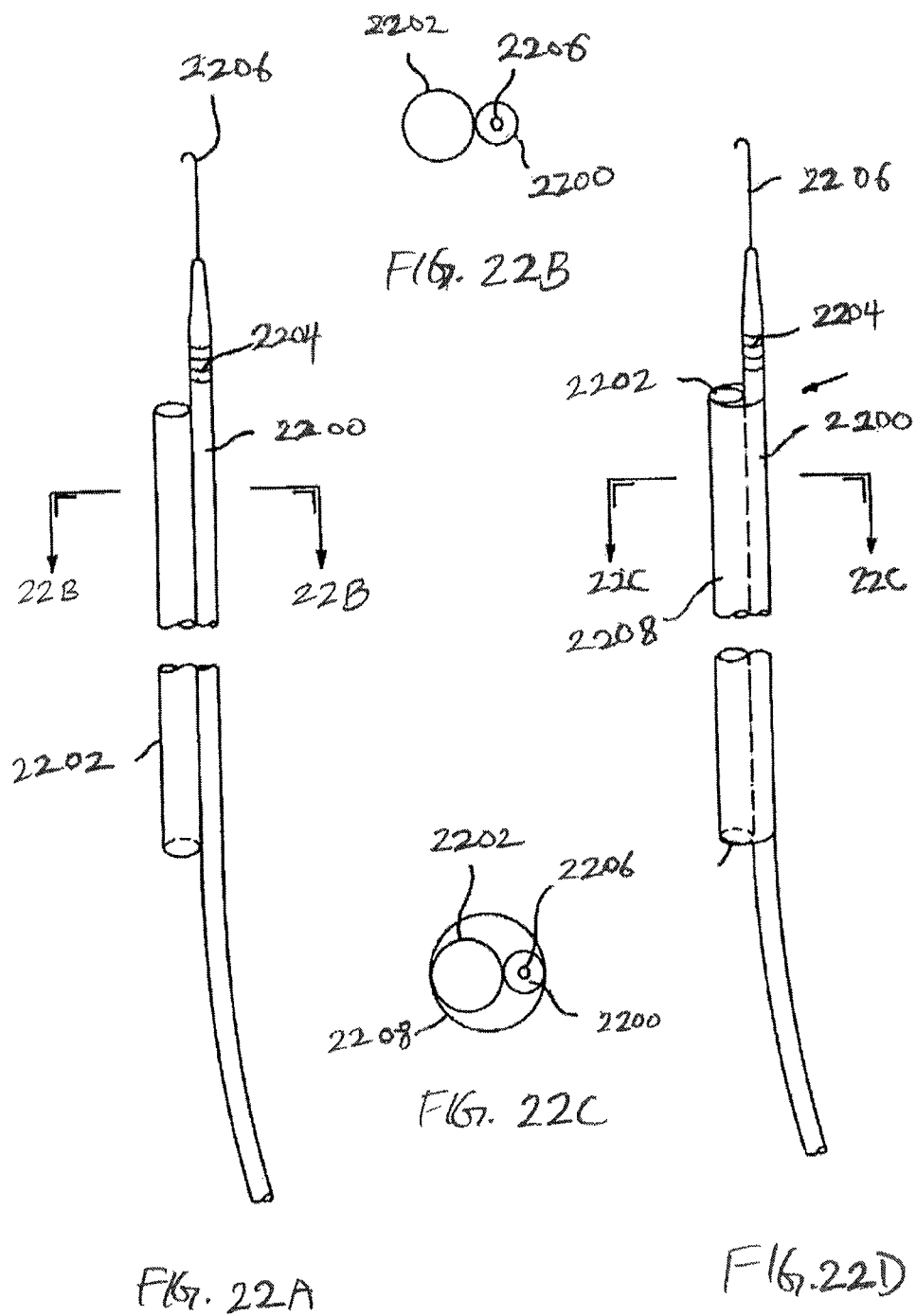

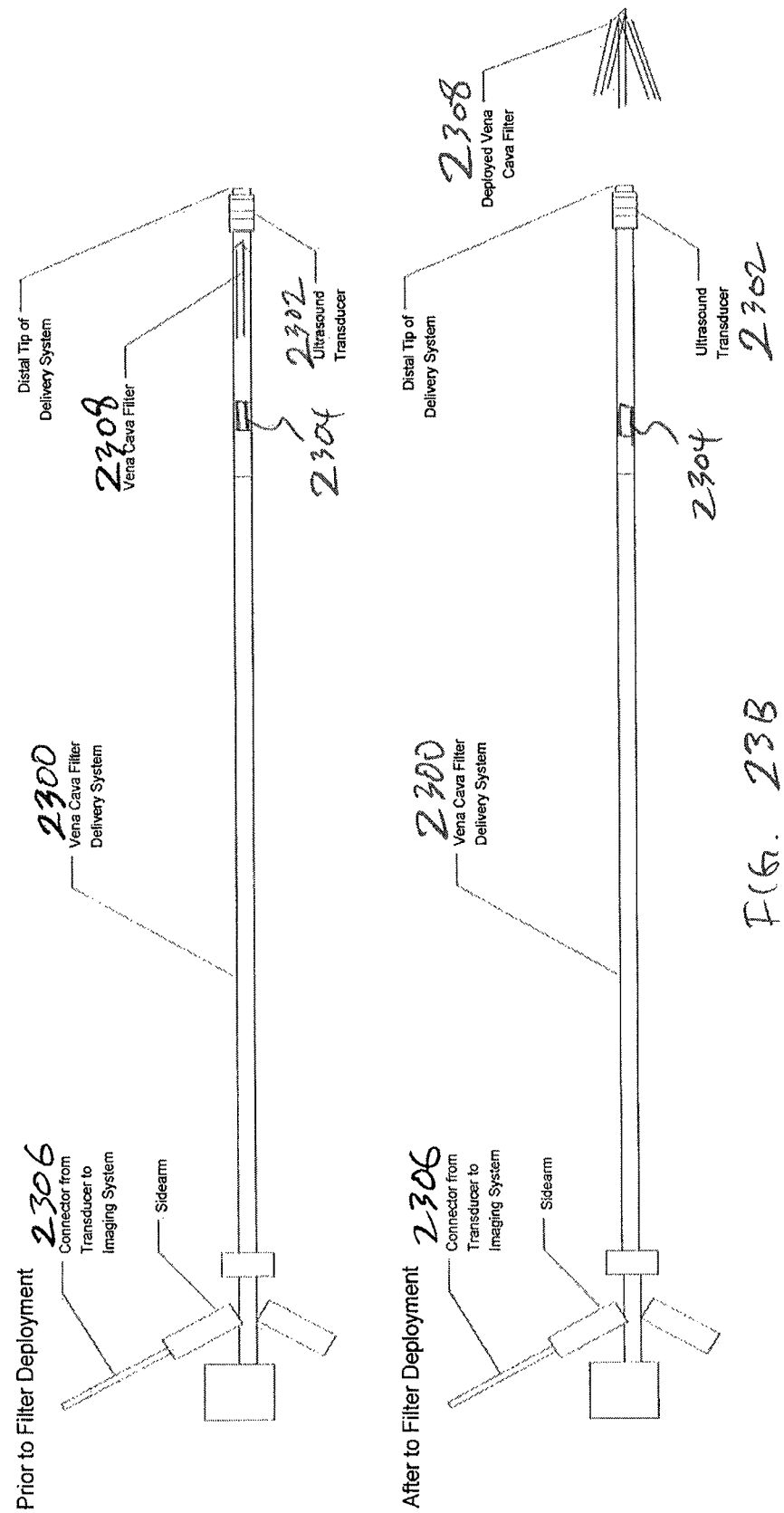

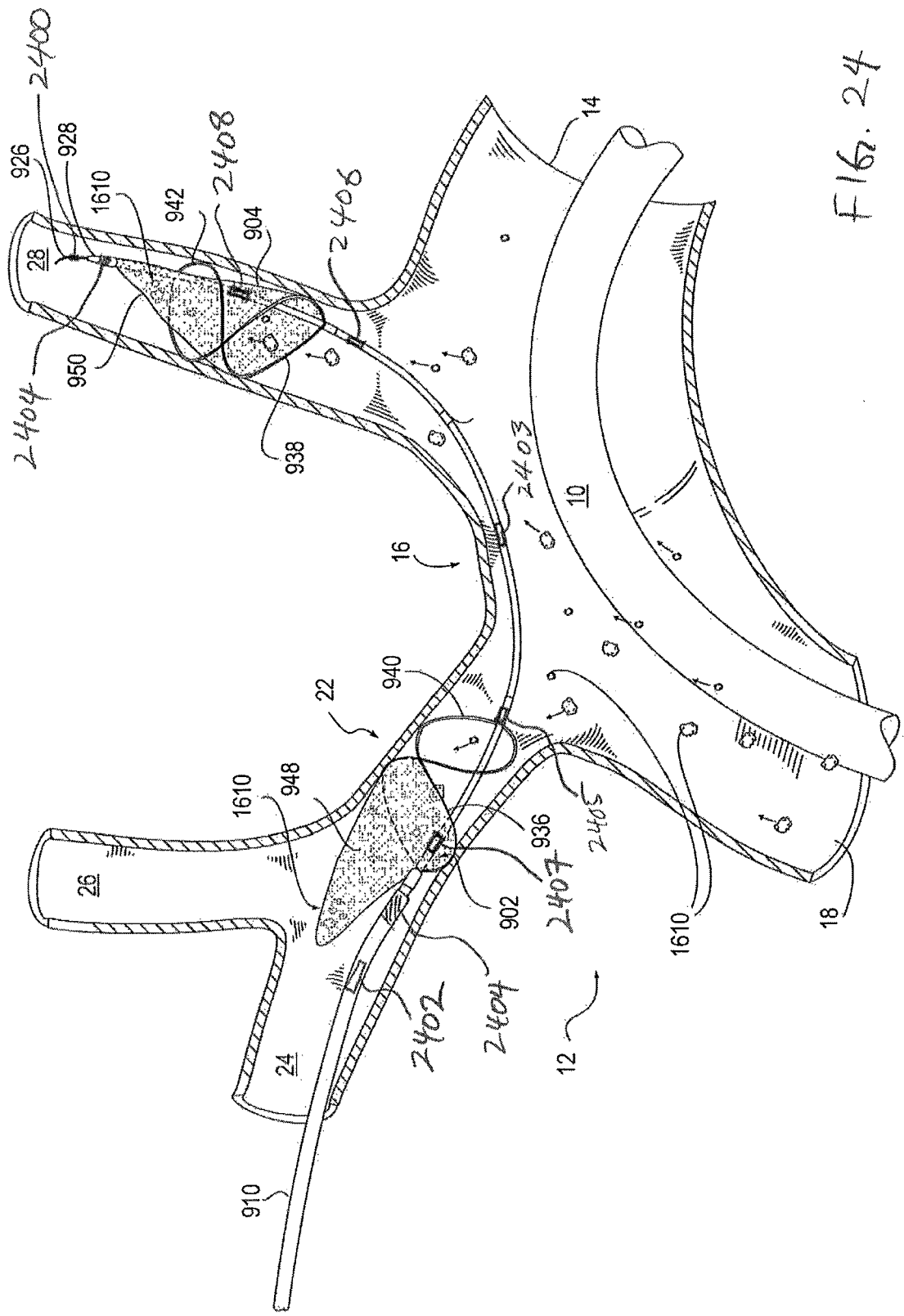

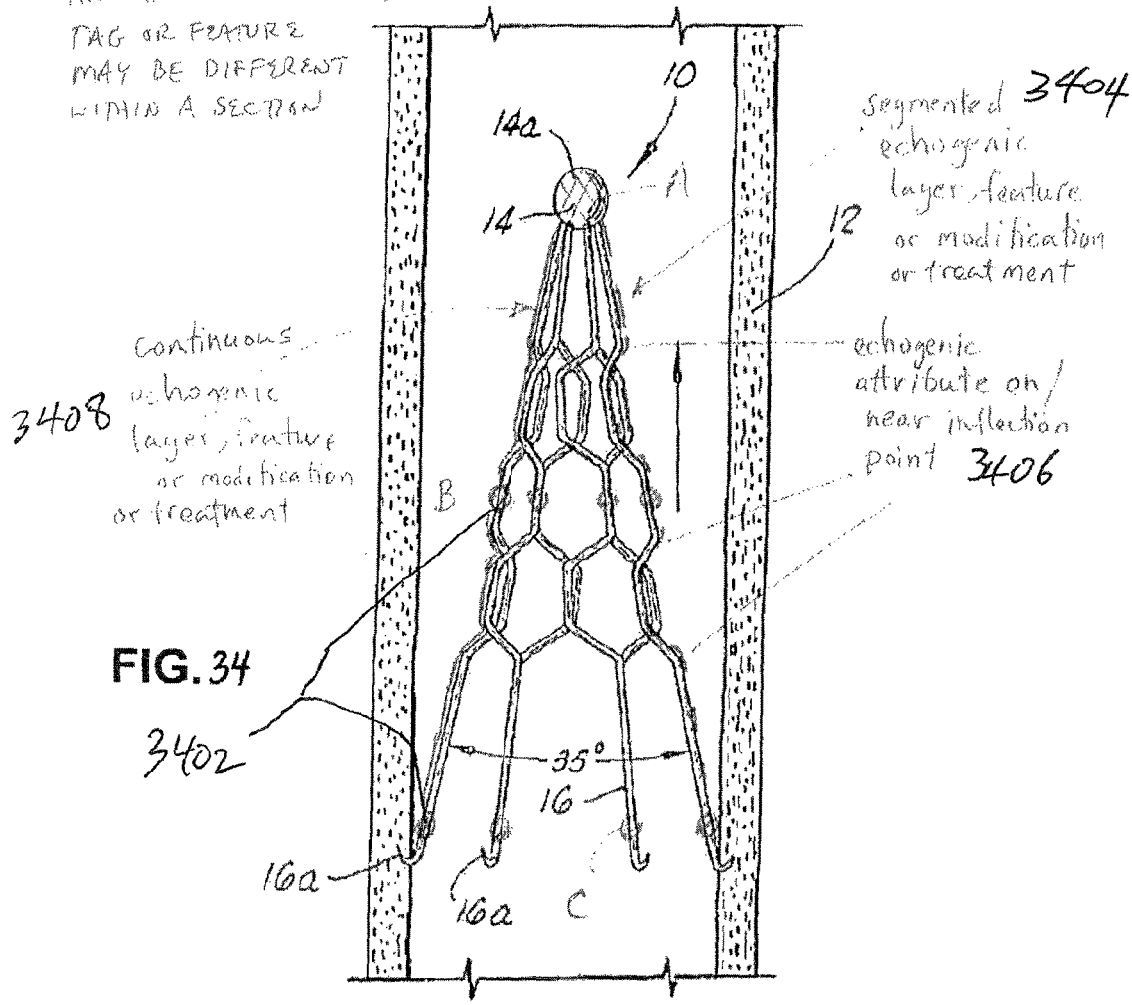

DISTAL PROTECTION SYSTEMS AND METHODS WITH PRESSURE AND ULTRASOUND FEATURES

CROSS REFERENCE TO RELATED APPLICATIONS

This application claims priority to PCT Application No. PCT/US2014/030240 filed on Mar. 17, 2014, which claims priority to U.S. provisional application No. 61/794,222 filed Mar. 15, 2013, which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference. This application is related to U.S. application Ser. No. 11/325,247, now issued as U.S. Pat. No. 7,789,892, which is hereby incorporated by reference in its entirety.

FIELD

Embodiments of the invention relate generally to devices and methods for providing filtration of debris within a body lumen. More particularly, embodiments of the invention related to devices and methods for providing distal protection to a medical procedure by filtration of debris generated by the medical procedure.

BACKGROUND

Embolic protection is utilized throughout the vasculature to prevent the potentially fatal passage of embolic material, calcium deposits, and other debris in the bloodstream to smaller vessels where it can obstruct blood flow. The dislodgement of embolic material, calcium deposits, and other debris is often associated with procedures which open blood vessels to restore natural blood flow such as stenting, angioplasty, arthrectomy, valve replacement or repair, endarterectomy or thrombectomy. Used as an adjunct to these procedures, embolic protection devices trap debris and provide a means for removal from the body.

For example, in a percutaneous aortic valve replacement procedure as shown in FIGS. 1A and 1B, a valve delivery catheter 10 can be inserted through the lumen 13 of the aorta 12, via the descending aorta 14, the aortic arch 16, the ascending aorta 18, and to the native aortic valve 20 of the heart. During insertion through the aortic arch 16, the valve delivery catheter 10 has a tendency to make contact with the upper portion 32 of the aortic arch 16 as it traverses the bend between the descending aorta 14 and ascending aorta 18. During the aortic valve replacement procedure, embolic debris, calcium deposits and other debris can be generated and/or loosened from the native valve leaflets. This debris can travel through arteries branching off the aorta 12, such as the brachiocephalic trunk 22, which splits into the right subclavian artery 24 and the right common carotid artery 26, the left common carotid artery 28, and the left subclavian artery 30. Debris that passes into the right common carotid 26 and left common carotid artery 28 can travel to and get lodged within vessels supplying blood to the brain, potentially causing a stroke.

Accordingly, it would be desirable to provide a system and method for providing embolic protection to the right common carotid artery and the left common carotid artery in order to reduce complications, such as stroke, that may occur during a variety of medical procedures as described herein.

SUMMARY OF THE DISCLOSURE

The present invention relates generally to devices and methods for providing filtration of debris within a body lumen. More particularly, embodiments of the invention related to devices and methods for providing distal protection to a medical procedure by filtration of debris generated by the medical procedure.

Variations and modifications of the devices and methods disclosed herein will be readily apparent to persons skilled in the art. As such, it should be understood that the foregoing summary, detailed description and the accompanying illustrations, are made for purposes of clarity and understanding, and are not intended to limit the scope of the invention, which is defined by the claims appended hereto. Any feature described in any one embodiment described herein can be combined with any other feature of any of the other embodiment whether preferred or not.

In some embodiments, a system for providing embolic protection is provided. The system includes a first sheath having a proximal end, a distal end and a lumen, the lumen configured to receive a guidewire; a first distal protection filter attached to a distal portion of the first sheath, the first distal protection filter comprising a self-expanding frame with a slidable crossover point that defines a proximal loop and a distal loop, and a filter element attached to one of the proximal loop or distal loop of the self-expanding frame of the first distal protection filter, wherein the crossover point is proximate to the filter element; a second sheath having a proximal end, a distal end and a lumen, the second sheath disposed over the first sheath, wherein the distal end of the second sheath is located proximally the first distal protection filter; a second distal protection filter attached to a distal portion of the second sheath, the second distal protection filter comprising a self-expanding frame with a slidable crossover point that defines a proximal loop and a distal loop, and a filter element attached to the proximal loop of the self-expanding frame of the second distal protection filter, wherein the crossover point is proximal to the filter element; and an outer sheath disposed over both the first sheath and the second sheath.

In some embodiments, the filter element of the second distal protection filter has a mouth and an apex, wherein the mouth of the filter element is attached to the proximal loop and the apex is unattached to the sheath.

In some embodiments, the first sheath includes a stop portion proximal the first distal protection filter, wherein the stop portion is configured to stop advancement of the second sheath proximal to the stop portion.

In some embodiments, in a stowed configuration within the outer sheath, the filter element of the first distal protection filter has a mouth facing the second distal protection filter and the filter element of the second distal protection filter has a mouth facing the first distal protection filter.

In some embodiments, the distance between the first distal protection filter and the second distal protection filter is adjustable. In some embodiments, the position of the first sheath and the position of the second sheath are independently lockable, allowing one of the first sheath and the second sheath to be locked in position while the position of the other sheath adjusted.

In some embodiments, the self-expanding frame of the first distal protection filter includes at least one anchor element. In some embodiments, the self-expanding frame of the second distal protection filter includes at least one anchor element. In some embodiments, the at least one anchor element of the first distal protection filter is configured to partially penetrate through the vessel wall. In some embodiments, the first sheath includes at least one anchor proximal the first distal protection filter. In some embodiments, the at least one anchor is located on a side of the first sheath opposite the crossover point of the first distal protection filter. In some embodiments, the at least one anchor is configured to be located within the aortic arch of a patient when the first distal protection filter is deployed from the outer sheath. In some embodiments, the at least one anchor of the first sheath is configured to partially penetrate through the vessel wall.

In some embodiments, the filter elements of both the first distal protection filter and the second distal protection filter include a plurality of pores with a diameter of less than about 200 microns. In some embodiments, the pores of the filter elements of both the first distal protection filter and the second distal protection filter are distributed more densely in the peripheral portion of the filter elements. In some embodiments, the pores of the filter elements of both the first distal protection filter and the second distal protection filter are larger in the peripheral portion of the filter elements than in the central portion of the filter elements. In some embodiments, the pores of the filter elements are oblong shaped. In some embodiments, the filter elements comprise filter membranes with laser drilled holes.

In some embodiments, the filter elements comprise polymer fibers that are selected from the group consisting of electrospun fibers, knitted fibers, braided fibers, and woven fibers. In some embodiments, the filter elements are made from a polymer selected from the group consisting of polyurethane, polyethylene, and nylon.

In some embodiments, the filter elements of both the first distal protection filter and the second distal protection filter have an open area between about 25 to 75 percent.

In some embodiments, the outer sheath is 9 Fr or less.

In some embodiments, the self-expanding frames of both the first distal protection filter and the second distal protection filter include a radiopaque marker. In some embodiments, the radiopaque marker is a radiopaque coil of wire wrapped around a superelastic core.

In some embodiments, the distal loops of both the first distal protection filter and the second distal protection filter are unattached to either the first sheath or second sheath.

In some embodiments, the outer sheath includes a curved distal portion with a curvature between about 15 to 45 degrees.

In some embodiments, the first distal protection filter and second distal protection filter are coated with a drug. In some embodiments, the drug is heparin.

In some embodiments, the proximal loop of the first distal protection filter is attached to first sheath, and the proximal loop of the second distal protection filter is attached to the second sheath. In some embodiments, the distal loop of the first distal protection filter is attached to first sheath, and the proximal loop of the second distal protection filter is attached to the second sheath.

In some embodiments, the self-expanding frame comprises a single wire element shaped in a figure eight configuration.

In some embodiments, the system further includes a hub, the hub having a first hub portion that is engaged with the proximal portion of the first sheath, a second hub portion that is engaged with the proximal portion of the second sheath, and a third hub portion that is engaged with the proximal portion of the outer sheath, wherein the hub allows the first sheath, the second sheath, and the outer sheath to be independently manipulated. In some embodiments, the third hub portion is removable and configured to allow the outer sheath to be swapped for another sheath. In some embodiments, each of the first hub portion, the second hub portion and the third hub portion are configured to receive the guidewire.

In some embodiments, the system further includes a deflection mechanism attached to the first sheath at a location between the first distal protection filter and the second distal protection filter after deployment of both distal protection filters. In some embodiments, the deflection mechanism is an inflatable balloon. In some embodiments, the deflection mechanism is a flat shield.

In some embodiments, a method of providing embolic protection to at least two blood vessels is provided. The method includes advancing a first distal protection filter to a first location in a first blood vessel, wherein the first distal protection filter includes a first self-expanding frame, and a first filter element having a mouth and an apex with the mouth attached to the first self-expanding frame; deploying the first distal protection filter at the first location; manipulating a second distal protection filter to a second location in a second blood vessel, wherein the second distal protection filter includes a second self-expanding frame and a second filter element having a mouth and an apex with the mouth attached to the second self-expanding frame; deploying the second distal protection filter at the second location; performing a procedure in a portion of the vasculature that releases or generates particulate debris; and capturing the particulate debris with one or more of the first distal protection filter and the second distal protection filter.

In some embodiments, the method further includes advancing an outer sheath over the mouth of the second filter element to close the mouth of the second filter element before advancing the outer sheath over the apex of the second filter element; and advancing the outer sheath over the mouth of the first filter element to close the mouth of the first filter element before advancing the outer sheath over the apex of the first filter element.

In some embodiments, the first distal protection filter is deployed in the left common carotid artery and the second distal protection filter is deployed in the brachiocephalic trunk.

In some embodiments, the method further includes adjusting the length between the first distal protection filter and the second distal protection filter. In some embodiments, the length is adjusted by fixing the location of the first distal protection filter, and then manipulating the position of the second distal protection filter.

In some embodiments, the method further includes conforming a sheath attached to the first distal protection filter to the upper surface of the aortic arch between the left common carotid artery and the brachiocephalic trunk. In some embodiments, the method further includes conforming a sheath attached to the first distal protection filter along the inner wall of the aortic arch from the outer radius of the aortic arch proximate the left common carotid artery to the inner radius of the aortic arch and to the outer radius of the aortic arch proximate the brachiocephalic trunk.

In some embodiments, the first self-expanding frame includes a slidable crossover point that defines a proximal loop and a distal loop, and wherein the second self-expanding frame includes a slidable crossover point that defines a proximal loop and a distal loop with the mouth of the second filter element attached to the proximal loop of the second self-expanding frame.

In some embodiments, the apex of the second filter element is unattached to the second self-expanding frame.

In some embodiments, the distal loop of first self-expanding frame moves proximally as the mouth of the first filter element is closed such that the distal loop of the first self-expanding frame is proximal the crossover point of the first self-expanding frame during a part of the mouth closure process. In some embodiments, the distal loop of second self-expanding frame moves proximally as the mouth of the second filter element is closed such that the distal loop of the second self-expanding frame is proximal the crossover point of the second self-expanding frame during a part of the mouth closure process.

In some embodiments, the apex of the second filter is unattached to a structure on which the second distal protection filter is attached.

In some embodiments, the method further includes aspirating the debris trapped in either the first distal protection filter or the second distal protection filter.

In some embodiments, the method further includes deploying a deflection mechanism between the first distal protection filter and the second distal protection filter.

In some embodiments, manipulating a second distal protection filter to a second location includes withdrawing the second distal protection filter to the second location. In some embodiments, manipulating a second distal protection filter to a second location includes advancing the second distal protection filter to the second location.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 9A and 9B illustrate an embodiment of a filtering device with two distal protection filters;

FIGS. 9C and 9D illustrate an embodiment of the frame of a distal protection filter;

FIGS. 19A-19F illustrate an embodiment of a method of capturing the distal protection filters using an outer sheath; and FIGS. 20A and 20B illustrate an embodiment of the various hubs used to manipulate the various components of the filtering device.

FIGS. 22A-22D illustrate two embodiments of an intravascular ultrasound catheter joined together in parallel with a catheter.

FIGS. 23A and 23B illustrate an embodiment of a filter delivery system where the pressure sensor and/or IVUS transducer are integrated into a delivery catheter, a retrieval catheter or a device itself.

FIG. 24 illustrates an embodiment of a distal protection filtering device having one or more ultrasound transducers and one or more pressure sensors.

FIG. 34 is a view of an exemplary filter illustrating various alternative aspects of providing a filter with improved echogenic characteristics.

DETAILED DESCRIPTION

Figure 1A:
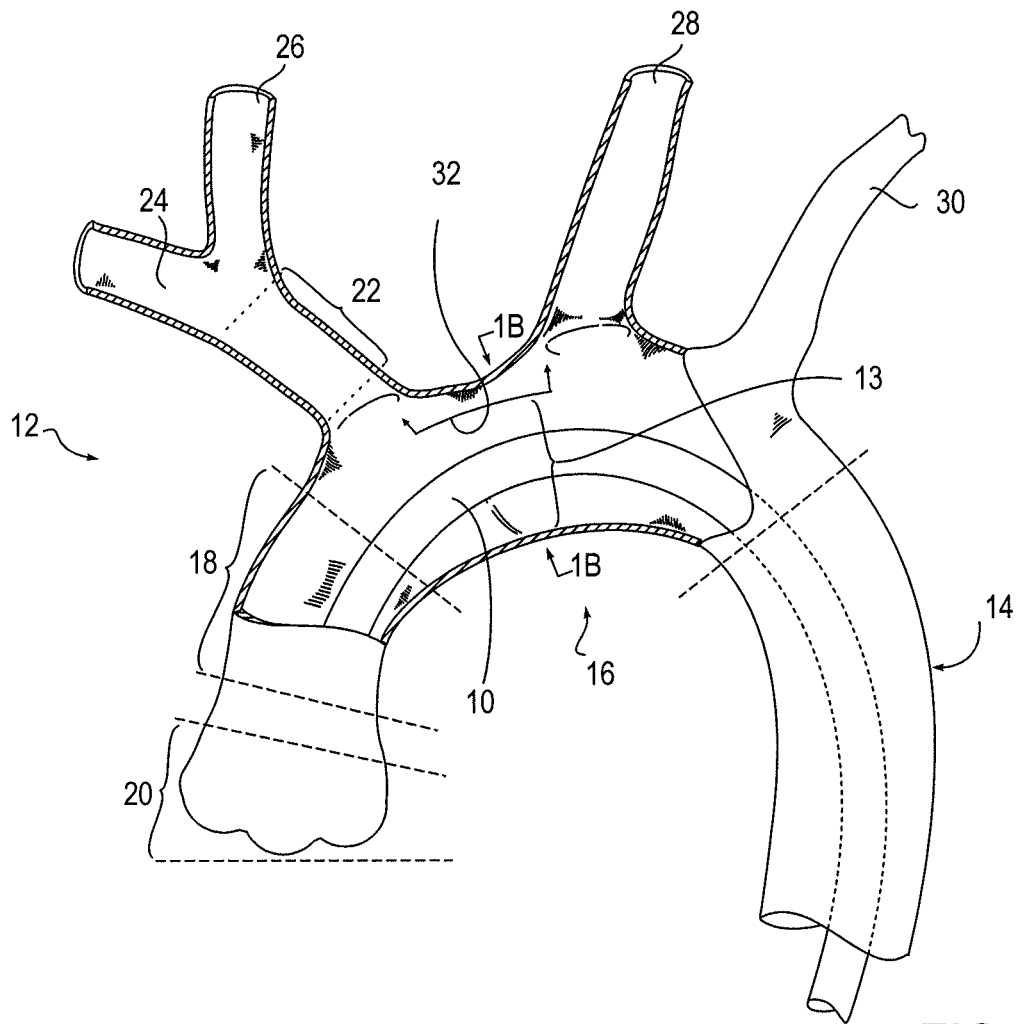
FIG. 1A is a side view of the aorta and its branch arteries with a catheter inserted within the aortic lumen.
Figure 1B:
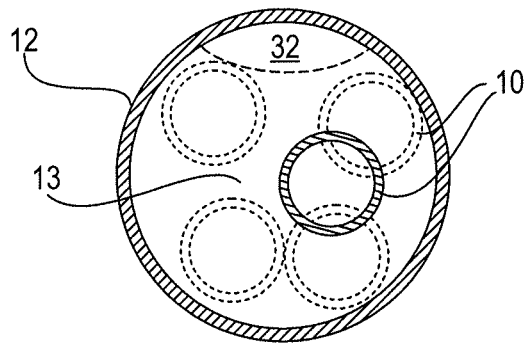
FIG. 1B is a cross-section view of the aorta with a catheter within the aortic lumen.
Figure 2A:
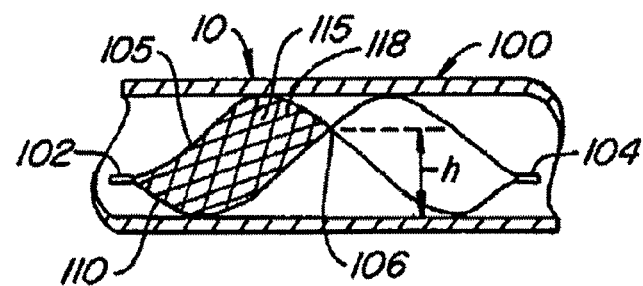
FIGS. 2A-2C illustrate the response of an embodiment of a filtering device to changes in lumen size.

FIG. 2A illustrates an embodiment of a filtering device 100 of the present invention positioned within a lumen 10. The lumen 10 is cut away to show the position of filter 100 deployed into within a lumen and in contact with the lumen wall. The filter 100 includes a first elongate member 105 and a second elongate member 110. In some embodiments, the two elongate members can be opposing helical spirals. The elongate members are joined to form ends 102, 104. The elongate members cross but are not joined to one another at crossover 106, which can be slidable. In one embodiment, the elongate members have first and second sections. First sections extend between the end 102 and the crossover 106 and the second sections extend from the crossover 106 to the second end 104. While some embodiments contact the lumen in different ways, the illustrated embodiment has the ends 102, 104 against one side of the lumen interior wall while the crossover 106 contacts the other side of the lumen interior wall with the elongate bodies in constant or nearly constant apposition along the lumen interior wall between the ends 102, 104. In some embodiments, the diameter of the elongate members can be about 0.003, 0.004, 0.005, 0.006, 0.007, 0.008, 0.009, or 0.010 inches. Using a smaller diameter wire allows the filter to have a lower collapsed profile. In some embodiments, the filters can be collapsed into a 10 Fr, 9 Fr, 8 Fr, 7 Fr, 6 Fr, or 5 Fr or smaller delivery catheter. In some embodiments, the elongate members can be made from a flexible, biocompatible, fatigue-resistant material such as but not limited to nickel-titanium alloys, stainless steel, cobalt chrome, other shape memory alloys, other metal alloys, and various polymers such as PEEK, PTFE, and the like.

Figure 2B:
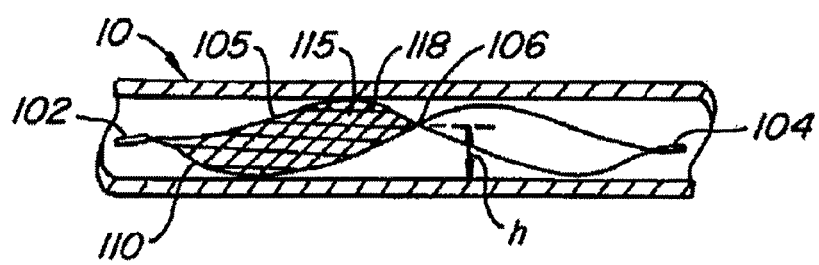
Figure 2C:
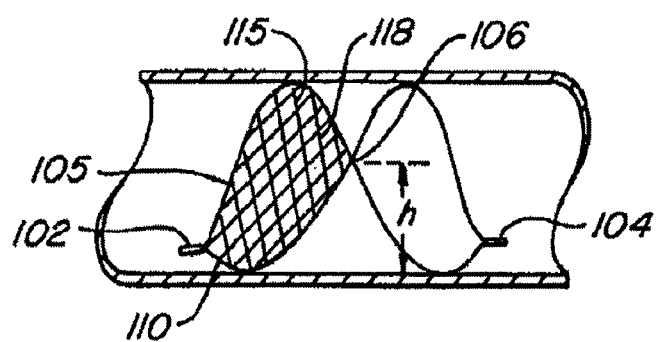

FIGS. 2B and 2C illustrate how the elongate support structure elements of embodiments of the present invention are configured to collapse and expand with natural vessel movements while maintaining constant apposition with the vessel wall. FIGS. 2A, 2B and 2C also illustrate how devices according to embodiments of the present invention are both radially and axially elastic. In response to vessel size changes, ends 102, 104 move out as the vessel size decreases (FIG. 2B) and then move in as the vessel size increases (FIG. 2C). In addition, the device height "h" (measured from the lumen wall in contact with ends 102, 104 to crossover) also changes. Device height "h" changes in direct relation to changes in vessel diameter (i.e., vessel diameter increases will increase device height "h"). As such, device height ("h") in FIG. 2C is greater than device height ("h") in FIG. 2A which is in turn greater than the device height ("h") in FIG. 2B.

FIGS. 2A, 2B and 2C also illustrate how a single sized device can be used to accommodate three different lumen diameters. FIG. 2C illustrates a large lumen, FIG. 2A a medium sized lumen and FIG. 2B a small sized lumen. As these figures make clear, one device can adapt to cover a range of vessel sizes, thereby forming a better seal and providing good wall apposition over a wide range of vessel diameters. Also illustrated is the static or nearly static filter capacity of the material capture structure 115 in some embodiments. In these embodiments, in each different vessel size, the material capture structure 115, the filaments 118 and filter cell 119 maintain the same or nearly the same shape and orientation within the support frame formed by the elongate bodies. These figures also illustrate the dynamic shape changing aspect of the device that may also be used to accommodate and conform to vessel irregularities, tortuosity, flares and tapers and while remaining in apposition to the wall. Because each elongate body may move with a high degree of independence with respect to the other, the loops or support frames formed by the elongate bodies can also independently match the shape/diameter of the lumen section in which it is placed.

For example, a single sized device can be used in a variety of vessels, such as the brachiocephalic trunk and left common carotid artery. The brachiocephalic trunk generally has a diameter between about 6 mm to about 20 mm or larger, and usually between about 8 mm to about 12 mm, or about 8 to 10 mm. The left common carotid artery generally has a diameter between about 5 mm to about 11 mm, and usually between about 6 mm to about 10 mm, or about 7 to 8 mm. Examples of the diameters of the aorta and its major branch arteries are disclosed in Kahraman et al., *The Diameters of the Aorta and Its Major Branches in Patients with Isolated Coronary Artery Ectasia*, Tex Heart Inst J 2006; 33:463-8, which is hereby incorporated by reference in its entirety. In some embodiments, a filter device with a nominal diameter size of about 6 mm, 9 mm, 12 mm, 15 mm, or 18 mm or between about 6 to 18 mm, can be used in the brachiocephalic trunk or left common carotid artery. Because these filter devices cover a dynamic range of sizes, as illustrated in FIGS. 2A-2C, a single filter can used to cover all or a wide range, such as the lower half/upper half or the lower third/middle third/upper third, of typical brachiocephalic trunk and/or left common carotid artery sizes. In some embodiments, the filter devices placed in the brachiocephalic trunk and left common carotid artery can have the same nominal diameter size, while in other embodiments the filter device placed in the left common carotid artery can be smaller than the filter device placed in the brachiocephalic trunk.

Figure 3A:
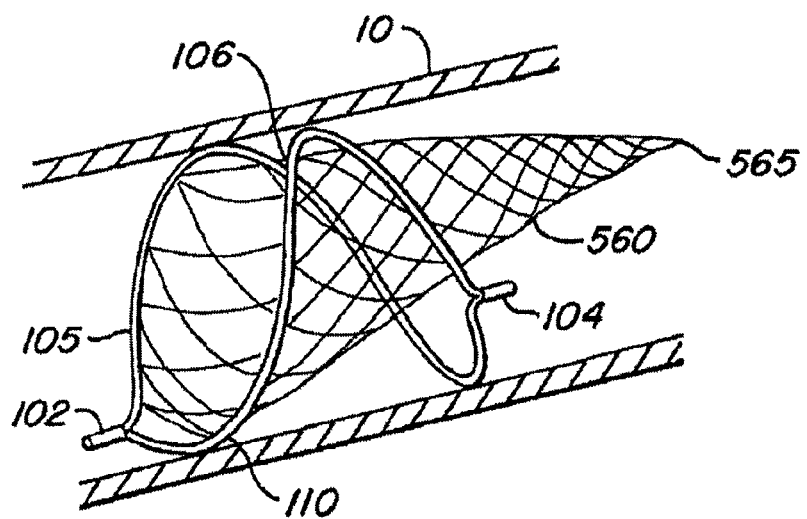
FIGS. 3A and 3B illustrate embodiments of the distal protection filter with a filter element having an attached apex and an unattached apex.
Figure 3B:
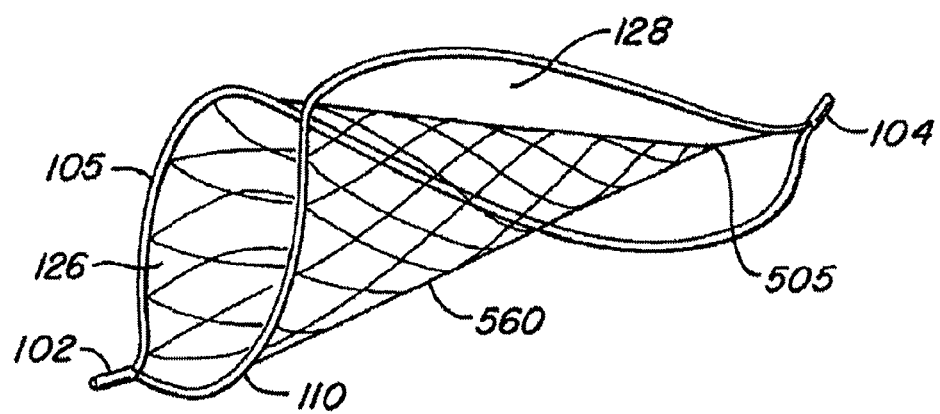

FIGS. 3A-4F illustrate the use of nets or other web structures within the filtering device. The various net structure embodiments described herein are used as material capture structures within filter device embodiments of the present invention. Each of these alternative is illustrated in a support structure similar to that of device 100 in FIG. 2A and elsewhere. When deployed within the lumen 10, the material capture structure 560 has a defined shape such as a cone with a discrete apex 565 (FIG. 3A). In this embodiment, the net structure is long enough to contact the sidewall of the lumen 10 when deployed in the lumen 10. Alternatively, the apex 565 may be attached to the end 104 to keep the net 560 in the lumen flow path and out of contact with the lumen sidewall (FIG. 3B).

Figure 4A:
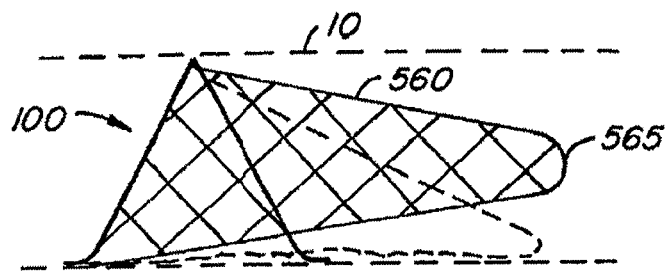
FIGS. 4A-4F illustrate various alternative filtering structures.
Figure 4B:
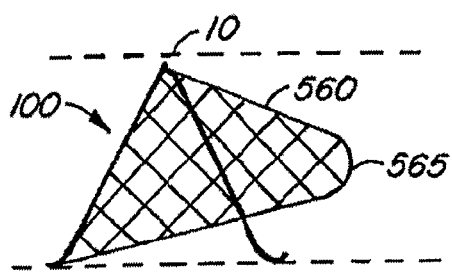
Figure 4C:
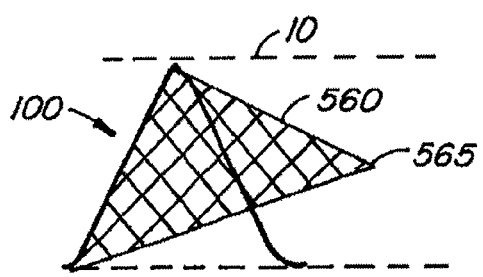
Figure 4D:
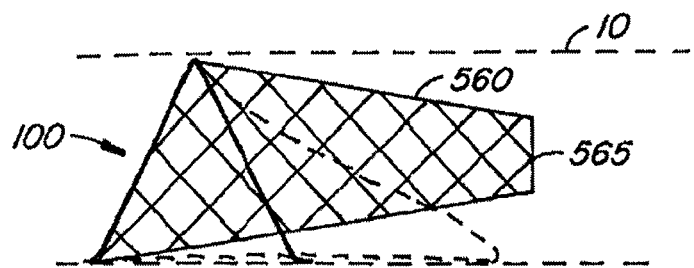
Figure 4E:
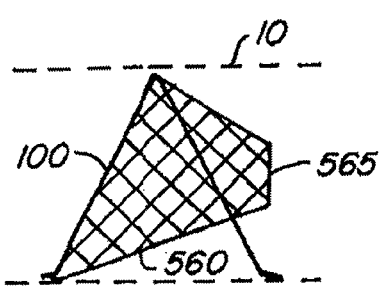
Figure 4F:
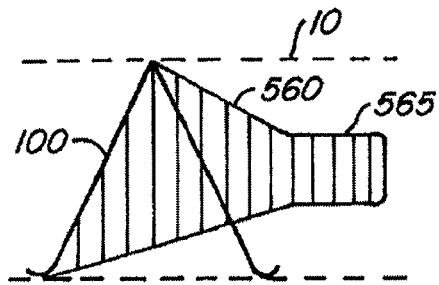

In some embodiments, the apex can be attached to the delivery device, such as the sheath, tube or wire of the delivery device. In other embodiments, the apex can be free, or in other words is unattached to the sheath, tube or wire of the delivery device or the frame of the filter. In some embodiments with a proximal filter and a distal filter, as illustrated in FIG. 9A, the apex of the proximal filter can remain free while the apex of the distal filter can be attached to the delivery device. In some embodiments, the apex of the distal filter can also remain unattached to the sheath. Allowing the apex of the proximal filter to remain free allows a sheath 10 to be advanced first over the mouth of the filter to close the filter before being advanced over the rest of the filter. This prevents or reduces the extrusion of trapped debris within the filter during the recovery of the proximal filter. The net 565 may also have a rounded apex 565 (FIG. 4A) or a truncated cone (flat bottom) (FIG. 4D) or a reservoir apex. Alternatively, the net 560 may a discrete apex 565 so short that it will not contact the lumen sidewall when deployed (FIG. 4B). The short net may also have a rounded apex 565 (FIG. 4B), a flat apex (FIG. 4E) or a sharp apex (FIG. 4C). In addition, the net 560 may have a compound apex 565 (FIG. 4F).

Figure 5G:
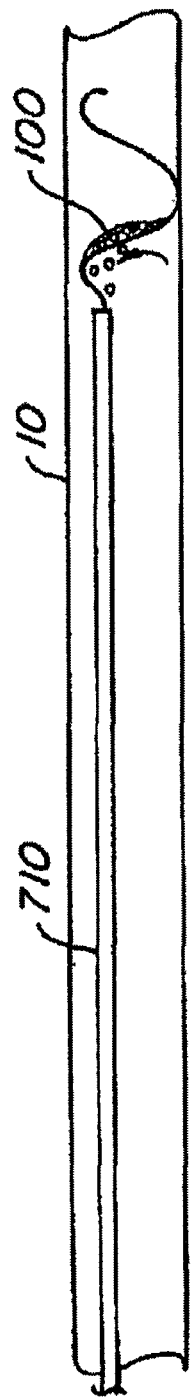
FIGS. 5A-8F illustrate several exemplary methods of using a filtering device.
Figure 5H:
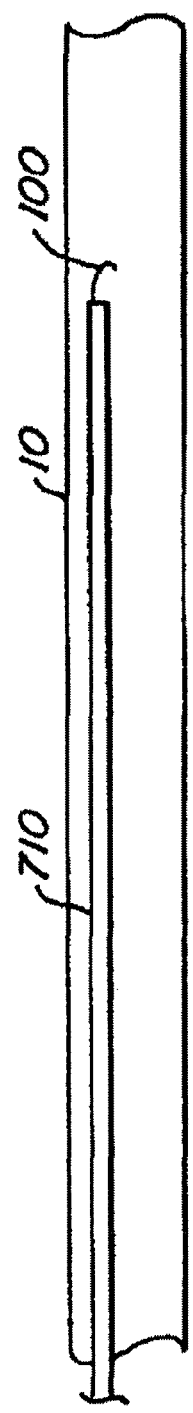
Figure 5I:

Embodiments of filter devices of the present invention may be used in methods of providing distal protection in procedures such as, for example, thrombectomy, arthrectomy, stenting, angioplasty, valve repair or replacement, stent grafting and other procedures taking place in the heart or circulatory system. It is to be appreciated that embodiments of filter devices of the present invention may be used in veins and arteries. An exemplary procedure is illustrated in FIGS. 5A-I and FIGS. 6A-E. In each procedure, the device 100 is positioned in an un-tethered fashion adjacent to the treatment region 730. The sequence FIGS. 5A-I illustrate the delivery sheath 710 positioning FIG. 5A, complete deployment FIG. 5B into the lumen 10. A conventional treatment device 750 using mechanical, electrical energy or other suitable method is used to clear the undesired material 732 from the lumen wall (FIG. 5C). Some debris 734 removed from the lumen wall through the use of treatment device 750 is subsequently embolized into the blood stream (FIG. 5C) and trapped by the filter 100 (FIG. 5D). The conventional treatment device 750 is removed (FIG. 5E) and thereafter the advancement of recapture sheath 710 is advanced into recovery position (FIG. 5F). The entrapped debris 734 is then removed prior to recapturing the device with methods such as, for example, aspiration, delivery of therapeutic agents or maceration. Additionally, the device and entrapped debris can be recaptured in whole and removed via the same sheath used to recapture the device as illustrated in FIG. 5G. The device 100 and debris 734 are then withdrawn into the sheath 710 (FIG. 5H), and the sheath withdrawn from the vasculature (FIG. 5I).

Figure 6A:
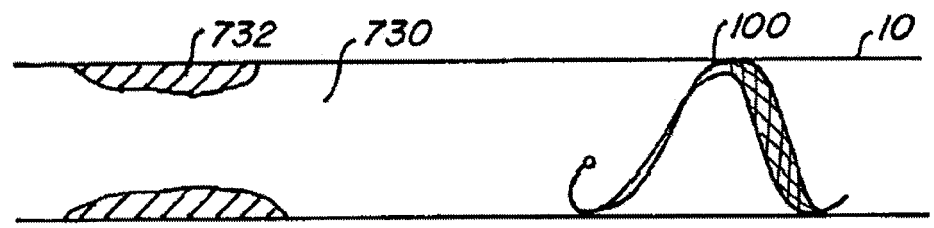
Figure 6B:
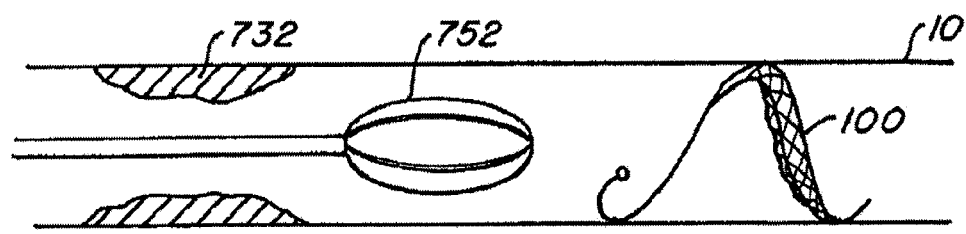
Figure 6C:
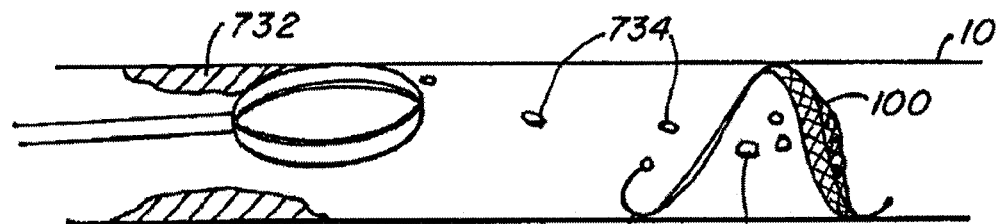
Figure 6D:
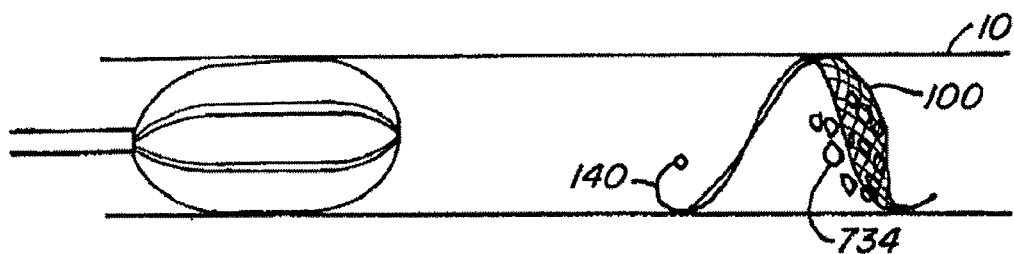
Figure 6E:
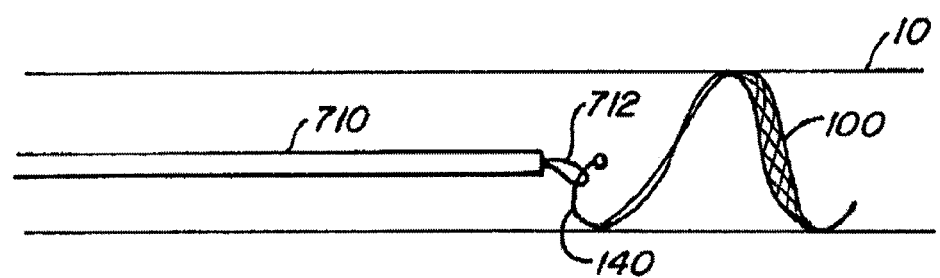

Similarly, an additional use of the invention as un-tethered distal protection is illustrated in FIGS. 6A-E, in which a balloon is used to expand the lesion 732 such as in the case of balloon angioplasty, often performed prior to stenting a vessel to keep it open. For this procedure a balloon catheter is advanced to the lesion site and inflated FIG. 6B, plaque 732 is pushed outward by the balloon (FIG. 6C), thus reestablishing normal blood flow. Any particulate matter 734 embolized by the procedure is trapped by the filter (FIG. 6D). The debris 734 can then be removed prior to filter retrieval as previously described or the device with trapped debris can be removed together.

Untethered filter embodiments can have a retrieval feature 140, such as at the ends of the filter where the elongate members of the frame attach, and anchors, which can be located on the body of the frame to help the filter to maintain its location. In some embodiments, the untethered distal protection filters 100 can be left in the blood vessel to provide protection for up to 12, 24, 48, or 72 hours. In some embodiments, the untethered filters 100 can be left in the blood vessel to provide protection for up to 1 week, 2 weeks, 3 weeks, 4 weeks, 2 months, 3 months, 4 months, 5 months or 6 months. In some embodiments, the untethered filters 100 can be left in the blood vessel perioperatively, i.e. for the duration of the patient's surgical procedure, or sub-chronically, i.e. for a predetermined period of time postoperatively. In some embodiments, periodic aspiration of the debris captured by the filter 100 can be performed to prevent or reduce blockage of the blood flow through the filter 100.

Figure 7A:
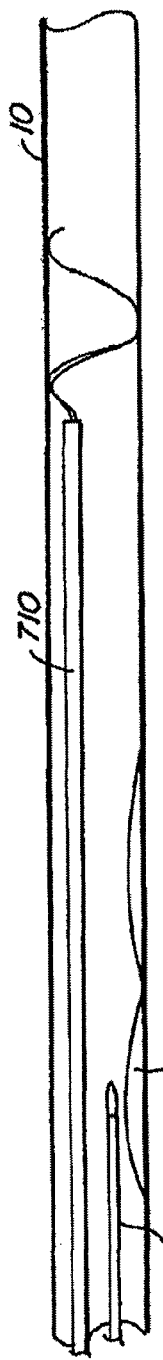
Figure 7B:
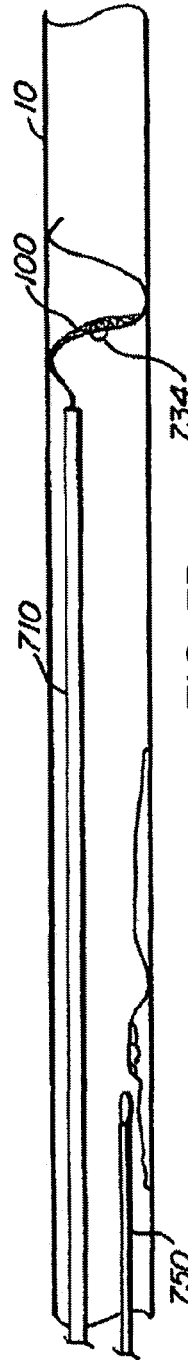

An additional method practiced widely in the art is the use of tethered distal protection adjunctive to the previously described procedures (i.e., the device 100 remains tethered during the procedure). Embodiments of the filtering device of the present invention may also be used for this purpose as illustrated in FIGS. 7A-7E. Positive control of the filter 100 is maintained via an integral wire or snare connected to the device 100. The connection between the integral wire or snare to the device 100 is maintained during the procedure and may be, in some embodiments, used as a guidewire. As illustrated in FIG. 7B, connection to the device 100 is maintained a while performing a procedure to treat the vasculature in proximity to the location (i.e., treat the lesion 732).

Figure 7C:
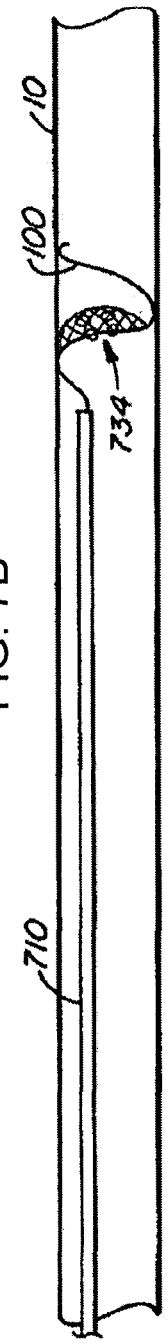
Figure 7D:
Figure 7E:

An example of a tethered distal protection method is illustrated in FIGS. 7A-7E. An embodiment of a filter device 100 is deployed distal to the lesion 732 to be treated (FIG. 7A), the treatment is initiated (FIG. 7B), and embolized material 734 is captured in the filter 100 (FIG. 7C). Thereafter, the debris 734 is removed prior to filter recapture or, alternatively, with treatment in the filter 100 via a sheath as previously described. The device 100 is recovered into the sheath (FIG. 7D) and removed from the lumen 10 (FIG. 7E).

Figure 8A:
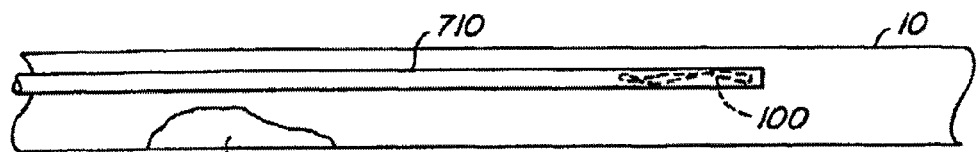
Figure 8B:
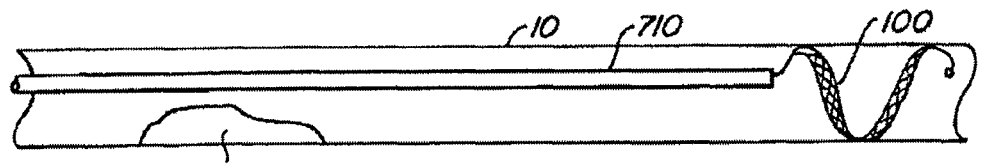
Figure 8C:
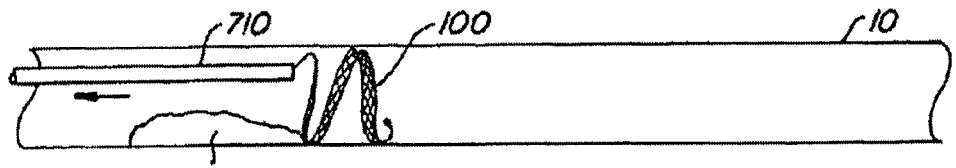
Figure 8D:
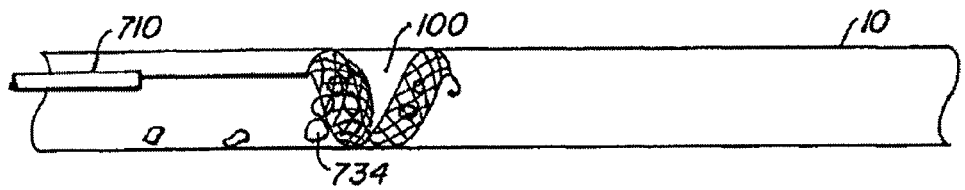
Figure 8E:
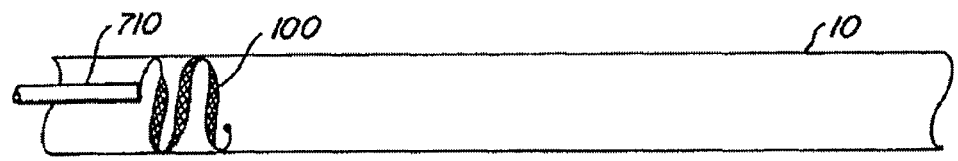
Figure 8F:
Figure 10A:
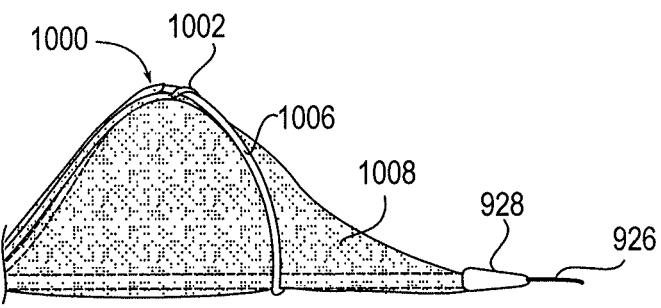
FIGS. 10A-10F illustrate an embodiment of a gap reducing feature on a distal protection filter.
Figure 10B:
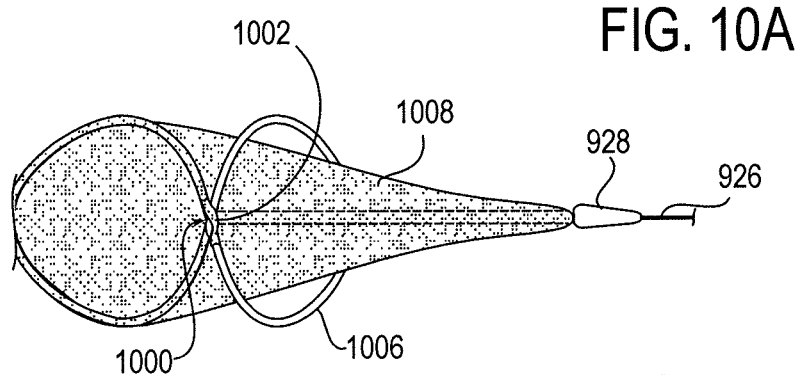
Figure 10C:
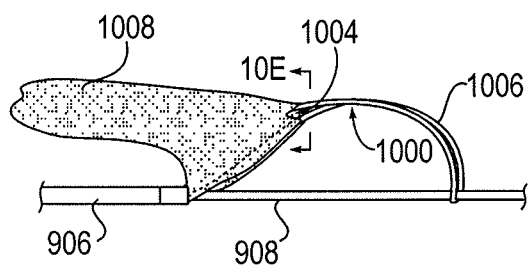
Figure 10D:
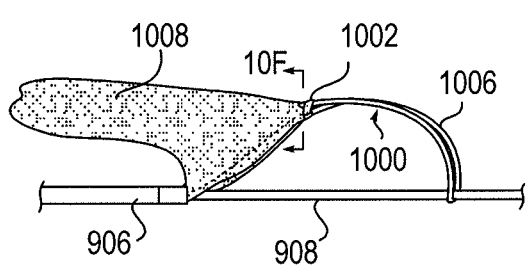
Figure 10E:
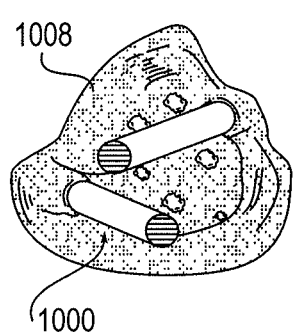
Figure 10F:
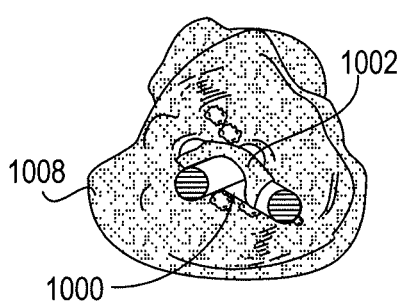

A tethered device (FIG. 7A, 8A) can also be employed to mechanically dislodge and remove embolic material 732 from a vessel 10, such as in the case of a thrombectomy. This offers a simple means of removing and trapping debris without requiring multiple devices to achieve the same goal. For this method, the tethered device is advanced downstream of the lesion site (FIG. 8A), and deployed (FIG. 8B). The tethered, deployed filter 100 is then drawn across the lesion 732 (FIG. 8C) to pull the thrombus from the vessel wall and into the filter 100 (FIG. 8D). The embolized material 734 is then removed via the methods previously described (FIG. 8E), tethered device is drawn into the sheath and removed from the lumen (FIG. 8F).

In some embodiments, as illustrated in the FIGS. 9A-9B, the distal protection device or system 900 can include two filters, a proximal filter 902 and a distal filter 904. In other embodiments, more than two filters can be used. In some embodiments, the two filters can be independently tethered to a delivery device, which can be a tube or sheath with a guide wire lumen or simply a wire, while not being tethered to each other. In some embodiments, the filters are tethered directly, i.e. are attached directly, to the delivery device. In some embodiments, such a configuration allows the distance or length between the two filters to be independently adjusted by the user by manipulating a separate hub for each filter. In addition, in some embodiments the filters can be independently oriented within a vessel by rotating the filters using a corresponding portion of the hub. For example, rotating the corresponding portion of the hub can cause the filter to rotate in a similar manner. In general, the opening of the filter is oriented to face the direction of blood flow such that blood and any debris, such as emboli, plaque fragments, calcium deposits and/or other mineral deposits, in the blood flows into the opening of the filter and into the material capture structure.

In some embodiments, the proximal filter 902 can be tethered or attached to a first sheath 906 and the distal filter 904 can be tethered or attached to a second sheath 908 that is coaxial with the first sheath 906. In some embodiments, the second sheath 908 is disposed within the first sheath 906 and extends past the distal end of the first sheath 906. This double sheath design allows each filter to be independently manipulated by manipulation of the corresponding sheath on which the filter is attached. In some embodiments, the sheaths can be braid or coil reinforced to reduce kinking. In some embodiments, the first and second sheaths can be microcatheters. In addition, the double sheath design allows the distance between the two filters to be adjusted, which allows the filters to be properly placed in the brachiocephalic trunk and the left common carotid artery. Because the distance and anatomy between the left common carotid artery and the brachiocephalic trunk is highly variable between patients, it is very helpful to be able to adjust the distance between the filters to maintain wall apposition.

In addition, in some embodiments the first and second sheaths are disposed within an outer sheath 910. In some embodiments, the outer sheath 910 can be advanced over both the first and second sheaths 906, 908 to effect capture of the attached filters 902, 904. In some embodiments, the outer sheath 910 can have a curved, deflecting, steerable distal tip portion 912 adapted to aid in navigating the curvature of the vasculature. In some embodiments, the curvature of the distal tip portion 912 can be between about 10 to 60 degrees, or between about 20 to 45 degrees, or be about 15, 20, 25, 30, 35, 40, or 45 degrees.

In some embodiments, a stop 914 is provided between the filters. In some embodiments, the stop 924 is located on the second sheath 908 at a predetermined distance proximal of the distal filter 904, which can be located on or proximal the distal end of the second sheath 908. The stop 924 can be an enlarged section of the second sheath 908, such as a thick band or other raised structure that cannot be retracted within the lumen of the first sheath 906. Therefore, the stop 924 can provide a minimum separation distance between the two filters to prevent collisions and entanglements between the two filters during the deployment or removal/recovery phases.

In some embodiments, the sheaths can be over-the-wire type sheaths and can be advanced over a guidewire 926. In other embodiments, the smaller diameter second sheath 908 with the distal filter 904 can have a rapid exchange type guidewire lumen located on the distal portion of the sheath to allow the second sheath to be exchanged in a rapid exchange type manner (not shown).

In some embodiments, the distal end of the second sheath 908 can have an atraumatic tip 928 to prevent accidental puncture of the vessel wall and to atraumatically advance the sheath.

Figures 9E, 9F:
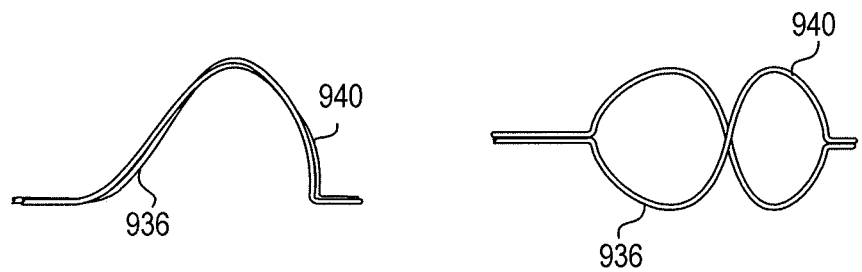
FIGS. 9E and 9F illustrate another embodiment of the frame of a distal protection filter.

In some embodiments, the proximal filter 902 and the distal filter 904 can be made from a frame 932, 934 having a proximal loop 936, 938, a distal loop 940, 942 and a slidable crossover point 944, 946 between the two loops, and a material capture structure 948, 950 attached to one of the loops two loops. In some embodiments, the sheaths pass through the interior of the loops. In some embodiments as illustrated in FIGS. 9C and 9D, the frame can be formed from a single wire or structural element that is oriented in a figure eight configuration. In some embodiments, the slidable crossover point is offset from an axis that connects the proximal end and the distal end of the frame. This offset can define the height of the filter structure. In some embodiments, the two ends of the single wire frame can be attached to one of the sheaths of the device by a fastener 952, 954 such that the sheath is located within the loop. In some embodiments as illustrated in FIGS. 9E and 9F, the frame can be formed from two wires or structural elements with opposing spirals that form a figure eight structure with a slidable crossover point that is offset from an axis that connects the proximal end and the distal ends of the frame.

In some embodiments, the proximal filter 902 can have an orientation with an opening 956 that faces towards the distal end of the device 900 and can have a material capture structure 948 attached to the trailing edge or proximal loop 936 of the proximal filter structure, while the distal filter 904 can have an orientation with an opening 958 that faces towards the proximal end of the device 900 and can have a material capture structure 950 attached to the leading edge or proximal loop 938 of the filter structure. In some embodiments, the material capture structure is attached to the proximal edge or loop of each filter.

In some embodiments, the material capture structure is pleated to accommodate the movement of the elongate members and crossover point while maintaining emboli and debris protection across the entire cross-sectional area of the lumen. In some embodiments, the material capture structure can have one or more pleats located adjacent or near the crossover point. In some embodiments, the material capture structure can have an overlapping portion at the crossover point that functions similarly to the pleat to provide material capture structure coverage in the event of separation of the elongate members at the crossover point. In some embodiments, as illustrated in FIGS. 10A-10F, the crossover point 1000 can include a crossover loop 1002 or some other restraining feature that keeps the elements of the frame that form the crosspoint point 1000 in substantial apposition or contact while still allowing the crossover elements to slide against one another. Like the pleat, the crossover loop 1002 prevents or reduces the gap 1004 that can form in between the frame 1006 and the material capture structure 1008 when the frame elements separate from one another. Such a gap may allow embolic debris to leak through the filter. Therefore, preventing or reducing the gap 1004, by for example providing additional material capture structure in the form of a pleat or by preventing or reducing the separation of the frame elements at the crossover point, can improve the capture efficiency of the filter.

Figure 11A:
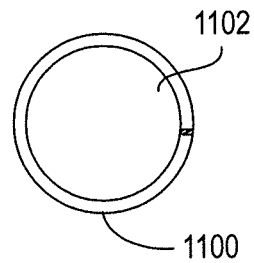
FIGS. 11A and 11B illustrate an embodiment of the construction of a frame element.
Figure 11B:
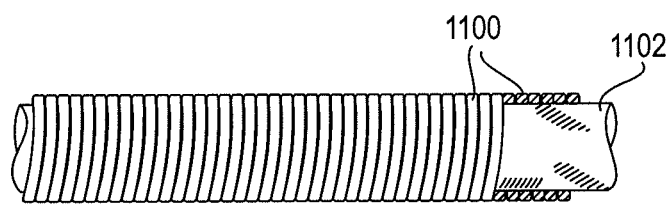

In some embodiments, as illustrated in FIG. 9A, radiopaque markers 930 can be provided on the sheaths and/or filters in order to visualize the location of the sheaths and filters during the delivery and recovery process. In some embodiments, the radiopaque marker 903 can be discrete bands incorporated in the sheaths and/or filters. In other embodiments, the sheaths and/or filters can include a coil of radiopaque wire or ribbon, such as platinum wire or ribbon, that can be incorporated into the sheaths and/or filters, making entire portions of the sheaths and/or filter radiopaque. For example, as illustrated in FIGS. 11A and 11B, a radiopaque wire or ribbon 1100 can be wrapped around a superelastic shape memory metal wire or frame core 1102, made from Nitinol for example, to form the filter frame. Similarly, a radiopaque wire or ribbon 1100 can be wrapped around distal portions of the sheaths were visualization is desired. The wrapped radiopaque wire or ribbon can also provide an irregular surface that facilitates attachment of the filter membrane to the filter frame.

Figure 11C:
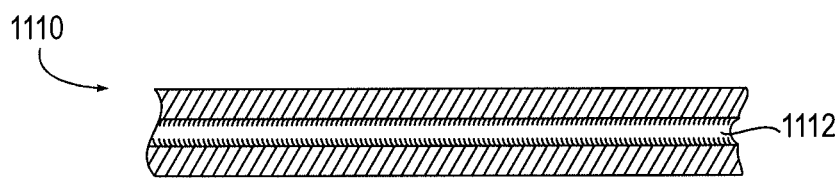
FIG. 11C illustrates a side cross-sectional view of an embodiment of a sheath.
Figure 11D:
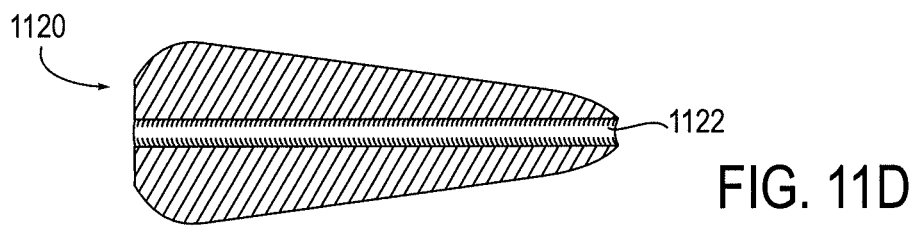
FIG. 11D illustrates a side cross-sectional view of an embodiment of an atraumatic tip.

FIGS. 11C and 11D illustrate close up cross-sectional views of a sheath 1110 and the atraumatic tip 1120. The sheath 1110 has a lumen 1112 that can receive a guidewire or another sheath. Similarly, the atraumatic tip 1120 has a lumen 1122 that can receive a guidewire.

In some embodiments, the end of the filter with the material capture structure, such as 10 the loop in which the material capture structure is attached, can be tethered or attached to the delivery device, while the end of the filter without the material capture structure, such as the loop that is not attached to the material capture structure, can remain free. In some embodiments, tethering only one end of the filter to the delivery device allows the filter greater flexibility in its deployed orientation with respect to the orientation of the delivery device, which can improve the seal or fit of the filter within the vessel. In some embodiments, both ends of the filter can be tethered to the delivery device. In some embodiments, the end of the filter without the material capture structure can be tethered to the delivery device. In some embodiments, the openings of the two filters face each other. In some embodiments, the opening of the two filters face in the same direction, which can be either towards the distal end of the filter or the proximal end of the filter. In some embodiments, the openings of the two filters face away from each other.

Figure 12A:
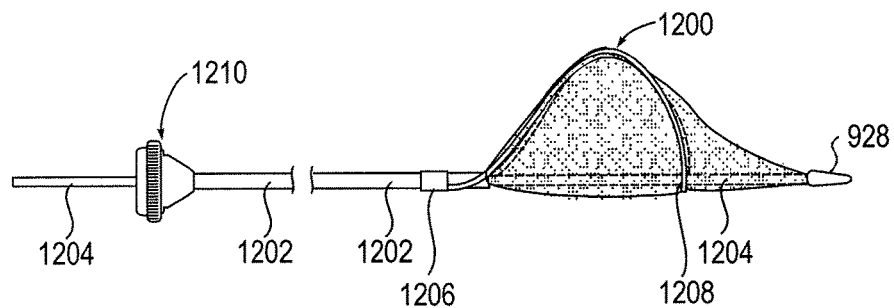
FIGS. 12A-12E illustrate an embodiment of a telescoping distal protection filter that allows control of the length of the filter.
Figure 12B:
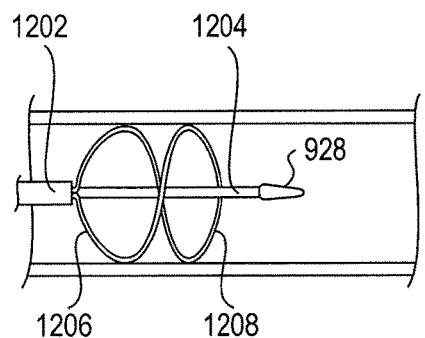
Figure 12C:
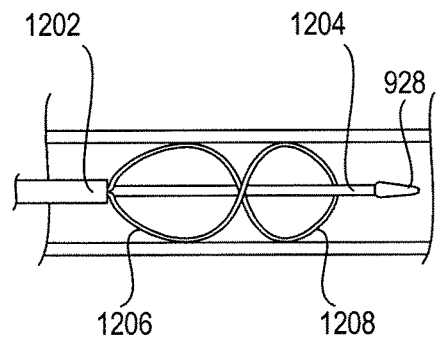
Figure 12D:
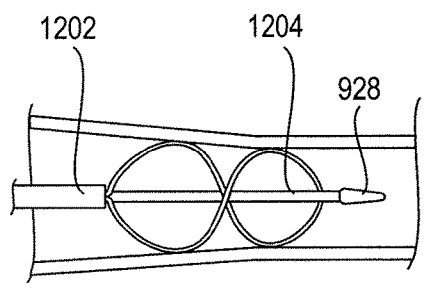
Figure 12E:
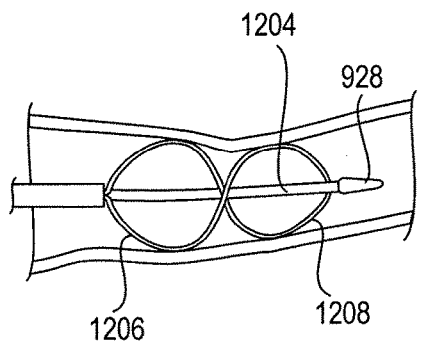

As illustrated in FIGS. 12A-12E, in some embodiments each filter 1200 can be attached to an outer sheath 1202 and an inner sheath 1204, such that the proximal loop 1206 is attached to the outer sheath 1202 and the distal loop 1208 is attached to the inner sheath 1204. This configuration allows longitudinal length and compression of the filter 1200 to be controlled by the user by manipulating a hub at the proximal end of the sheath or by manipulating the proximal end of the sheath directly. By decreasing the filter length, the height of the filter 1200 is increased allowing the filter to provide complete or substantial wall apposition in a larger diameter vessel, as shown in FIG. 12B. The slidable crossover point allows the filter to dynamically adapt to the shape of the anatomy. Once the desired filter length or height is obtained, a locking mechanism 1210, such as a Touhy-Borst lock or ratchet lock or the like which can be incorporated into or with the hub portions, can be used to lock the outer sheath 1202 to the inner sheath 1204 to fix the filter dimensions. A locking mechanism 1210 can also be used in other embodiments described herein, by for example incorporation with the hub and hub portions illustrated in FIG. 20, to lock the position of one sheath to another sheath or to the guidewire. Similarly, by increasing the filter length, the height of the filter 1200 is decreased allowing the filter to more easily provide complete or substantial wall apposition in a smaller diameter vessel, as shown in FIG. 12C. As illustrated in FIGS. 12D and 12E, the height of the filter, including the size of each individual loop, can be customized by manipulating the telescoping sheath to increase or decrease the length of the filter, where the height of the filter or individual loop is inversely related to the length of the filter or individual loop.

Figure 13A:
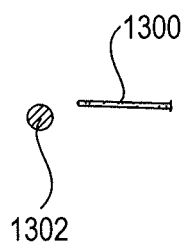
FIGS. 13A-13C illustrate an embodiment of the attachment of a filter material to the frame of the filter.
Figure 13B:
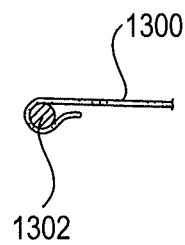
Figure 13C:
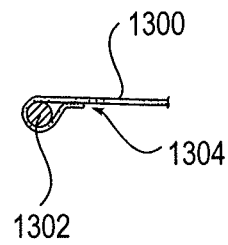

In some embodiments, the material capture structure, which can be conical for example, can be formed from a flat filter membrane or film sheet. The filter sheet can be cut and folded into the desired shape, such as a cone for example, and the seam can be thermally bonded, mechanically stitched together, or bonded together at the surface using an adhesive. In some embodiments as illustrated in FIGS. 13A-13C, the filter sheet 1300 can be attached to a loop on the filter frame 1302 by stitching with a biocompatible thread or suture, by adhesive bonding, or by thermal bonding. In some embodiments, a portion of the mouth of filter sheet 1300 can be folded over the loop on the filter frame 1302 before attachment 1304.

Figure 14A:
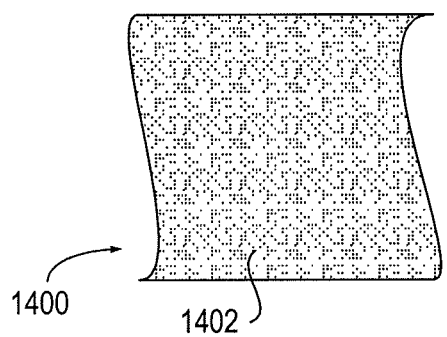
FIGS. 14A and 14B illustrate embodiments of a filter membrane with various pore distributions.
Figure 14B:
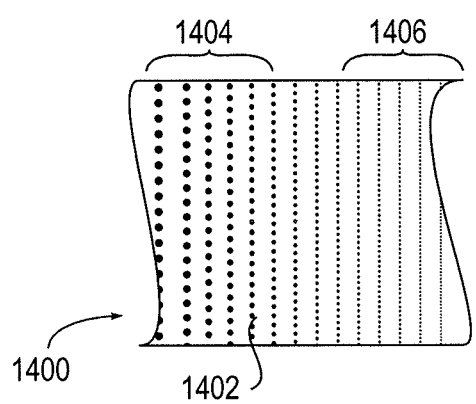

In some embodiments, the material capture structure 1400 contains a number of filter cells or pores 1402, as illustrated in FIG. 14A-14B. Filter cells or pores may be formed in a number of different ways and have a number of different shapes and sizes. The shape, size and number of filter cells or pores in a specific filter may be selected based on the use of a particular filter. For example, a filter device of the present invention configured for distal protection may have a filter cell size or pore size on the order of tens to hundreds of microns to less than 5 millimeters, or less than or equal to about 1000, 900, 800, 700, 600, 500, 400, 300, 200, 100, 90, 80, 70, 60 or 50 microns. In some embodiments, the filter cell size or pore size is formed by a selecting a filter material with a cell size or pore size suited to the desired filtration level. In some embodiments, the filter material can be a polymer membrane or film or mesh. The polymer can be polyurethane, polyethylene, nylon or the like. The polymer membrane can be between about 0.5 to 3 mil thick, or about 0.75 to 1.5 mil thick, or about 0.5, 1.0, 1.5, or 2.0 mil thick. Using a thin membrane allows the filter membrane to be easily collapsed or folded into a delivery catheter and also facilitates retrieval back into the catheter.

In some embodiments, the pores are laser drilled into the membrane. In some embodiments, the filter cells are formed from a mesh. In some embodiments, the pore size, shape, density, orientation, and distribution on the membrane can be adjusted to control the flow rate profile through the filter membrane. For example, in some embodiments, the shape of the pore can be circular, ellipsoid, oval or oblong. In a conical filter for example, an oval pore with its major axis aligned with the filter axis can present a more circular cross-sectional opening when viewed along the longitudinal axis. In addition, the pore distribution can be adjusted to provide higher pore density and/or larger pores at or near the periphery of the membrane, which is generally adjacent to the blood vessel wall after implantation. In some embodiments, the pores can be ellipsoid, oval or oblong towards the periphery of the membrane. For example as illustrated in FIG. 14B, the peripheral portions 1404 of the filter membrane that resides at or near the periphery of the blood vessel lumen can have a greater pore density and/or greater pore size than the central portions 1406 of the filter membrane that resides in the central portion of the vessel lumen. This configuration provides increased debris protection for the central portion of the filter membrane, which tends to receive debris that can be deflected from the periphery toward a central holding zone of, for example, a conical filter. As debris fills the central holding zone, the central portion of the membrane can become clogged or blocked, which can reduce or stop flow of blood through the central portion of the membrane. To compensate for the blocked central portion, the peripheral portions of the membrane can have larger pores and/or a higher pore density in order to allow a sufficient amount of blood through the debris filled filter membrane.

In some embodiments, the filter membrane has an open area between 25 to 75 percent, or between about 33 to 66 percent, or between about 40 to 60 percent, or about or at least about 35, 40, 45, 50, 55, 57, 60 or 65 percent, where the open area refers to the area occupied by the pores. Sufficient open space is important to allow an adequate flow of blood through the filter membrane and to the brain, if used to protect the neurovasculature. In some embodiments, a contrast dye or radiopaque fluid can be introduced upstream of a deployed filter to determine whether the filter membrane is occluded and the degree of occlusion. In some embodiments, the contrast dye or radiopaque fluid can be delivered through a lumen and fluid delivery port in the distal filter delivery device. In other embodiments, the contrast dye or radiopaque fluid can be delivered by a separate catheter.

Figure 15A:
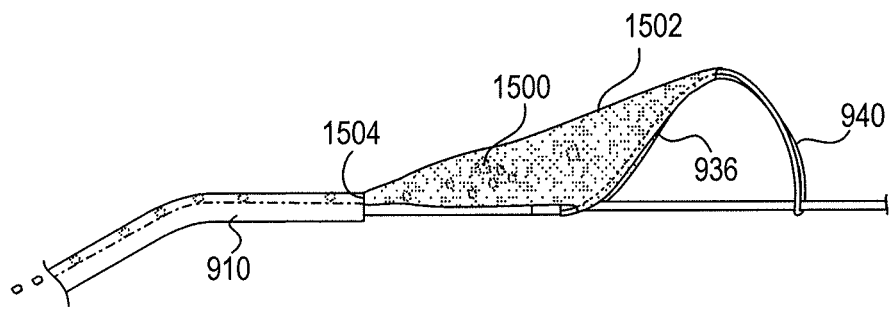
FIGS. 15A and 15B illustrate embodiments of a filter device with a built-in aspiration mechanism.
Figure 15B:
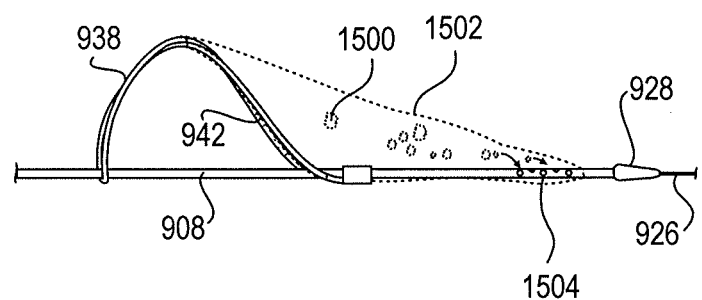

In some embodiments as illustrated in FIGS. 15A and 15B, the embolic debris 1500 can be aspirated from the material capture structure 1502 using an aspiration port 1504 included with the filter device. In some embodiments, the aspiration port 1504 can be located at or near the apex of the material capture structure 1502 where the debris 1500 is generally funneled to. In some embodiments, the aspiration port 1504 can be located on the distal end of a sheath which is connected to the apex of the material capture structure 1502. In other embodiments, the aspiration port 1504 can be located along the length of the sheath on which the material capture structure 1502 is attached. In some embodiments, one or more aspiration ports 1504 are used to aspirate the debris. In some embodiments, a separate aspiration catheter can be used to aspirate debris 1500 from the material capture structure 1502.

In some embodiments, the material capture structure, filter membrane or mesh can be coated with an anticoagulant such as heparin. In some embodiments, the other portions of the device in contact with blood, such as the catheter and tether and filter frame, can be coated with an anticoagulant. In some embodiments, the filter and/or filter membrane or mesh can be coated with a drug or pharmaceutical compound.

In some embodiments, the frame of the filter does not have any additional anchoring structures that penetrate into the vessel wall. The force exerted by the self expanding frame against the vessel wall along with the attachment of the filter to the delivery sheath during the entire procedure can provide sufficient stability to the filter and prevent substantial migration of the filter during the procedure. Relative to the venous vessels such as the vena cava, the arterial vessels are less compliant and can undergo less change in diameter over time. This makes it less necessary to provide relatively invasive fixation means. In some embodiments, the frame of the filter can include one or more anchors that do not penetrate completely through the vessel wall. In the branch arteries off the aorta, puncture through the vessel wall may lead to excessive bleeding or rupture. Therefore, in some embodiments, the anchors can be sized and designed to penetrate only part way through the vessel wall. For example, the anchors can extend radially outwards for a distance that is less than the thickness of the vessel wall, which can be less than about 0.75, 0.5, or 0.25 times the thickness of the vessel wall. In other embodiments, the anchors are designed to engage the vessel wall in an atraumatic manner.

Figure 16:
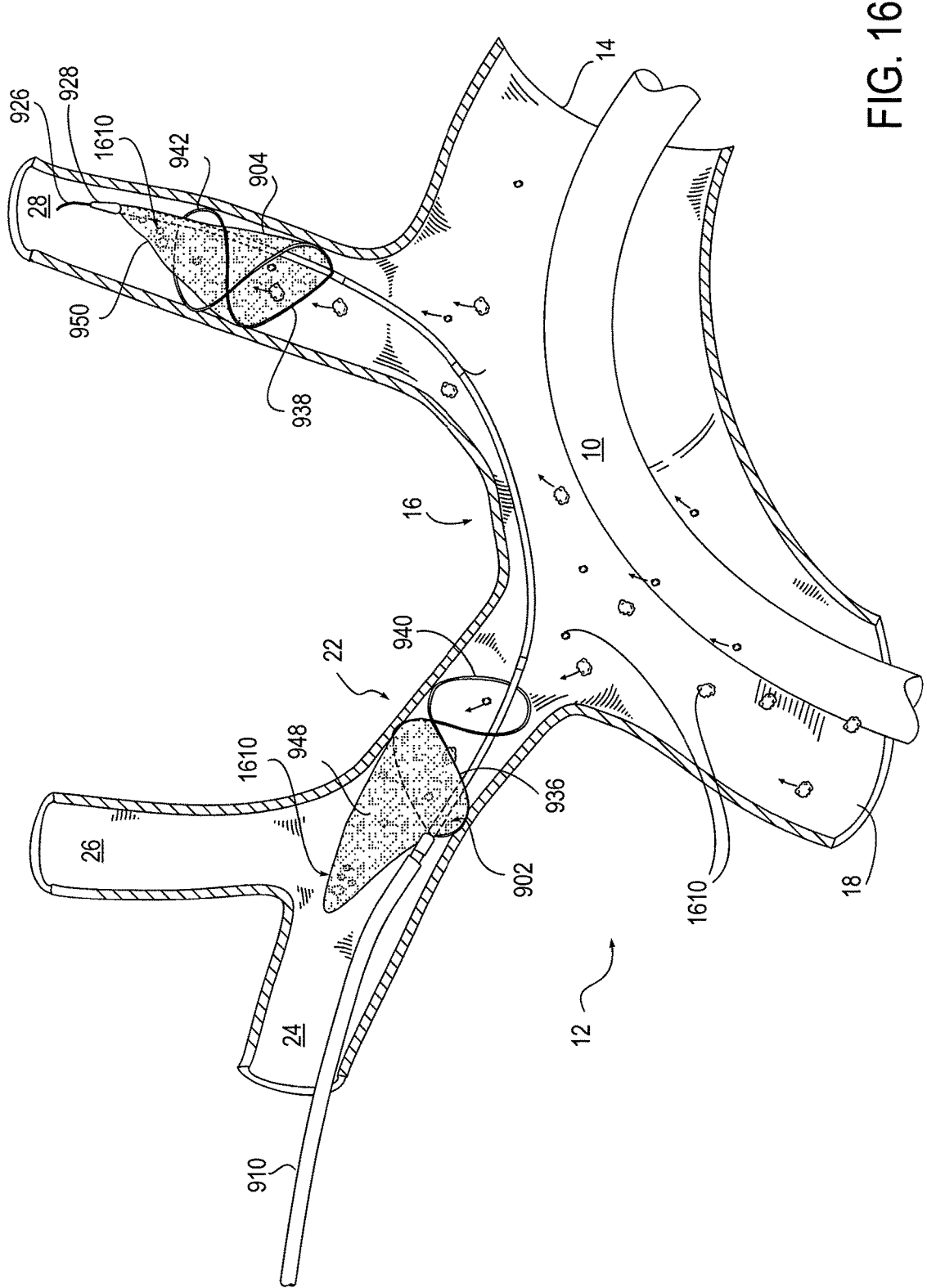
FIG. 16 illustrates an embodiment of the filtering device with a distal protection filter deployed in the left common carotid artery and another distal protection filter deployed in the brachiocephalic trunk.
Figure 17A:
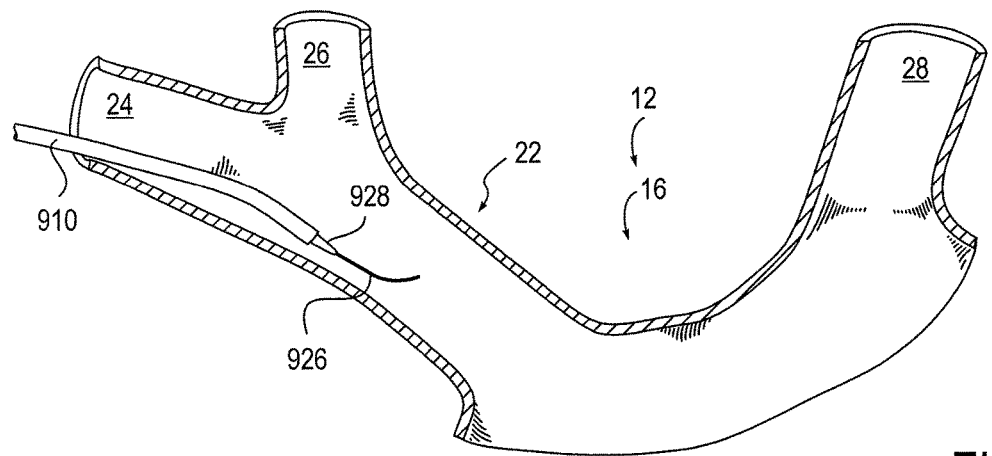
FIGS. 17A-17L illustrate an embodiment of a method of deploying distal protection filters to two arteries.
Figure 17B:
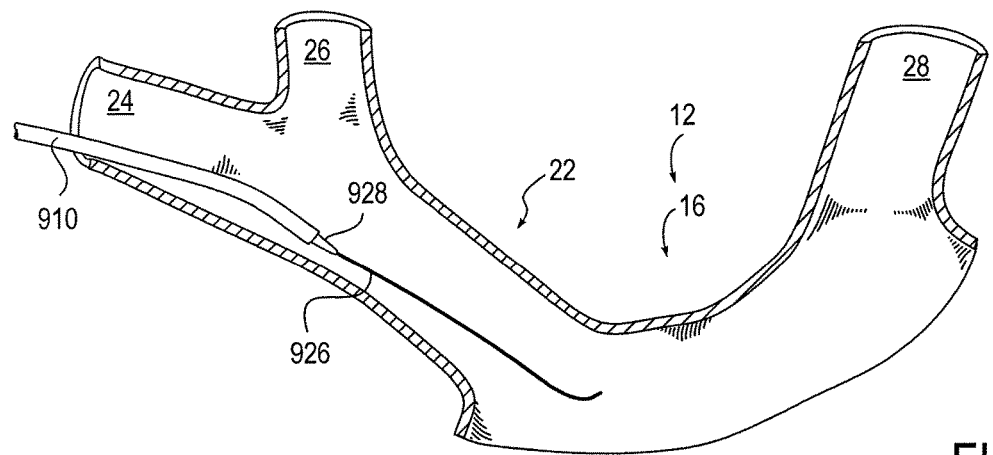
Figure 17C:
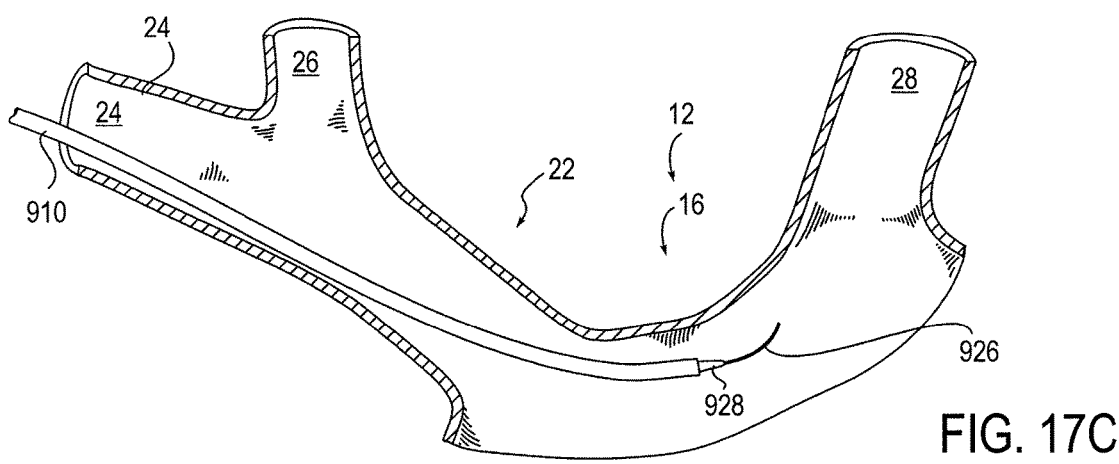
Figure 17D:
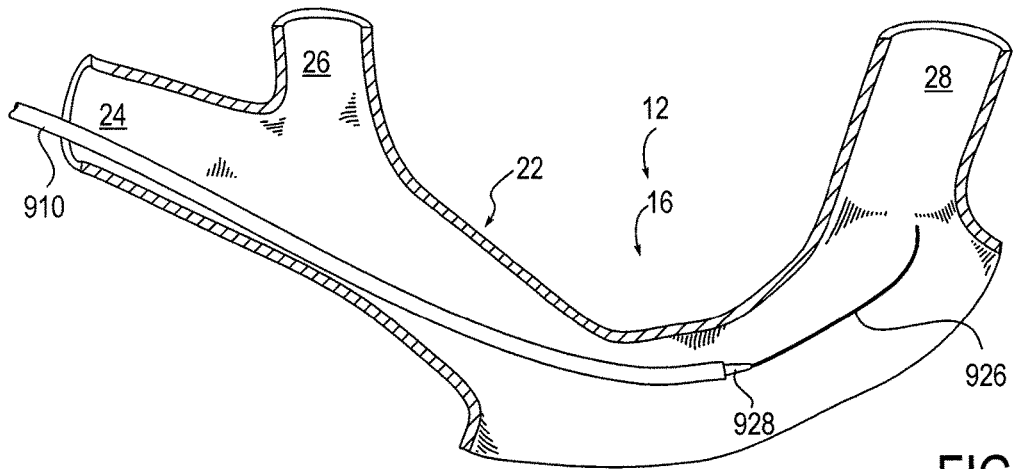
Figure 17E:
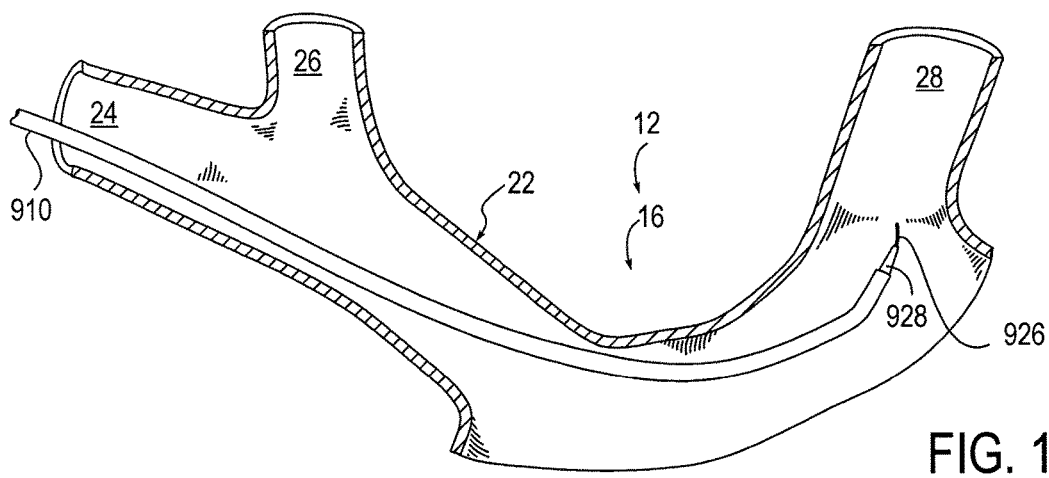
Figure 17F:
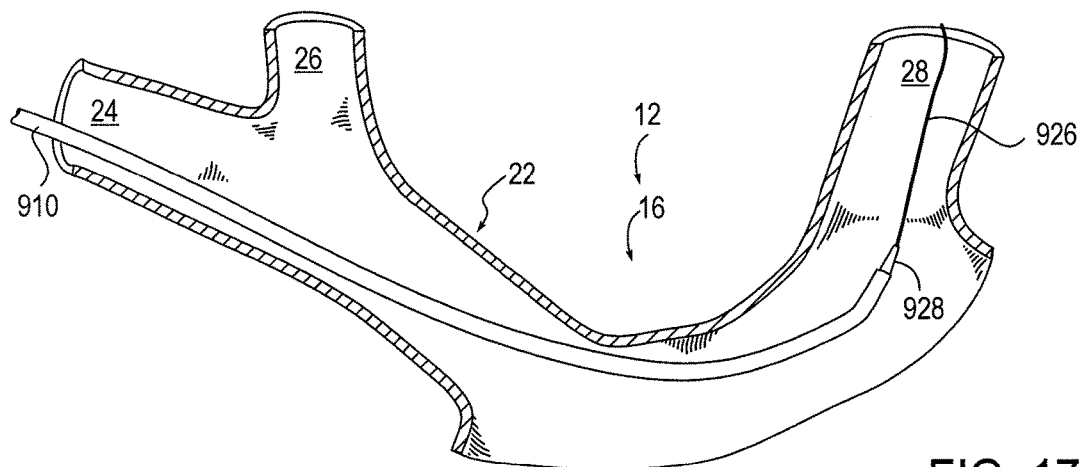
Figure 17G:
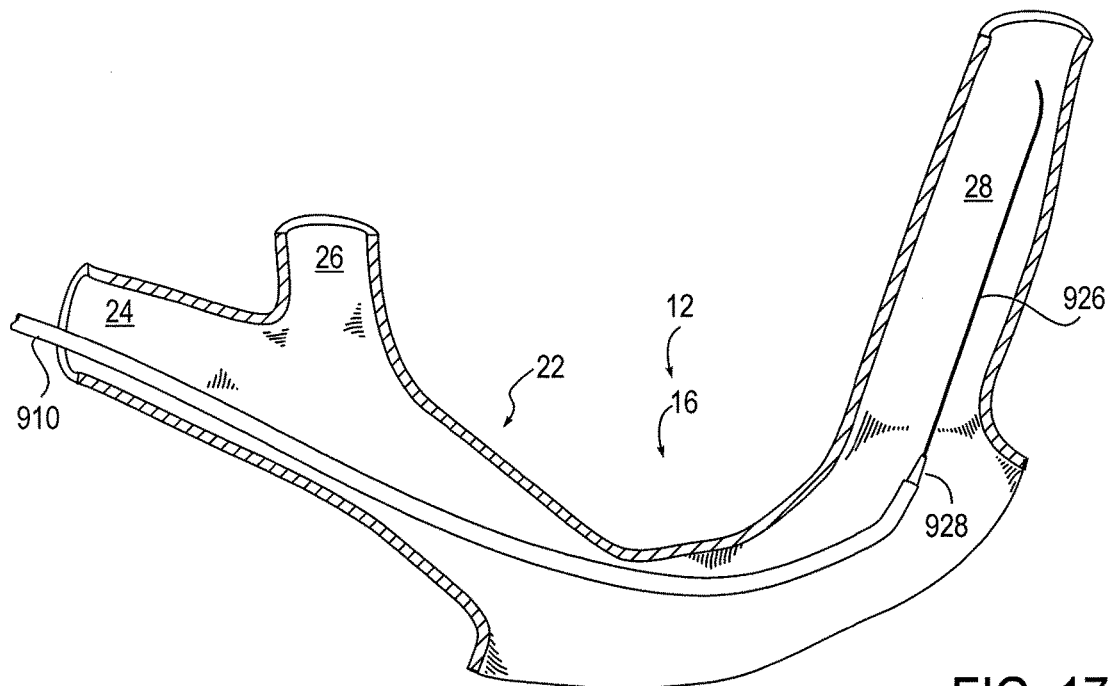
Figure 17H:
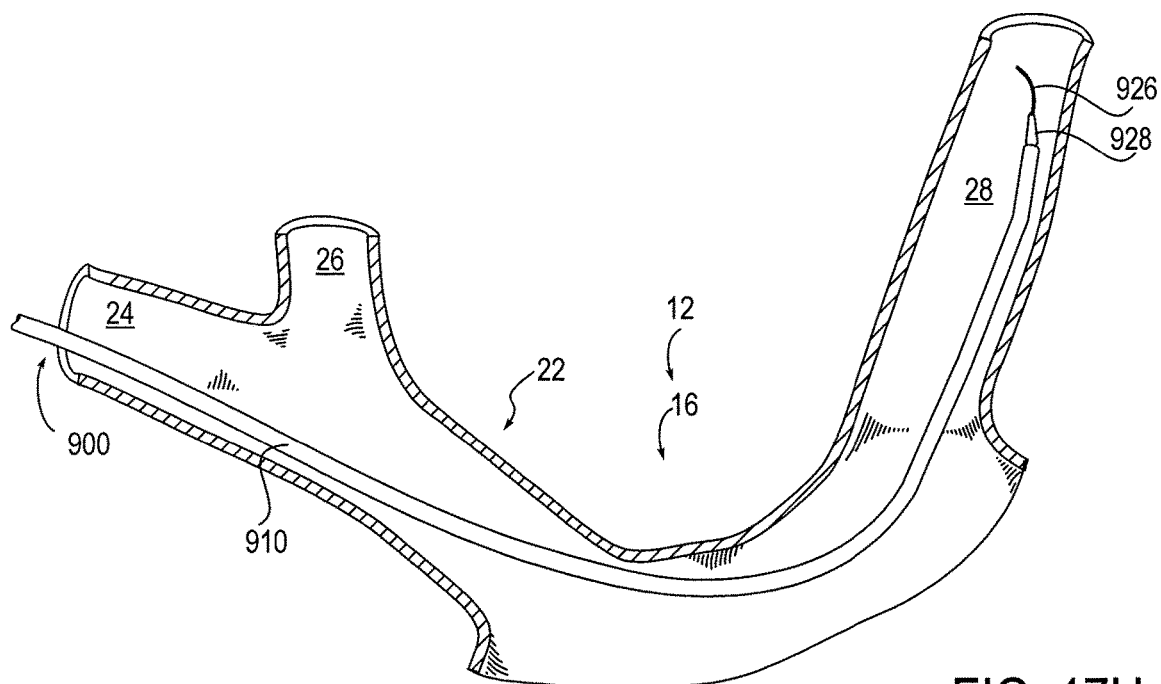
Figure 17I:
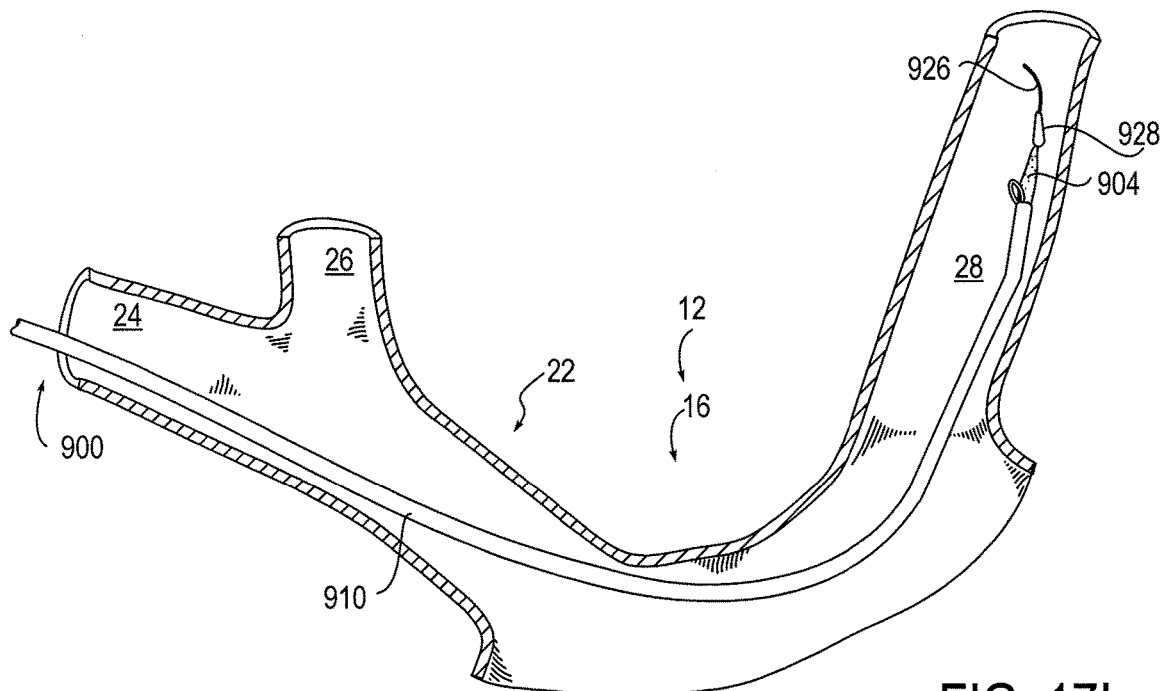
Figure 17J:
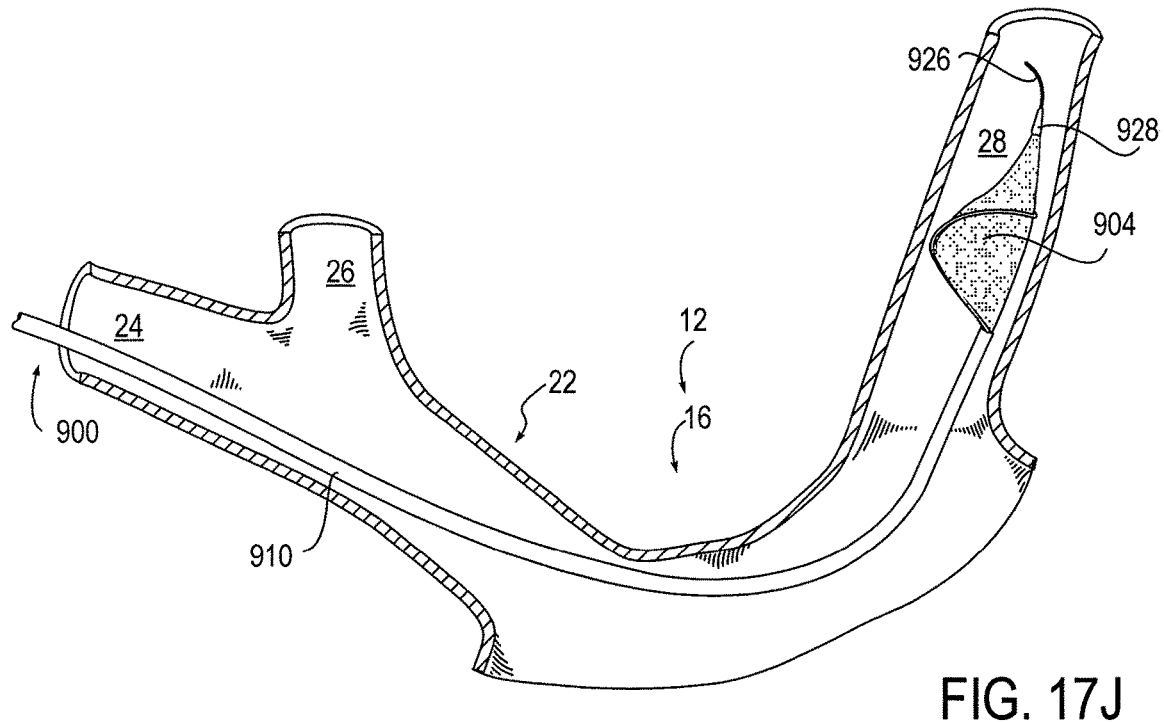
Figure 17K:
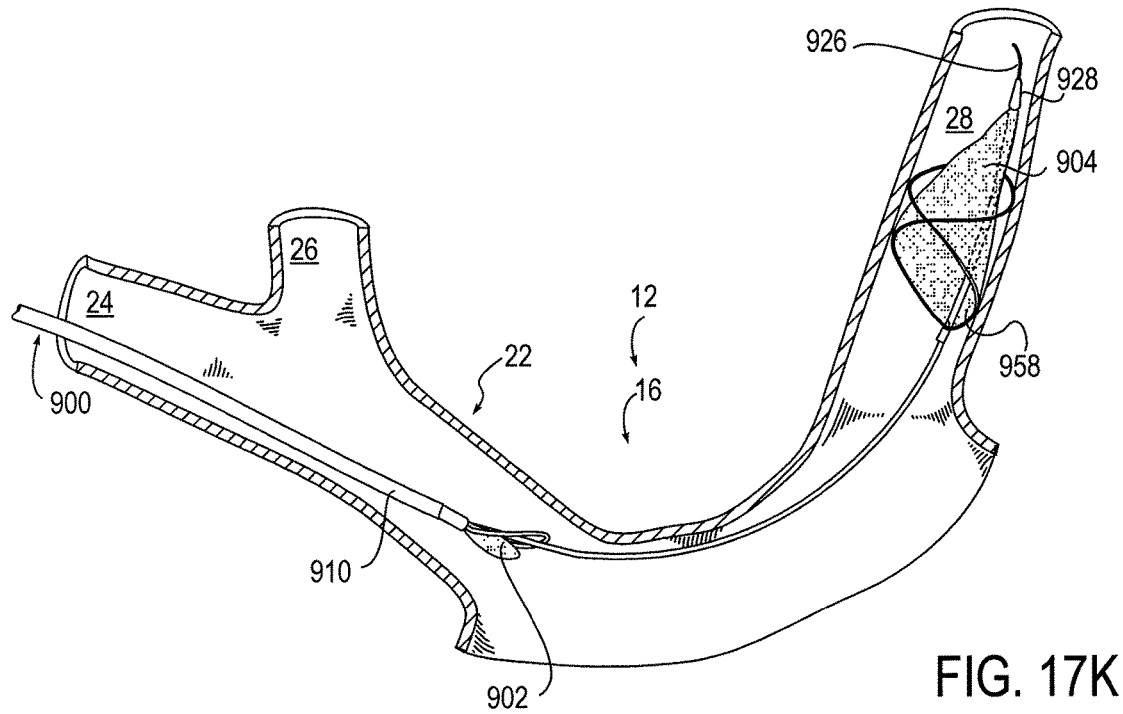
Figure 17L:
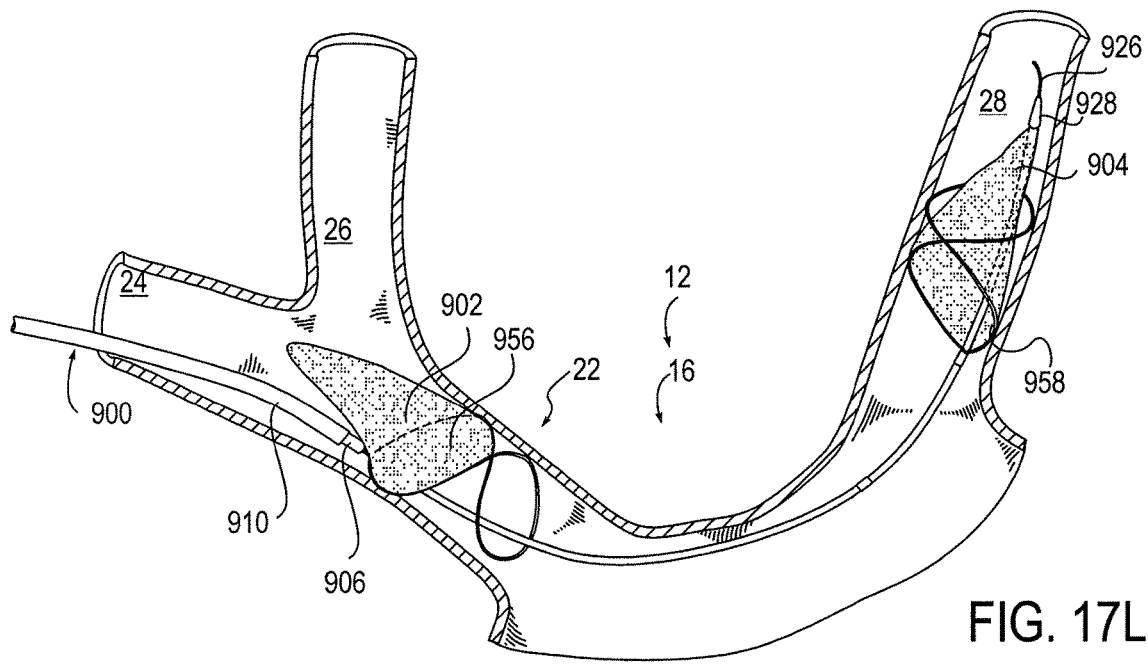

In some embodiments as illustrated in FIG. 16, the dual filter configuration allows the user to place one filter 902 in a first location in the vasculature, such as in the brachiocephalic trunk 22, and the second filter 904 can be placed in a second location in the vasculature, such as a portion of the left common carotid artery 28 that branches off the aorta 12. In some embodiments, a filter can also be placed in the left subclavian artery (not shown). In some embodiments, the goal is to provide protection of the neurovasculature by protecting the left and right common carotid artery 26, 28. Placement of filters in both the brachiocephalic trunk 22 and the left common carotid artery 28 provides emboli and debris protection for the arteries that supply blood to the brain, where emboli or debris 1610 can cause severe adverse events such as stroke. By preventing procedure related emboli and debris 1610 from reaching the neurovasculature, the risk of stroke can be reduced.

In other embodiments, the filters can be placed in other vessels branching off the aorta, such as the left subclavian artery, the right and left coronary artery, the mesenteric arteries and the renal arteries. In some embodiments, one or more of the filters can be deployed in the vasculature according to the configurations disclosed in U.S. Pat. No. 6,485,502 to Don Michael et al., U.S. Pat. No. 7,806,906 to Don Michael, U.S. Publication No. 2006/0100658 to Obana et al., and U.S. Publication No. 2008/0004687 to Barbut et al., which are hereby incorporated by reference in their entireties.

In some embodiments, the distal filter 904 can be placed first at the second location, such as the left common carotid artery 28, and then the proximal filter 902 can be retracted to the first location, such as the brachiocephalic trunk 22, and placed next. In some embodiments, the filter delivery device can access the first location and/or the second location through one of the arteries that branches off the aortic arch 16, such as the brachiocephalic trunk 22, the left common carotid artery 28 or the left subclavian artery, for example. In other embodiments, the proximal filter 902 can be placed first at the first location and then the distal filter can be advanced to the second location and placed next.

In some embodiments as illustrated in FIGS. 17A-17L, filters can be introduced into a patient's blood vessels as follows. In some embodiments as illustrated in FIGS. 17A-17G, a guidewire 926 can be introduced into a peripheral artery, such as the right brachial or radial artery, and then advanced into the right subclavian artery 24. From the right subclavian artery 24, the guidewire 926 can be further advanced into the brachiocephalic trunk 22, then into the aortic arch 16 of the aorta 12, and then into the left common carotid artery 28. In other embodiments, the filters can be delivered to the left common carotid artery and brachiocephalic trunk through the femoral artery.

In some embodiments, a sheath can be optionally advanced over the guidewire to allow the guidewire to be exchanged for a stiffer guidewire. The stiffer guidewire may be better able to maintain its position in the left common carotid artery than a more flexible guidewire when the catheter or sheath carrying the filter is advanced over the guidewire. Because the catheter or sheath carrying the filter tends to be stiffer than the first, flexible guidewire, the operator can inadvertently dislodge the first guidewire from the left common carotid artery as the catheter or sheath carrying the filter is advanced into the aortic arch and is forced to make a bend towards the left common carotid artery. Increasing the stiffness of the guidewire with the stiffer second guidewire helps resist this dislocation force exerted by the filter catheter. In addition or alternatively, a sheath with an appropriately curved tip portion can be used to help steer the guidewire 926 through the vasculature. In some embodiments, the sheath can be the outer sheath 910 of the filter delivery device 900. In other embodiments, the sheath can be separate from the filter delivery device 900 and can be removed after the guidewire 926 has been placed into the left common carotid artery 28 or other target location, and then be replaced by the filter delivery device 900.

Once the guidewire 926 is in place in the left common carotid artery 28, the filter delivery device 900 can be introduced over the guidewire 926 and advanced to the left common carotid artery 28, where the filter deployment process can begin, as illustrated in FIGS. 17G-17L. More specifically, the filter delivery device 900, which includes the plurality of sheaths with attached filters as described above, can be introduced over the guidewire 926 and into the brachiocephalic trunk 22 and then advanced towards the aorta 12. The distal filter 904 can then be advanced into the aortic arch 16, while covered by the outer sheath 910, and into the left common carotid artery 28, where the distal filter 904 can be deployed by retracting the outer sheath 910 over the distal filter 904. As the outer sheath 910 is retracted over the distal filter 904, the distal filter 904 can self-expand to engage the left common carotid artery wall. The distal filter 904 is deployed such that the mouth 958 of the distal filter 904 resides within the left common carotid artery 28. Next, the first sheath 906, which is attached to the proximal filter 902, is manipulated such that the mouth 956 of the proximal filter 902 resides in the brachiocephalic trunk 22. This manipulation can be done within the outer sheath 910, and depending on the location of the proximal filter 902 after the distal filter 904 has be deployed, can require the proximal filter 902 to be retracted or advanced into the brachiocephalic trunk 22.

Once the proximal filter 902 is in place within the brachiocephalic trunk 22, the proximal filter 902 can be deployed from the delivery device 900 to reside in the brachiocephalic trunk 22 by retracting the outer sheath 910 over the proximal filter 902. As the outer sheath 910 is retracted over the proximal filter 902, the proximal filter 902 can self-expand to engage the brachiocephalic trunk wall. As illustrated in the FIGS. 9A and 17L, both filters have openings that face each other in the stowed configuration and when deployed face the aortic arch. Such a delivery method and device configuration reduces and/or minimizes the amount of the distal protection device that occupies the aorta, thereby reducing and/or minimizing any interference with the main operational procedure to be performed, such as a percutaneous aortic valve replacement.

The length of the spacing between the two filters, which can be adjusted using the stop feature, can have an effect on whether the proximal filter will need to be retracted or advanced into the correct location in the brachiocephalic trunk. In some embodiments, the spacing between the filters is relatively long such that after deployment of the distal filter, the proximal filter is resides within the brachiocephalic trunk. In some embodiments, the proximal filter may be then advanced into position such that the mouth of the proximal filter is located within desired location within the brachiocephalic trunk. In other embodiments, the spacing between the filters is relatively short such that after deployment of the distal filter, the proximal filter resides within the aortic arch, which means that the proximal filter can then be retracted into brachiocephalic trunk.

Figure 18A:
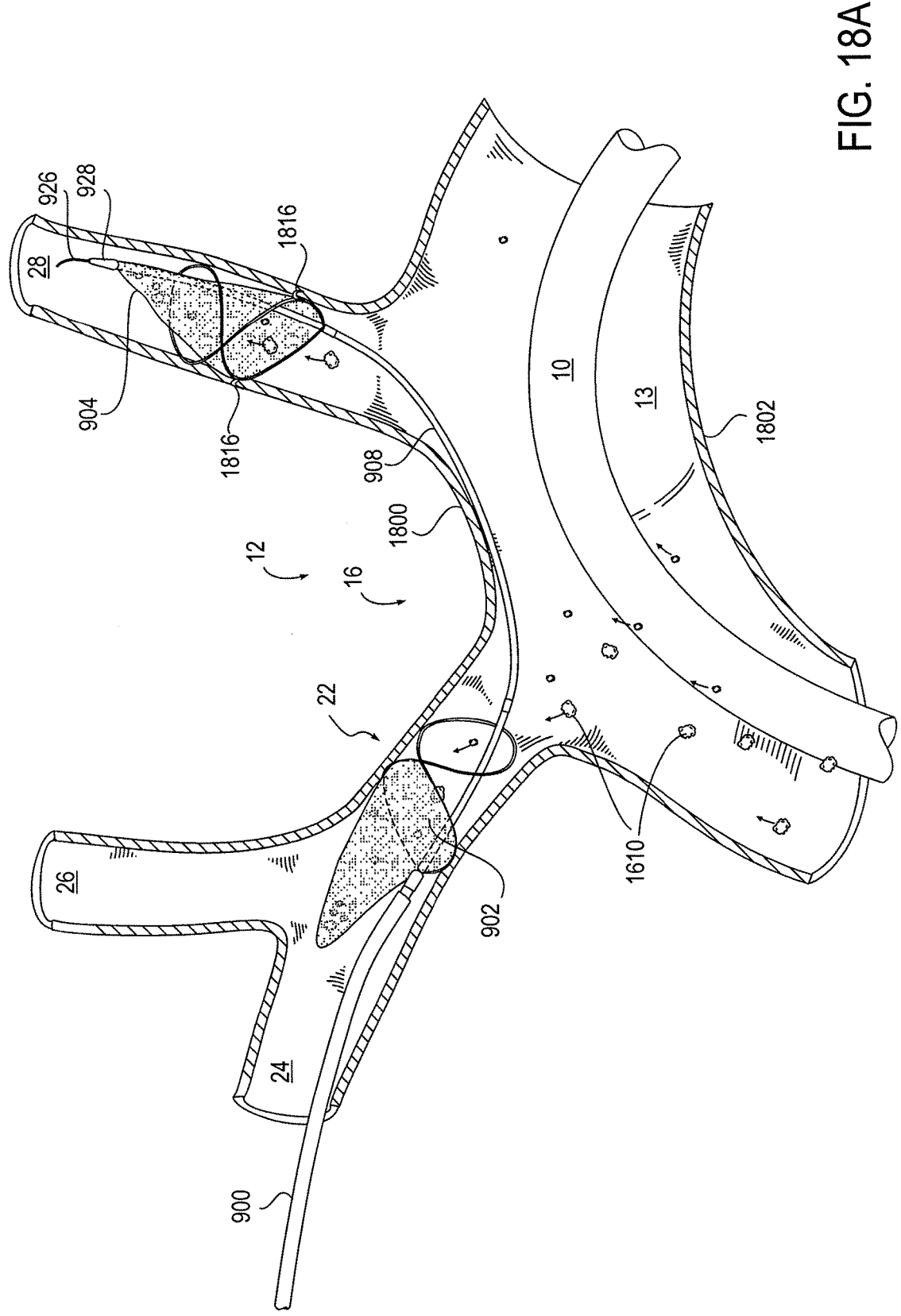
FIGS. 18A-18C illustrate embodiments of various orientations of the sheath within the aorta to minimize or reduce interference with a procedure catheter.

Furthermore, the spacing between the two filters can have an effect on the amount and/or the configuration of the sheath or catheter than remains in the aortic arch when the filters are in place. It can be important to minimize or reduce the obstruction of the aortic lumen by the sheath or catheter in order to minimize or reduce interference with subsequent surgical procedures, such as percutaneous aortic valve repair PAVR that require insertion of catheters and other medical devices through the aortic arch. Collision of the PAVR catheter with the sheath or catheter of the distal protection filter, can cause dislodgement of the filters and/or entanglement between the devices and/or otherwise interfere with the surgical procedure. Various embodiments of the system and method that minimize or reduce obstruction of the aortic lumen are illustrated in FIGS. 18A-18E. In some embodiments as illustrated in FIG. 18A, in order to minimize or reduce the obstruction of the aortic lumen 13 by the sheath 908 or catheter of the filter device 900, the sheath 908 or catheter portion between the proximal filter 902 and the distal filter 904 can be kept taut or under tension to minimize or reduce the length of the sheath 908 or catheter between the two filters. In this configuration, the sheath 908 or catheter tends to abut or conform to the top 1800 of the aortic arch 16, also referred to as the outer radius 1800 of the aortic arch 16, between the left common carotid artery 28 and the brachiocephalic trunk 22. In some embodiments, the frame of the proximal filter 902, the distal filter 904 and/or sheath 908 or catheter portion between the two filters can include one or more anchors or securement elements 1816 that helps secure the sheath 908 or catheter to the top portion of the aortic arch 16 by allowing the user to apply tension to the sheath 908 which and/or by using anchors 1816 to secure the sheath 908 to the outer radius 1800. The anchors 1816 can be configured to extend towards the aortic arch wall, or can be manipulated to face the aortic arch wall, so that the likelihood that the anchors 1816 interfere with the surgical procedure catheter 10 or device is minimized or reduced. In some embodiments, anchors 1816 can have relatively short length to ensure that the anchors do not puncture the wall of the aortic arch. In some embodiments where the sheath 908 has an anchor, anchors 1816 can be located on the portion of the sheath opposite the crossover point of the proximal filter 902 and/or the crossover point of the distal filter 904. In some embodiments, the filter device 900 can have a plurality of anchors 1816 located in any of the locations described herein.

Figure 18B:
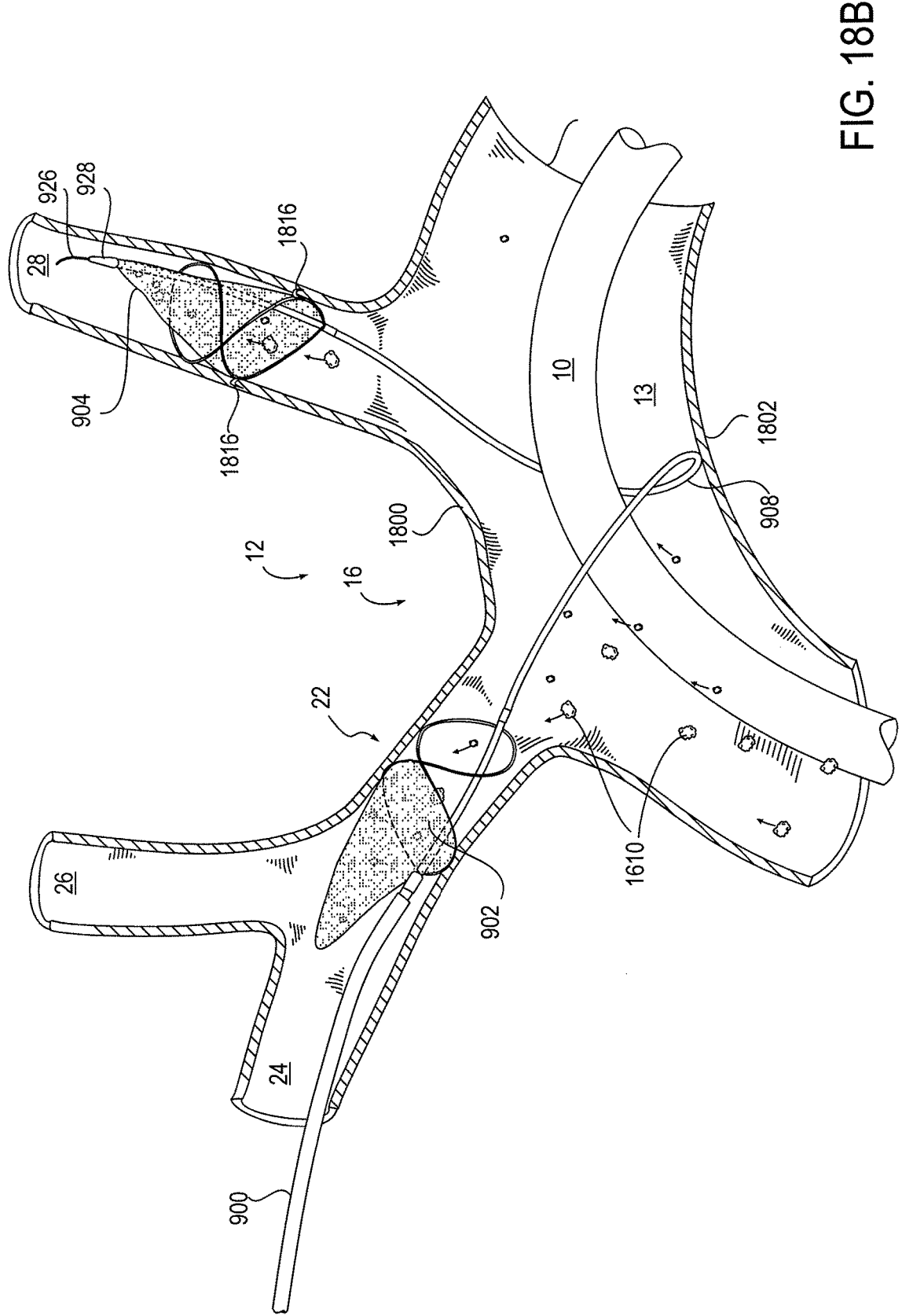
Figure 18C:
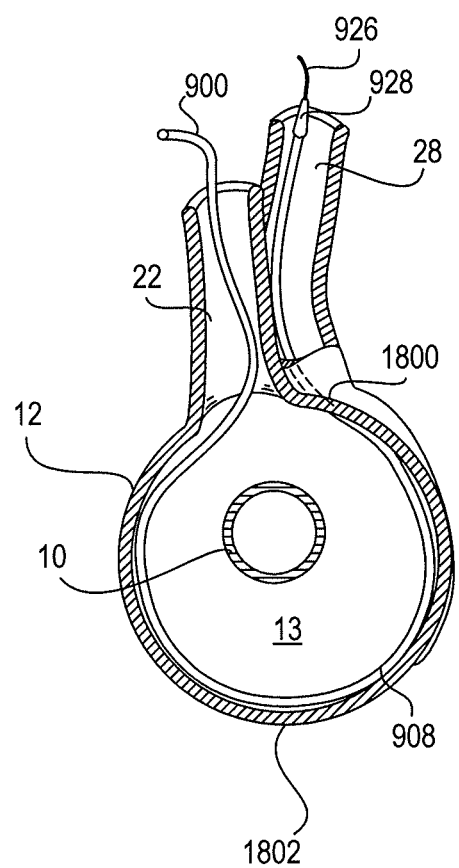

In other embodiments as illustrated in FIGS. 18B and 18C, the portion of the sheath 908 or catheter in the aortic arch 16 can extend downwards from the left common carotid artery 28, staying against inner wall the aortic arch and traversing from the outer radius 1800 of the aortic arch 16 proximate the left common carotid artery 28 to the inner radius 1802 of the aortic arch 16, before extending upwards towards the outer radius 1800 of the aortic arch 16 proximate the brachiocephalic trunk 22 and then into the brachiocephalic trunk 22, again staying against the aortic arch inner wall. This configuration results in a U shaped configuration for the sheath 908 or catheter while staying substantially out of the aortic arch lumen 13. In this embodiment, the distal filter 904 and/or sheath 908 or catheter can also have anchors 1816 as described above.

Figure 18D:
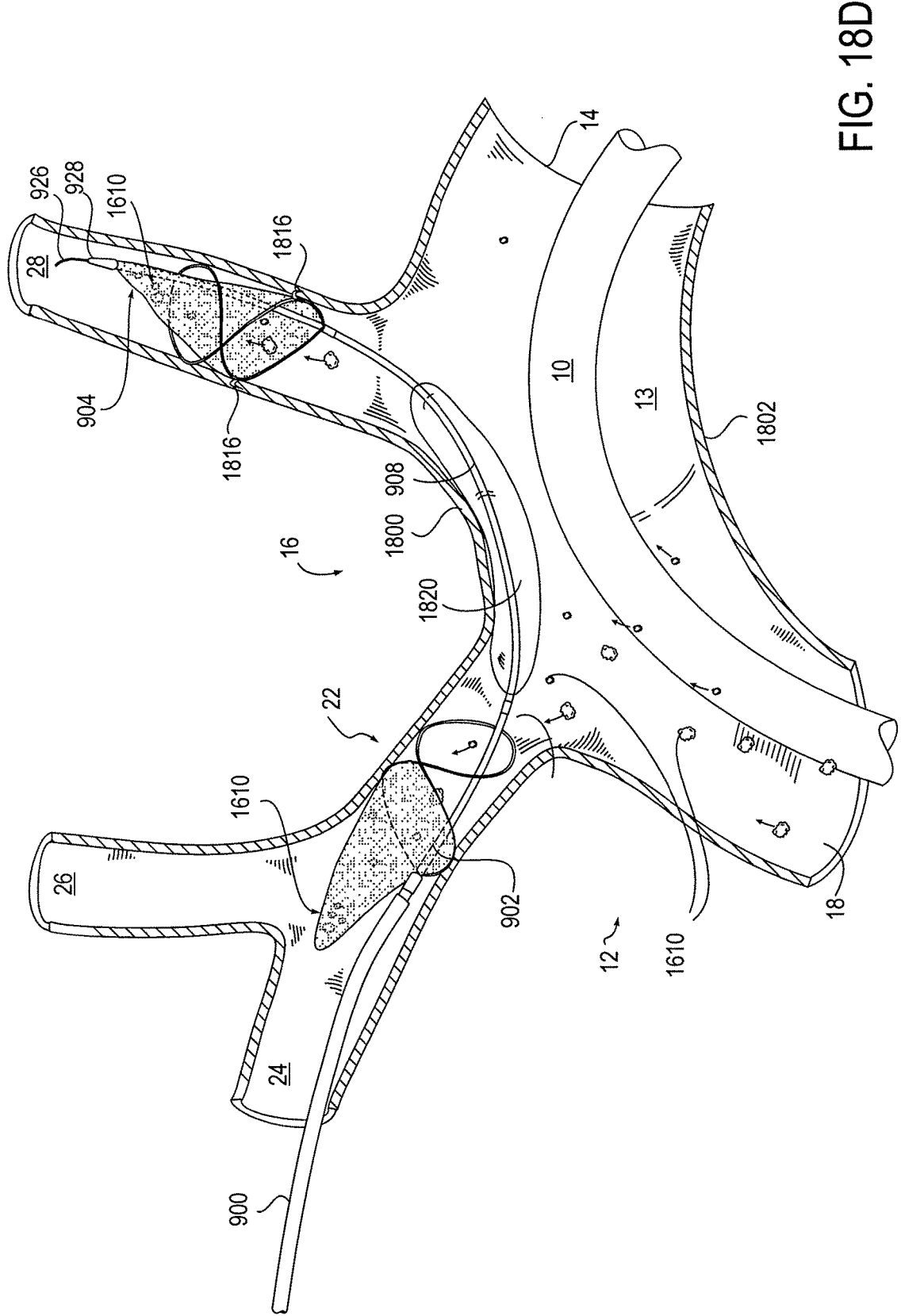
FIGS. 18D and 18E illustrate embodiments of various deflection mechanisms for deflecting a procedure catheter away from the filtering device.
Figure 18E:
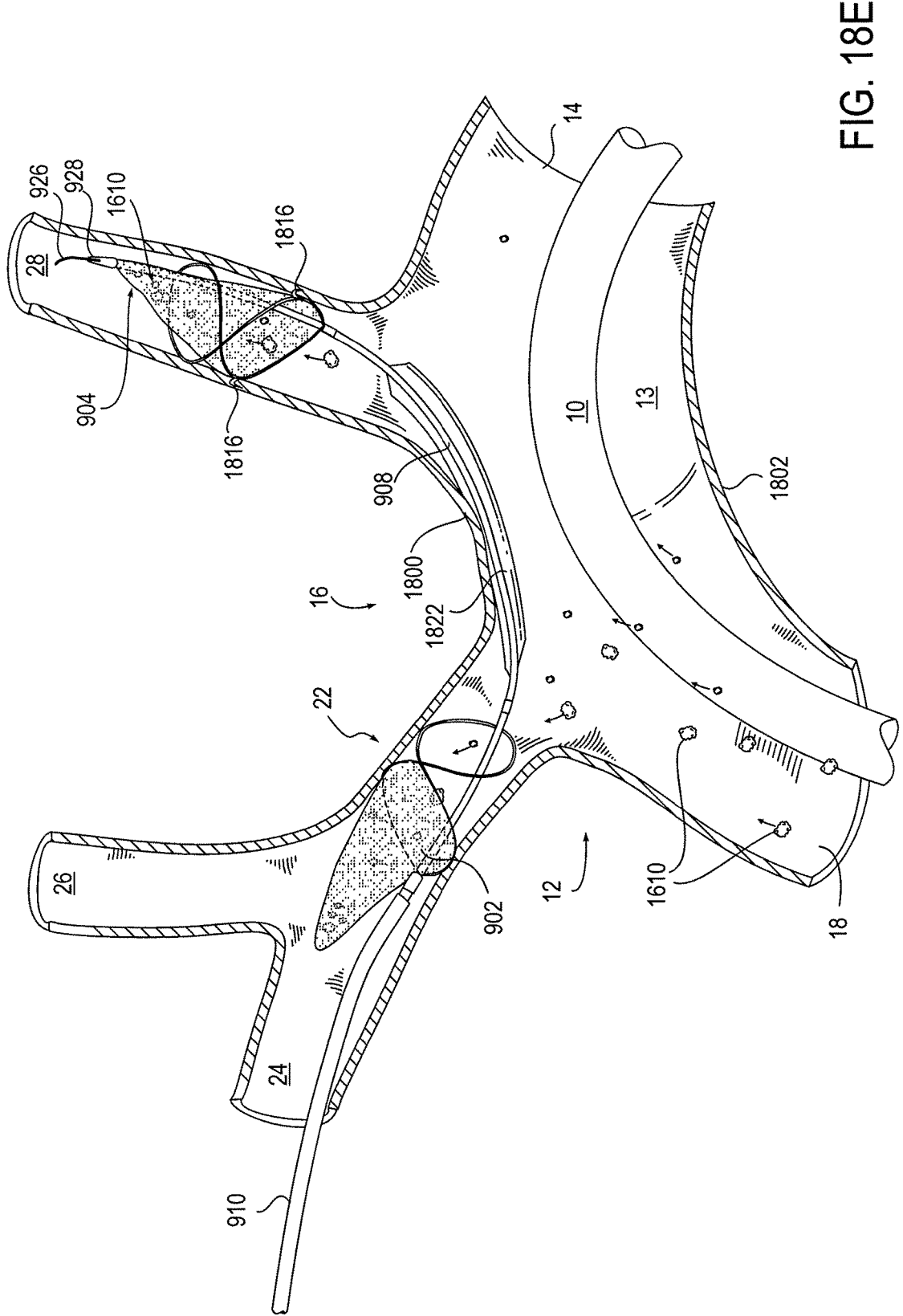

In other embodiments as illustrated in FIGS. 18D and 18E, which are modifications of the embodiment illustrated in FIG. 18A, a deflection mechanism can be incorporated on the portion of the sheath 908 or catheter between the two filters that resides against outer radius 1800 of the aortic arch 16. For example, FIG. 18D shows a balloon deflection mechanism 1820 that can be inflated after the filters are positioned in order to deflect the procedure catheter 10 from entanglement with the sheath 908 of the filter device 900. As the procedure catheter 10 is inserted into the aortic arch 16, it makes contact with the balloon deflection mechanism 1820 instead of the getting potentially entangled with the sheath 908. FIG. 18E shows various embodiments of the deflection mechanism, where a deflection shield 1822 is used in place of the balloon deflection mechanism 1820. The deflection shield 1822 can be flexible and flat and can be rolled up around the sheath 908 during delivery of the distal filter 904. As the outer sheath is further retracted, the deflection shield 1822 can be deployed and can unfurl into its flat configuration.

In other embodiments, the portion of the sheath 908 between the two filters can have a suture tether that allows the sheath 908 to be sutured against the aortic arch wall.

Figure 19D:
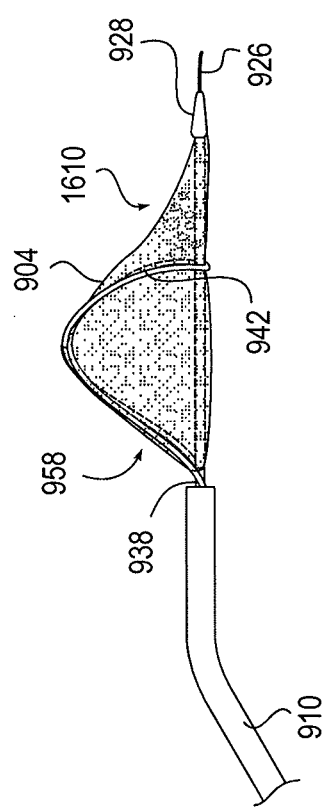
Figure 19E:
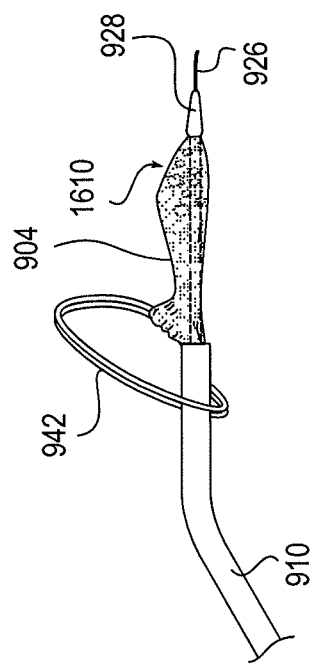
Figure 19F:
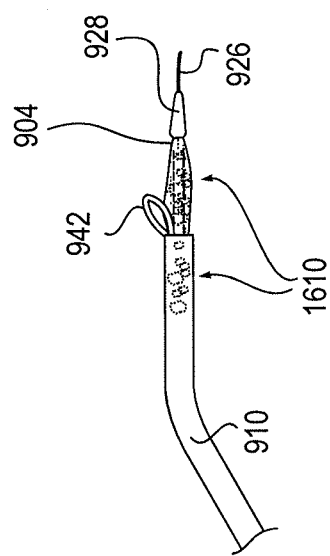

After completion of the main operation procedure, the process of removing the distal protection filters and any captured debris can be initiated, as illustrated in FIGS. 19A-19F. For example, in some embodiments, an outer sheath 910 can be advanced over the proximal filter 902 and the distal filter 904. As the outer sheath 910 is advanced over the first sheath 906, it first contacts the proximal edge or loop 936 of the proximal filter 902, which in some embodiments, also serves as the attachment for a material capture structure 948. As the outer sheath 910 is advanced over the proximal edge or loop 936 of the proximal filter 902, it causes the proximal edge or loop to collapse 936 and close the mouth or opening 956 of the material capture structure 948, thereby sealing the debris 1610 within the material capture structure 948 while not causing extrusion of the debris 160 out of the proximal filter 902. As explained above, this can occur because the apex 1916 of the material capture structure 948 is unattached to the first sheath 906. The outer sheath 910 can then be further advanced over the sealed off portion of the material capture structure 948 containing the trapped debris 1610 such that the apex 1916 is the last part of the material capture structure 948 to be encompassed by the outer sheath 910. In some embodiments, as shown in FIGS. 19B and 19E, the distal loop 940, 942 of the proximal filter 902 and/or the distal filter 904 can move proximally during the closure of the mouth of the material capture structure such that the distal loop can be proximal the crossover point during a portion of the mouth closure procedure. As the mouth closure procedure progresses, the distal loop can move distally such that the distal loop is again distal the crossover point before being completely withdrawn into the outer sheath. The outer sheath 910 can then be advanced over the second sheath 908 to the distal filter 904, where it first contacts the proximal edge or loop 938 of the distal filter 904, which in some embodiments also serves as the attachment for a material capture structure 950. Next, the outer sheath 910 can be advanced over the proximal edge or loop 938 of the distal filter 904 to close the opening 958 the material capture structure 950 to trap the debris 1610 within the material capture structure 950 without causing extrusion of the debris 1610 out of the distal filter 904. The outer sheath 910 can then be advanced over the sealed off portion of the material capture structure 950 of the distal filter 904 and the distal protection device and/or system can be removed from the patient.

In some embodiments, the outer sheath of the distal protection device can be swapped out for a larger sheath or smaller sheath by removing the hub, then removing the original sheath, then inserting the new larger or smaller sheath, and then reattaching the hub. In some embodiments, the hub can be simply twisted off and twisted back on. The ability to swap out one sheath for a larger or smaller sheath can be useful for using the smallest sheath that is capable of enclosing the filter and the debris captured by the filter. However, if a large amount of debris is captured by the filter, it may be desirable to use a larger sheath to recover the filter, especially if the operator has difficulty or cannot advance the smaller sheath over the trapped debris. For example, FIG. 20 illustrates an embodiment of a plurality of removable hubs. There is an outer sheath hub 2000 that controls manipulation of the outer sheath 910, a proximal filter hub 2002 that controls the first sheath 906 and the proximal filter attached to the first sheath, and a distal filter hub 2004 that controls the second sheath 908 and the distal filter attached to the second sheath. Each of these hubs is detachable, which allows the outer sheath to be removed and replaced if desired. In some embodiments, the hubs can be lockable to lock the position of the sheaths. For example, one hub can be used to lock the position of the attached sheath while the other sheaths can be advanced or withdrawn, allowing the distance between the filters to be manipulated.

In some embodiments, the distal protection filters can be removed after the medical procedure is complete. In other embodiments, the distal protection filters can be left in for a predetermined amount of time before the filters are removed from the blood vessels. In some embodiments, the filters can be left in for up to 12, 24, 48, or 72 hours before removal. In some embodiments, a clogged filter can be swapped out with a new filter. In some embodiments, the filters can be left in the blood vessels to provide protection for up to 1 week, 2 weeks, 3 weeks, 4 weeks, 2 months, 3 months, 4 months, 5 months or 6 months when used in conjunction with periodic aspiration of the debris captured by the filters to prevent or reduce blockage of the blood flow through the filter. In some embodiments, the filters can be left in the blood vessel perioperatively, i.e. for the duration of the patient's surgical procedure, or sub-chronically, i.e. for a predetermined period of time postoperatively.

The distal protection filters described above can be used to capture debris that is generated by any medical procedure performed in the heart or circulatory systems, such as percutaneous aortic valve replacement (PAVR), transcatheter aortic valve implantation (TAVI), thoracic endovascular aortic repair (TEVAR), coronary artery bypass graft surgery (CABG), off-pump coronary artery bypass surgery (OP-CAB), mitral valve replacement (MVR), aortic valve replacement (AVR), left ventricle assist device, maze procedures, left ventricle catheterization, mitral valve procedure, electrophysiology (EP) ablation, closure of atrial septal defect (ASD), closure of patent foramen ovale (PFO), and closure of left atrial appendage (LAA).

In some embodiments, a pressure sensor and/or an intravascular ultrasound (IVUS) transducer can be added to or incorporated into the delivery system and method. The pressure sensor can be used to measure the pressure at various positions within the vasculature, which can be used to determine blood flow, while the intravascular ultrasound (IVUS) transducer can be used to measure fluid flow and/or provide imaging within the vessel. In some embodiments, the pressure sensor and/or IVUS transducer can be incorporated into the guidewire at one or more locations, such as the distal end or distal portion of a guidewire, as described in U.S. Pat. Nos. 8,277,386, 6,106,476 and 6,780,157 which are hereby incorporated by reference in their entireties for all purposes, as well as being incorporated into intermediate and proximal portions of the guidewire. The guidewire with the pressure sensor and/or the IVUS transducer can be used much like a normal guidewire to help navigate the delivery device through the vasculature, with the added benefit of providing pressure measurements and ultrasound imaging to help in the navigation, to visualize the device placement site, and to monitor and ensure proper device deployment. In some embodiments, the IVUS transducer generates image slices as it is advanced and retracted which can then be assembled together to form a three dimensional reconstruction of the vasculature and/or the device within the vasculature. In some embodiments, the guidewire with the pressure sensor and/or IVUS transducer can be fastened to a catheter in a similar manner to that described below for a catheter having a pressure sensor and/or IVUS transducer that is fastened to another catheter.

Figure 21A:
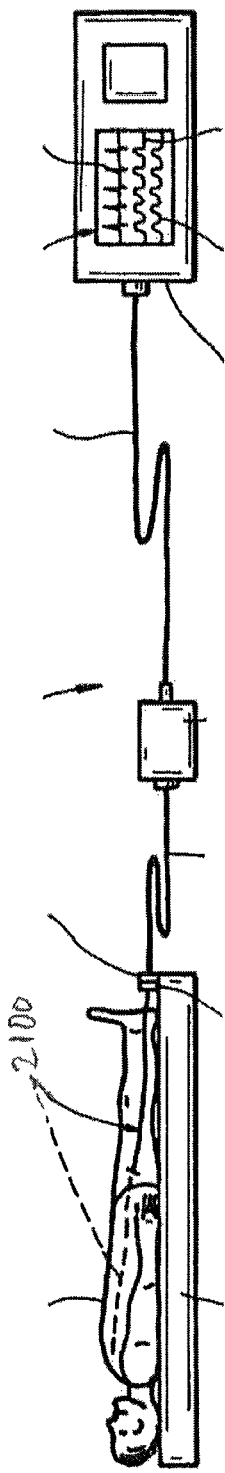
FIGS. 21A-21C illustrate an embodiment of guidewire having both a pressure sensor and an IVUS transducer.
Figure 21B:
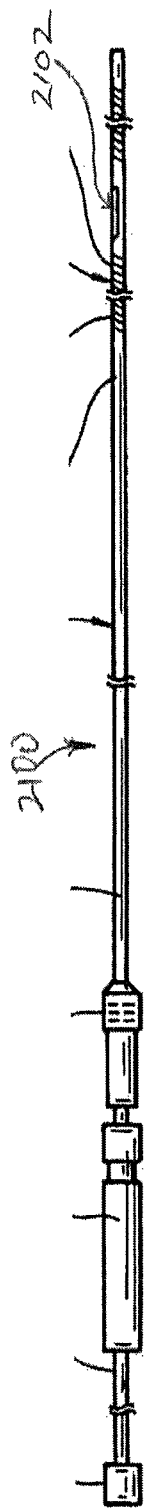
Figure 21C:
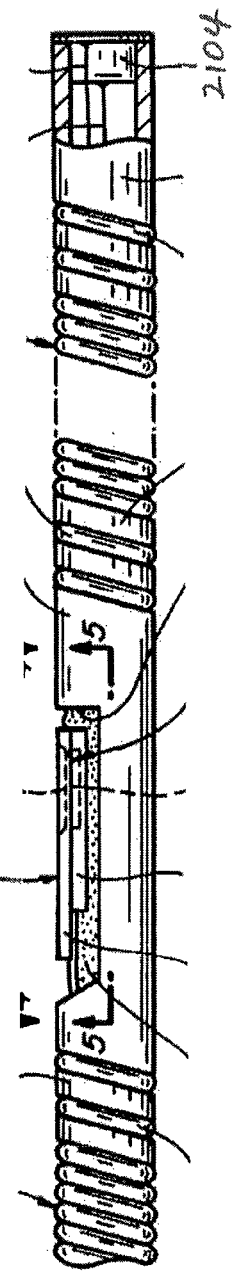

FIGS. 21A-21C illustrate an example of a guidewire 2100 having both a pressure sensor 2102 and an IVUS transducer 2104 located at the distal portion of the guidewire 2100. In some embodiments, the pressure sensor 2102 can be made from a semiconductor material, such as silicon, that is formed into a diaphragm and can be located proximally of the distal tip, while the IVUS transducer 2104 can be located at the distal tip of the guidewire 2104.

In some embodiments, the pressure sensor and/or IVUS transducer can be located on a catheter in a similar configuration to the guidewire. For example, the IVUS transducer can be located on the distal tip of the catheter while the pressure sensor(s) can be located proximally of the IVUS transducer at one or more locations along the catheter body, from the distal portion of the catheter to an intermediate portion of the catheter to the proximal portion of the catheter. The pressure and/or imaging catheter can be used in parallel with the delivery or retrieval device or any other catheter that is inserted into the vasculature. In some embodiments, the pressure and/or imaging catheter can be fastened to the delivery or retrieval device or other catheter by, for example, enclosing both catheters in a sheath or larger catheter or by fusing the two catheters together. For example, U.S. Pat. Nos. 6,645,152 and 6,440,077, both to Jung et al. and hereby incorporated by reference in their entireties for all purposes, discloses an intravascular ultrasound catheter joined together in parallel with a vena cava filter delivery device to guide placement of the filter in the vena cava. The pressure and/or imaging catheter can be used for the same purposes as the pressure and/or imaging guidewire.

FIGS. 22A-22D illustrate two embodiments of an intravascular ultrasound catheter 2200 joined together in parallel with a catheter 2202 that can be used, for example, to deliver a device to a location with the vasculature, such as a vena cava filter to the vena cava. The intravascular ultrasound catheter 2200 can have an IVUS transducer 2204 located on the distal portion of the IVUS catheter 2200. The IVUS transducer 2204 can be a solid state transducer that is disk shaped or cylindrically shaped with a hole to allow passage of a guidewire 2206 or other device through the IVUS catheter 2200. As shown in FIGS. 22A and 22B, the IVUS catheter 2200 and the delivery catheter 2202 can be joined together in parallel without a sheath by adhering or fusing the two catheters together. FIGS. 22C and 22D illustrate the same IVUS catheter 2200 and delivery catheter 2202 fastened together using a sheath 2208.

In some embodiments as illustrated in FIGS. 23A and 23B, the pressure sensor and/or IVUS transducer can be integrated into the delivery or retrieval catheter 2300 or device itself. For example, the IVUS transducer 2302 can be integrated into the distal tip or end of the catheter 2300 or device. The pressure sensor 2304 can be located on a distal portion of the catheter shaft proximally of the IVUS transducer 2302. A wire can extend from the IVUS transducer 2302 and/or pressure sensor 2304 to one or more connectors 2306 located at the proximal end of the catheter 2300. The connector(s) 2306 can be used to connect the IVUS transducer 2302 and/or pressure sensor 2304 to an imaging system and/or processing system. In the illustrated embodiment, the catheter 2300 can be used to deliver a vena cava filter 2308 to the vena cava. The catheter 2300 can additionally have a telescoping sleeve or pusher rod to deploy the vena cava filter 2308, or alternatively, the outer catheter sheath can be retracted to deployed the filter. The IVUS transducer can provide positioning guidance and determine the relative location of the filter by advancing and retracting the IVUS transducer 2302 on the catheter 2300 to generate a plurality of image slices that can be assembled to reconstruct a three dimensional image.

Use of the ultrasound imaging system allows the operator to deliver the device without fluoroscopy or using less fluoroscopy, thereby reducing the radiation exposure to the patient, while allowing more accurate evaluation of the vasculature, aiding placement of the device and allowing confirmation that device placement was proper. The imaging can be used to aid in the deployment of the filters or other devices. The vasculature and implant location can be imaged prior to deployment, after deployment and/or during deployment. The imaging can be used to aid in positioning of the filter or device within the vasculature. The imaging can be used to image the deployment location and determine the appropriate sizing of the filter or other device. The imaging can be used to help estimate treatment duration.

Although an imaging systems described above have been ultrasound based, other imaging systems can be used instead or in addition. For example, the imaging system can be based on intravascular ultrasound (IVUS), Forward-Looking IVUS (FLIVUS), optical coherence tomography (OCT), piezoelectric micro-machined ultrasound traducer (PMUT), and FACT.

In some embodiments as shown in FIG. 24, the pressure sensor(s) and IVUS transducer can be alternatively or additionally added to the delivery catheter. For example, the pressure sensor(s) can be added to one or more locations on the outer sheath and/or the inner sheath of the delivery catheter, while the IVUS transducer 2404 can be added to the distal end of the delivery catheter, at for example, the tracking tip 928 and/or at the distal end of the outer sheath 910.

In some embodiments, a first pressure sensor 2400 can be located distally the distal filter 904 on the guidewire 926 or the tracking tip 928. The first pressure sensor 2400 can be used to measure the pressure within the left common carotid artery 28 downstream of the distal filter 904. As debris 1610 is captured within the distal filter 904, the pores of the distal filter 904 can become clogged, thereby impeding blood flow through the distal filter 904. As the distal filter 904 becomes clogged by debris, the blood pressure downstream of the distal filter 904 can drop. Thus, blood pressure, such as peak systolic pressure or an average pressure over the course of a heartbeat for example, can be continuously monitored by the first pressure sensor 2400, and when a predetermined drop in blood pressure is detected, the operator can be alerted that the distal filter 904 is clogged and should be removed in order to restore blood flow to the brain.

Similarly, a second pressure sensor 2402 can be located on the outer sheath 910, such that when the outer sheath 910 is retracted to deploy the proximal filter 902, the second pressure sensor 2402 is located downstream of the proximal filter 902 and can measure the pressure in the brachiocephalic trunk 22 or right subclavian artery 24, depending on the location of the second pressure sensor 2402. As the proximal filter 902 becomes clogged by debris 1610, the blood pressure downstream of the proximal filter 902 can drop. Thus, blood pressure, such as peak systolic pressure or an average pressure over the course of a heartbeat for example, can be continuously monitored by the second pressure sensor 2402, and when a predetermined drop in blood pressure is detected, the operator can be alerted that the proximal filter 902 is clogged and should be removed in order to restore blood flow to the brain.

In some embodiments, when at least one filter is determined to be clogged, the operator is instructed to recover and remove both filters from the patient. A new distal protection device with clean filters can then be redeployed into the patient. In other embodiments, when both filters are determined to be clogged, the operator is instructed to recover and remove both filters from the patient, and a new distal protection device with clean filters can then be redeployed into the patient.

In some embodiments, a third pressure sensor 2403 can be located on the inner sheath 908 between the proximal filter 902 and the distal filter 904 such that the third pressure sensor 2403 is located within the aortic arch when the two filters are deployed. In some embodiments, additional pressure sensors 2405, 2406 can be located on the inner sheath just upstream of the opening to the filters in order to determine the pressure drop across each filter. In some embodiments, the pressure drop across each filter can be estimated by subtracting the pressures measured downstream of the filters from the pressure measured in the aortic arch. In some embodiments, additional pressure sensors 2407, 2408 can be located on the portion of the inner sheath that lies within each filter. In some embodiments, instead of placing or integrating pressure sensors within the sheaths, the inner and/or outer sheaths can have pressure measuring ports that allow a guidewire having a plurality of pressure sensors to measure the pressure along various locations as described above. The pressure measuring ports can provide fluid communication from the exterior of the sheaths to the guidewire that is disposed within the sheath.

Figure 25A:
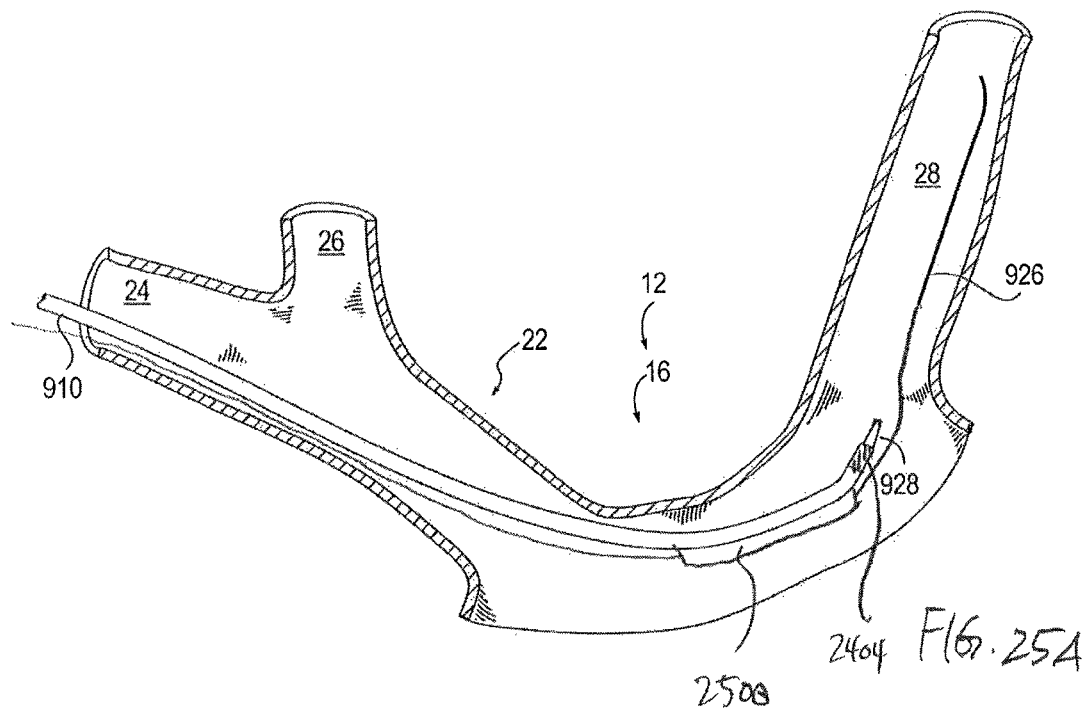
FIGS. 25A-25C illustrates an embodiment of a distal protection filtering device having a rapid exchange guidewire lumen for receiving a guidewire having one or more pressure sensors.
Figure 25B:
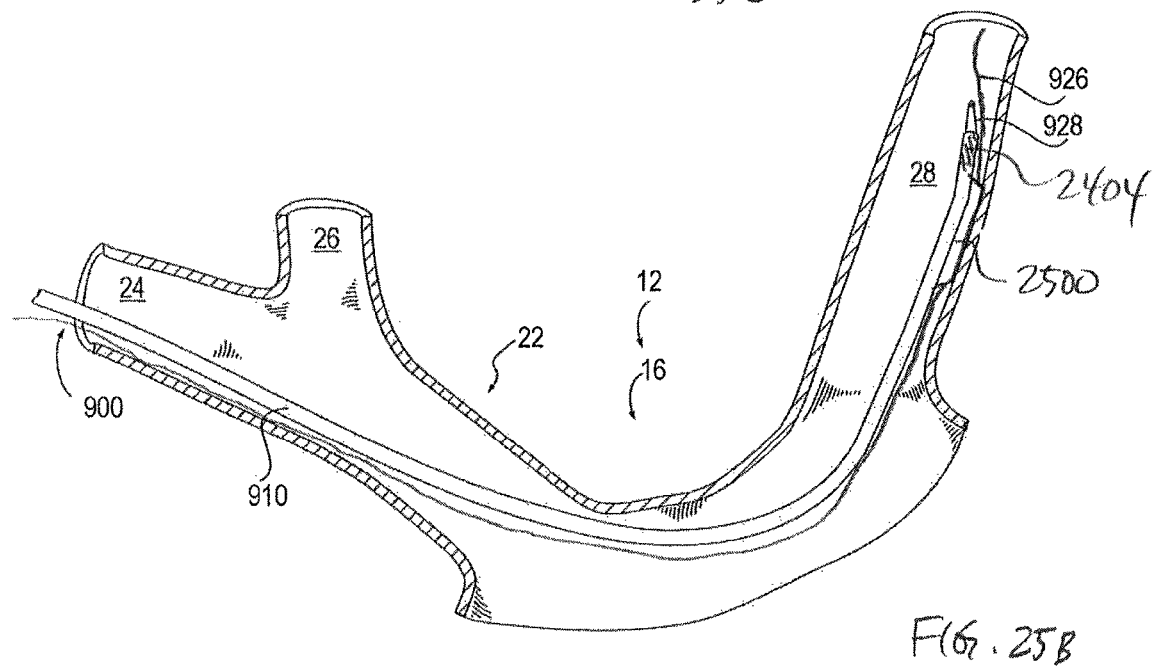
Figure 25C:
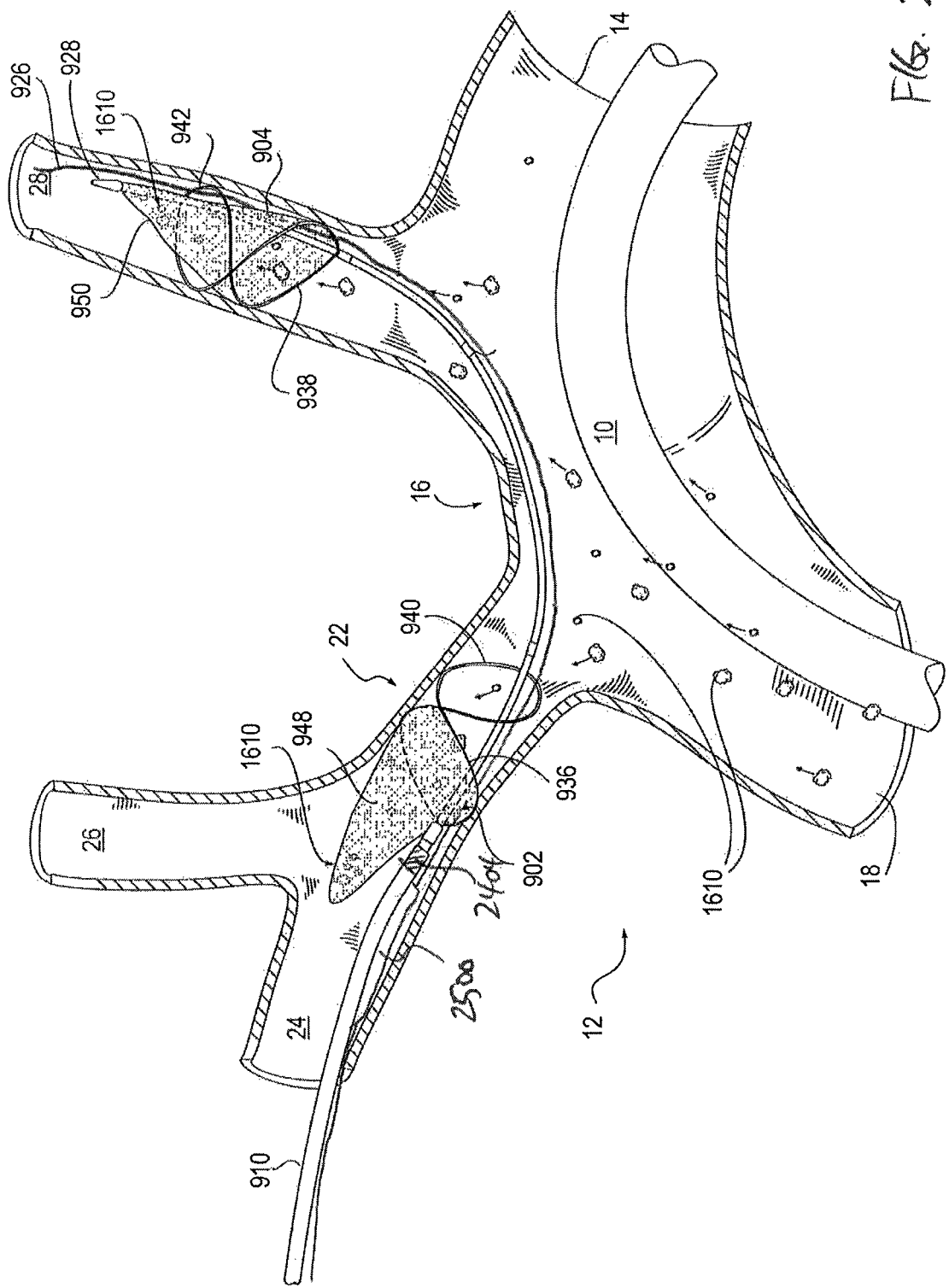

In some embodiments, as illustrated in FIGS. 25A-25C, the outer sheath 910 can have a rapid exchange guidewire lumen 2500 for receiving the guidewire 926 in a rapid exchange configuration. The rapid exchange guidewire lumen 2500 can be located along a distal portion of the outer sheath 910 in parallel to the main outer sheath lumen. In some embodiments, the length of the rapid exchange guidewire lumen 2500 is greater than about 6 cm. In other embodiments, the length of the rapid exchange guidewire lumen 2500 is less than about 6 cm. In some embodiments, the distal end of the rapid exchange guidewire lumen 2500 is located proximally of the IVUS transducer 2404 located at the distal end of the outer sheath 910. In some embodiments, particularly in embodiments having the rapid exchange guidewire lumen, the inner sheath on which the distal filter 904 is attached to can instead be a wire, guidewire or elongate member without a lumen. Replacing the inner sheath with a wire allows the profile of the distal protection device to be reduced, thereby facilitating minimally invasive insertion and reducing the potential to cause obstructions within the aortic arch. Using the rapid exchange guidewire lumen 2500 allows the distal portion of the guidewire 926 to be exposed directly to the blood as the outer sheath 910 is retracted to deploy the filters. This allows placement of a plurality of pressure sensors on the guidewire 926 instead of on the inner and/or outer sheaths. The placement of the pressure sensors on the guidewire 926 can correspond to all the positions described above, allowing the pressure across each filter to be determined. In some embodiments, the guidewire 926 can have an alignment feature to align the pressure sensors to the desired locations relative to the deployed filters. For example, the guidewire can have a radiopaque marker and/or echogenic marker that can be aligned with a corresponding radiopaque marker and/or echogenic marker on the outer sheath, inner sheath, and/or tracking tip. In some embodiments, the rapid exchange guidewire lumen can be located on the distal portion of the inner sheath that extends beyond the distal end of the outer sheath when the filters are in the loaded configuration. In addition, if one or more of the distal protection filters is determined to be clogged, use of the rapid exchange guidewire lumen facilitates the exchange of a clogged distal protection device with a new, unclogged distal protection device. In some embodiments, the guidewire can be retracted proximally of the distal protection filters before or after the filters are deployed, in order to reduce the risk that the guidewire interferes with apposition of the filter against the vessel wall. In other embodiments, the guidewire can be left in place and the filters can still expand and achieve wall apposition by pushing the guidewire against the vessel wall.

The IVUS transducer 2404 can be used to provide image based navigation of the delivery catheter through the vasculature to the deployment locations in the left common carotid and brachiocephalic trunk, for example. In addition, the IVUS transducer 2404 can be used to visualize deployment of the filters within the target locations and verify proper deployment including complete wall apposition of each filter within the target locations. As mentioned above, the IVUS transducer 2404 can be added to the distal end of the outer sheath 910. As the outer sheath 910 is retracted to deploy the filters 902, 904, the IVUS transducer 2404 can be used to image the filters 902, 904 as they are being deployed, allowing the operator to verify proper deployment of each filter. If imaging reveals improper deployment, the filters can be recaptured within the outer sheath by advancing the outer sheath back over the filters and then redeploying the filters.

To improve visualization of the filters using IVUS imaging, echogenic materials and/or features can be incorporated into various components of the filters including the filter frame and/or the material capture structure. The echogenic materials and/or features can be incorporated throughout the filter components or at discrete locations on the filter as more fully described below.

Filters are more complex structures in contrast to the relatively simple designs found in catheters and needles. In a more complex device like a filter there is a need to identify specific portions within the device during some medical procedures. In addition, it would be advantageous as well to determine the orientation of the device including components within the device to one another (as used for determining deployment, retrieval and the various intermediate stages thereof) as well as the overall filter orientation to the surrounding lumen or vessel. In contrast to the conventional techniques using location of the tip or start or end of the entire length, a more complex structure such as a filter position, orientation or relative placement information would yield specific benefits. In some cases, aspects, portions or attributes of the overall filter or filter components or portions will enable more useful determinations about the filter in relation to the physiological environment. In one aspect, an intravascular ultrasound (IVUS) catheter and processing system or signal processing algorithm is used to confirm filter sizing selection, guidance for filter placement, filter implantation steps, filter and/or vessel measuring using IVUS before during and/or after steps to confirm sizing selection and fit is appropriate under the physiologic environment and for confirmation and/or documentation of proper sizing selection, placement, engagement or degree of engagement of fixation elements (if present), clot burden, orientation and/or deployment in a patient or physician medical record.

In one aspect, embodiments of the present invention are directed toward medical devices having a complex shape or that are configured to move from stowed to deployed configurations that may also have specific orientation and placement criteria for proper use in a lumen, vessel or hollow organ. One such complex device is an IVC filter. Aspects of the present invention include such devices employed within the human body which have enhanced ultrasound visibility by virtue of incorporation of an echogenic material using any of the techniques described herein alone or in any combination.

In one aspect, there are described herein various alternative filter designs for increasing the echogenicity of the filter.

A filter with enhanced echogenic characteristics may include one or more than one of: (a) a modification to one or more components of the filter to enhance the echogenic characteristics of the component; (b) formation of dimples into a component surface of sufficient number and scaled to a suitable size, shape, orientation and pattern for use with intravascular ultrasound systems; (c) protrusions formed in, placed on or joined to a filter surface; (d) roughening one or more surfaces of a filter, for example using a chemical process, a laser or bead blasting technique; and (e) altering one or more steps of a filter manufacturing technique to introduce cavities, voids or pockets to locally modify or adapt one or more acoustic reflection characteristics to improve echogenicity in one or more specific regions of a filter. One example of the manufacturing alteration is to introduce gaps between the segments of tubing or coverings whereby the gap provides the echogenic enhancement. In addition, cavities, voids, pockets, dimples, gaps and the like may be left empty or, optionally, filed, partially filed or lined with any of the echogenic materials described herein.

In one aspect, there are provided embodiments of a filter having enhanced echogenic characteristics in or related to at least one or a portion of: an proximal end, a distal end, a terminal proximal end, a terminal distal end, a retrieval feature, an atraumatic tip on a retrieval feature, a mid-strut region, a leg or strut portion having at least one orientation attribute to another portion of the filter, an indicia of a location of a fixation element or a retrieval feature, a location on a portion of the filter selected such that in use with a particular fixation element the marker in a location that indicates that the fixation element is fully deployed into a wall of a lumen or portion of a vessel or hollow organ (i.e., the marker is against the lumen wall or nearly so when the fixation element is fully engaged. As such, see the marker against the wall indicates proper deployment, spaced from or not visible would indicate, respectively, not fully engaged or over penetration); a portion of the distal tip and/or an elongated portion. The above described methods may also be applied to the other techniques and alternatives described herein.

In still further embodiments, a portion, component or aspect of an intraluminal filter may have enhanced echogenic attributes by applying a coating or sleeve containing one or more of the echogenic materials disclosed herein or fabricated according to any of the techniques or having any of the attributes to enhance echogenic qualities as described herein. In some aspects, the enhanced echogenic attributes are provided by the incorporation into, application onto or within a component or portion of a filter one or more echogenic materials or echogenic markers in a specific configuration, location, orientation or pattern on the filter.

Enhanced echogenic markers or locations may be devised and placed for use individually or in combinations such as to facilitate the identification to an IVUS system or ultrasound imaging modality an indication or signature for a specific location on a filter, such as, for example, a retrieval feature, a terminal proximal end, a terminal distal end, a location of a fixation element or a location of some other indicia that identifies a specific aspect of a particular filter design. In addition or alternatively, two or more enhanced echogenic markers or portions may be used in combination to provide additional information about a filter such as orientation with in a vessel, confirmation of deployment or a portion of a deployment sequence, confirmation of final placement, confirmation of migration or lack of migration, confirmation of retrieval or progress in a retrieval sequence and the like according to the various processes and used for filters within the vasculature or in lumens of the body. In another specific embodiment, the use of IVUS techniques with embodiment of the echogenic enhanced filters describe herein may also be used to measure the diameter of the vessel at specific device locations indicated by the echogenic markers during or after deployment or retrieval of a filter.

In still further aspects, the use of IVUS techniques with embodiment of the echogenic enhanced filters describe herein may also be used to determine, detect or indicate inadequate dilation, adequate dilation, filter expansion, degree of filter expansion, filter-vessel engagement and degree or engagement, strut/leg/anchor position and other attributes relating to the interaction between the filter and the surrounding physiological environment.

Still further, the echogenic markers are positioned with regard to the likely or planned positioning of the IVUS transducer and/or likely pathways for acoustic energy used by the imaging system. By way of example, if the IVUS transducer is forward looking, then those forward looking aspects of the filter will be provided with the enhanced echogenic aspects. In another example, if the IVUS transducer is cylindrically shaped and will be positioned through the interior portion of a filter then the filter will be provided with enhanced echogenic aspects on interior surfaces or portions that would receive acoustic energy from such as transducer in such a position. Other modifications are within the scope of the invention based on the particular style of IVUS transducer used, the position relative to the filter and the placement and type of echogenic feature incorporated into the filter. Put another way, the echogenic enhancements of the filters described herein are selected, designed and positioned on the filter with regard to the IVUS sensor type, acquisition mode and position relative to the filter. Additional details in the use of IVUS with filters is further described in U.S. Pat. Nos. 6,645,152 and 6,440,077, both of which are incorporated herein by reference in their entirety for all purposes.

In one aspect, the placement and signature of such enhanced echogenic markers are discernible to a human user viewing an ultrasound output alone or in combination with being discernible to a computer system configured for the processing of an ultrasound return including a return from the enhanced echogenic filter. Additional aspects of the formation and use of echogenic materials is made with reference to the following US Patents and Patent Publications, each of which is incorporated herein by reference in its entirety: US 2010/0130963; US 2004/0230119; U.S. Pat. Nos. 5,327,891; 5,921,933; 5,081,997; 5,289,831; 5,201,314; 4,276,885; 4,572,203; 4,718,433; 4,442,843; 4,401,124; 4,265,251; 4,466,442; and 4,718,433.

In various alternatives, the echogenic material may either be applied to a portion of or a component of a filter in any of a number of different techniques.

In one example, an echogenic component or additive is applied to or incorporated into a filter or portion of a filter as a selective coating applied to a portion or component of a filter.

In one example, an echogenic component or additive is applied to or incorporated into a filter or portion of a filter as a mold formed to be placed over or joined to a portion of component of a filter.

In one example, an echogenic component or additive is applied to or incorporated into a filter or portion of a filter as an extruded sleeve formed in a continuous segment to cover a portion or component of a filter. In one embodiment, one of the inner tubular member or the outer sleeve or coating may be fabricated of a material according to the present invention, having increased echogenicity, with the other of the inner tubular member fabricated of a biocompatible polymer such as polyurethane or silicone rubber, for example.

In one example, an echogenic component or additive is applied to or incorporated into a filter or portion of a filter as a compound or two layer structure comprising an inner tube and an outer tube or sleeve with one or both of the tubes made from or including or incorporating one or more echogenic materials or modifications as described herein. In addition or alternatively one or both sleeves, tubes described herein may include or encapsulate an echogenic marker or component of specific shape or geometry, for example, as in the case of a tube structure having within the sidewall of the tubing a coiled structure. In one aspect, the coiled structure is made from an echogenic material and the windings are provided in a manner that is useful in any of the aspects of the filter described herein. The coil may have a particular size or variation in size, pitch or variation in pitch or other attribute useful in providing an echo identifiable aspect of the filter property being determined. In one specific embodiment, the dimensions of the coil or other echogenic material has dimensions selected for increasing acoustic reflection with regard to the resolution or processing algorithms used in the imaging ultrasound system.

In one example, an echogenic component or additive is applied to or incorporated into a filter or portion of a filter as a braided structure incorporated into a compound or two layer structure comprising an inner tube and an outer tube or sleeve with one or both of the tubes made from or including or incorporating one or more braid comprising echogenic materials or modifications as described herein. In addition or alternatively one or both sleeves, tubes described herein may include or encapsulate an braid formed into an echogenic marker or component of specific shape or geometry, for example, as in the case of a tube structure having within the sidewall of the tubing a braided structure. In one aspect, the braided structure is made from an echogenic material and the braided is a small diameter that is when wound around the tubes or sleeve or directly onto a portion of or component of a filter. The winding pattern and spacing of the braided materials are provided in a manner that is useful in any of the aspects of the filter described herein. The braid may have a particular braid strand composition, structure, size or variation in size, pitch or variation in pitch or other attribute useful in providing an echo identifiable aspect of the filter property being determined. One or more of the strands in the braid may be formed from an echogenic material. One or more of the strands may be formed from a material having improved radiopaque characteristic. One or more of the strands may be formed from a material having both echogenic and radiopaque properties. The strands of a braid may be combined using any of the above described strand characteristics.

In another alternative, in still another example, an echogenic component or additive is applied to or incorporated into a filter or portion of a filter as the a series of short segments placed adjacent to one another along a portion or component of a filter in either a close packed or spaced arrangement. In another embodiment, the spacing or voids between adjacent segments may also be adjusted or selected so as to enhance echogenic capabilities of the filter using the material difference introduced by the spacings or voids.

In another alternative, in still another example, an echogenic component or additive is applied to or incorporated into a filter or portion of a filter as a tubing or sleeve suited to heat shrink operations. In one aspect, there is a manufacturing or assembly steps of sliding one or more sleeves over portion of the filter then apply heat to shrink down the segment about the portion of the filter. In particular, various embodiments provide for the specific placement of such a shrink fit tubing having enhanced echogenic characteristics as described herein. It is to be appreciated that the sleeves, segment or tubes may be provided from or have echogenic modifications or elements incorporated into suitable materials such as, for example, ePTFE, PTFe, PET, PVDF, PFA, FEP and other suitable polymers. Still further, these and other materials may be formed in shapes other than tubes but may also take the form of strands, lines, fibers and filaments to be applied in accordance with the echogenic enhancement techniques described herein. In some embodiments, the tubes or segments applied to a filter may have the same or different composition as well as have the same width or different widths. In one aspect, the width or thickness of a plurality of bands is used to provide a code or information about the filter. The use of echogenic bands of different widths is a marking technique similar to the way that different size and color rings on a resistor are arranged in a pattern to describe the resistor's value.

In another alternative, in still another example, an echogenic component or additive is applied to or incorporated into a filter or portion of a filter is extruded over a portion of or a component of the filter.

In another alternative, in still another example, an echogenic component or additive is applied to or incorporated into a filter or portion of a filter is by bonding an echogenic material or components to the filter using a suitable adhesive or bonding technique.

In any of the above described configurations, the portion or component of the filter may be modified with dimples, grooves, pockets, voids. In other aspects, there may be one or more full or partial circumferential recesses, rings, surface diffraction gratings or other surface features to selectively enhance or provide an echogenic property in that portion of the filter, to aid in or foster the application of the echogenic materials. In still further aspects, any of above described surface modifications may also be used to uniquely identify a portion of a filter or any of the above in any combination.

In still further aspects of any of the above echogenic markers or attributes the thickness of the sleeve or coating or component may decrease at its proximal and distal ends to provide for a smooth outer surface. As yet an additional alternative, a coating, marker or other echogenic material may extend proximally to or closely adjacent to the distal end or the distal end or both of the filter component or filtering device.

In still other alternatives or combinations, some filter design embodiments alter components of the filter to enhance echogenicity such as, for example, material selection to incorporate echogenic materials. Examples of echogenic materials include palladium, palladium-iridium or other alloys of echogenic materials.

In some embodiments, echogenic microbubbles are provided in a portion of a filter to enhance the acoustic reflections of that aspect of the filter. Echogenic microbubbles may be prepared by any convenient means and introduced into the component or portion thereof or by a coating or sleeve or shell or other transferring means or mixed with a polymer or other suitable base compound prior to extension of extrusion, molding casting or other technique. The echogenic microbubbles may be pre-prepared or prepared inside the component or element or marker as appropriate. Aspects of the preparation or use of microbubbles are described in U.S. Pat. Nos. 5,327,891; 4,265,251; 4,442,843; 4,466,442; 4,276,885; 4,572,203; 4,718,433 and 4,442,843. By way of example, echogenic microbubbles can be obtained by introducing a gas, e.g. carbon dioxide, into a viscous sugar solution at a temperature above the crystallization temperature of the sugar, followed by cooling and entrapment of the gas in the sugar crystals. Microbubbles can be formed in gelatin and introduced into a component or portion of a device. Microbubbles can also be produced by mixing a surfactant, viscous liquid and gas bubbles or gas forming compound, e.g. carbonic acid salt, under conditions where microbubbles are formed.

In still further alternatives, there is also the incorporation of dual mode materials (radiopaque and echogenic) into a polymer then used to form part of, be applied or otherwise incorporated with a filter device as described herein. Some of these polymer compounds may be fabricated to enhance aging and shelf life and have other beneficial attributes. In one aspect, a filter or portion thereof includes one or more selected segments that are constructed using visibility materials compounded with one or more polymeric materials that make the selected segments visible using both fluoroscopy and ultrasonic imaging. In one specific example, the visibility material may take the form of tungsten and/or tungsten carbide particles dispersed within a polymeric material. In one specific aspect, the radiopaque and echogenic material includes tungsten and/or tungsten carbide particles distributed within a base polymeric material.

In one embodiment, a portion of or a component of a filter includes or has been modified to have an inner layer including a radiopaque and echogenic material. In one alternative, the radiopaque and echo genic material includes particles distributed within a base polymeric material (i.e., a first polymeric material) including a polyether block amide; and an outer layer including an additional polymeric material (i.e., a second polymeric material). In certain embodiments, the additional polymeric material is a thermoplastic elastomer. Optionally, the additional polymeric material is more resistant to hydrolysis and/or oxidation than the base polymeric material.

In still further aspects, a component, a portion or an element added to a filter may be regarded as an echogenic body member that is a part of an echogenic filter to be sonically imaged. The echogenic body member is at least partially made up of a composite material which is echogenically imageable in the patient, such as by the use of ultrasonic imaging equipment used either within the patient or external to the patient. In one aspect, a composite material includes matrix material with discrete acoustic reflective particles embedded in matrix material. In one aspect, the matrix material is a biocompatible plastic. Examples of suitable plastics may include urethane, ethylene, silicone, polyethylene, tetrafluoroethylene. In one aspect, a matrix is a formable, pliable material which may be molded and/or extruded to a variety of shapes, depending upon a specific application. The sound reflective particles are embedded in matrix material. Particles are, by way of example, made of a hard material, such as small glass particles that are solid or filled with an acoustically reflective medium. In one aspect, glass particles having a generally spherical shape forming glass microspheres. Glass microspheres with an outer diameter of about 5 microns is one acceptable size. Other sized particles may be utilized as, for example, ranging between 1 and 50 microns and beyond. Particles sized below the resolution size of the imaging ultrasound system in use may be arranged into patterns of sufficient size and orientation to the acoustic waves that result in a discernible feature by the imaging ultrasound system. Furthermore, the particles do not necessarily have to be spherical, or may be partially spherical. Still further, the shape of the particle could be altered to enhance acoustic reflection by presenting different shapes of particles, sizes of particles and combinations thereof to modify acoustic characteristics of the matrix material. By way of example, the particles may be shaped into an "Ordered array." "Ordered arrays" can take the form of a macrostructure from individual parts that may be patterned or unpatterned in the form of spheres, colloids, beads, ovals, squares, rectangles, fibers, wires, rods, shells, thin films, or planar surface. In contrast, a "disordered array" lacks substantial macrostructure.

By way of example, an echogenic marker may comprise particles that individually are below the resolution of the imaging ultrasound system. The echogenic marker is the combination of these below imaging ultrasound resolution particles in combination, in 1D, 2D or 3D patterns, in graphic arrays, or in machine readable combinations to make a signature. Based on the specific characteristics of the combination of particles, the acoustic returns from an echogenic marker or combination of echogenic markers may be visually perceptible in a display for interpretation by a user or may be detected and interpreted by one or more acoustic reflection or spectral processing algorithms within a imaging ultrasound processing system.

In one aspect, the echogenic material is fabricated by incorporating nanometer sized particles of sonically reflective materials, for example iron oxide, titanium oxide or zinc oxide into a biocompatible polymer. In one method of fabrication, the acoustically reflective particles are mixed with a powdered thermoplastic or thermosetting material such as a polyether amide, a polyurethane or an epoxy, or polyvinylchloride followed by thermal processing of the mixture to provide a material of increased sonic reflectance which may be applied as a coating on medical devices of the type discussed above or may be incorporated as a structural component of the medical devices as described herein.

In still further embodiments and aspects, the particles included to provide echogenic enhancements may be selected, arranged or incorporated to provide acoustically geometrically tuned nanostructures, microstructures or macrostructures. The particles provided herein are formable in all shapes currently known or to be created for acoustic reflection enhancement. In non-limiting examples, the nano-, micro- or macro-particles are shaped as spheres, ovals, cylinders, squares, rectangles, rods, stars, tubes, pyramids, stars, prisms, triangles, branches, plates or comprised of an acoustically reflective surface or where one or more surfaces is adapted such as by roughening or dimpling or other technique used to alter acoustic reflection properties. In non-limiting examples, the particles comprise shapes and properties such as plates, solid shells, hollow shells, rods, rice shaped, spheres, fibers, wires, pyramids, prisms, or a combination thereof.

In one specific aspect, a partially spherical surface may be provided on the outside and/or the inside of particles, as for example a particle with a hollow spherical space therein. Particles are made up of a different material than the matrix. While desiring not to be bound by theory, it is believed that a spherical shape provides for sound reflections at a variety of angles regardless of the direction from which the ultrasonic sound waves are emanating from, and accordingly, are more likely to reflect at least a portion of the transmitted signal back to the ultrasonic receiver to generate an image. Since many of matrix materials available are relatively ultrasonically transparent in a patient, sound reflective particles provide adequate reflection. The use of a composite, rather than a solution, provides adequate size for acoustic reflection off of the discrete particles embedded in the matrix. As indicated, a variety of materials may be utilized for the sound reflective particles, such as aluminum, hard plastic ceramics, and, metal and/or metal alloys particles, and the like. Additionally, liquids, gases, gels, microencapsulants, and/or suspensions in the matrix may alternatively be used either alone or in combination, so long as they form a composite with the desired ultrasonically reflective characteristic.

Any of the above embodiments, alternatives or filter modifications to enhance echogenic characteristics may also be designed or implemented in such a way as to provide an echogenic identifiable or unique trait or acoustic reflection signature that may be registered by a human operator looking at a display or identified using signal processing techniques of a return containing acoustic reflections from the filter in an imaging ultrasound system. In one example, there is a surface of the filter having one or more echo registerable or identifiable feature, mark or indication in a position useful for determining one or more of: a location of an end of a filter; a location of a fixation element on a filter; a location of a retrieval feature on a filter, an orientation of one or more of a leg, a strut, a filter or an end of a filter relative to another of a leg, a strut, a filter or an end or the orientation of the overall filter to a lumen, vessel or hollow organ in a body. Moreover, in another widely applicable aspect of providing enhanced imaging characteristics to a filter as described herein, the characteristic or modification—however added or incorporated into the filter—enable a filter, a filter component or a specified portion of a filter to be more readily imaged by intravascular ultrasound as described herein. In still another aspect, the characteristics or modification to the filter are oriented and positioned in order to facilitate IVUS imaging via an IVUS probe borne by a filter deployment or retrieval catheter, snare, or other implement provided to facilitate the use of intravascular filters.

Figure 26:
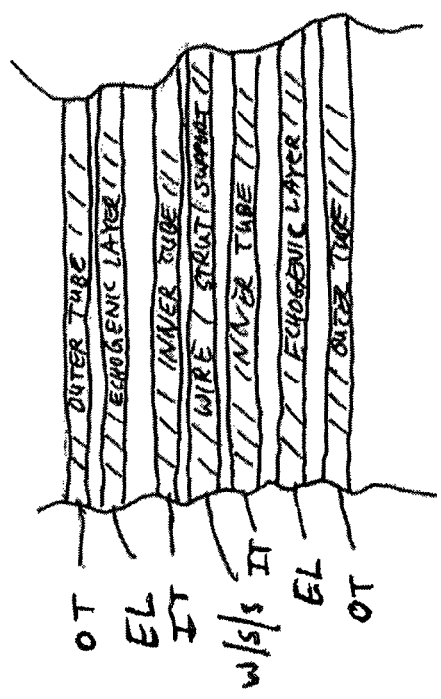
FIG. 26 is a section view of a wire strut or support element of a filter (w/s/s) having multiple segments in a concentric arrangement.

FIG. 26 is a section view of a wire strut or support element of a filter (w/s/s) having multiple segments in a concentric arrangement. In this illustrative embodiment, the wire is encased in alternating tube segments. There is an inner tube (IT) directly adjacent to the wire. There is an echogenic segment layer (EL) adjacent to the inner layer. The inner tube may be selected to act as bonding layer to increase adhesion between the echogenic layer and the filter wire, strut or support member. In this embodiment, there is an outer tube (OT) over the echogenic layer. In alternative configurations, either or both of the inner tube or the outer tube may be omitted. The echogenic layer is a segment having one or more of the echogenic characteristics described herein.

FIGS. 27-32 provide various exemplary embodiments of a segment 87 having one or a plurality of one or more than one type of echogenic characteristic, property or feature added thereto. Each of the illustrated echogenic adaptations applied to segment 87 along with segment 87 itself may be sized, scaled and/or shaped as described herein as needed based upon the requirements of the portion of the filter and the echogenic characteristic.

Figure 27:
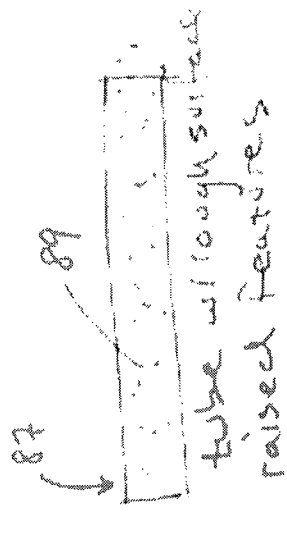
FIG. 27 is an embodiment of a segment having one or a plurality of laser drilled holes formed therein.

FIG. 27 is an embodiment of a segment 87 having one or a plurality of laser drilled holes 88 formed therein. The diameter and the shape of the holes may be selected based upon the size of the filter or filter component to which the segment 87 will be attached. The holes 88 may be completely through the wall of the segment or only partially through the wall. The holes 88 may be formed in any pattern, spacing or orientation as described herein.

Figure 28:
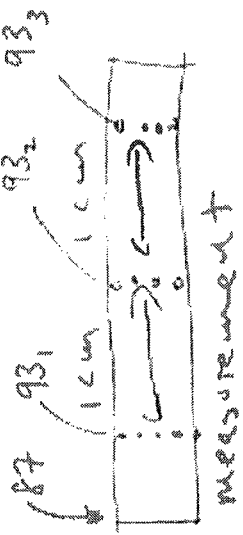
FIG. 28 is an embodiment of a segment having one or a plurality of raised features or alternatively roughed portions formed thereon.

FIG. 28 is an embodiment of a segment 87 having one or a plurality of raised features or alternatively roughed portions 89 formed thereon. The size and shape of the raised features or the roughness of the surface may be selected based upon the size of the filter or filter component to which the segment 87 will be attached. The raised features or portions of roughness 89 may be formed in any pattern, spacing or orientation as described herein.

Figure 29:
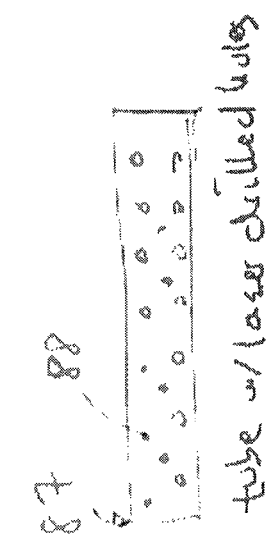
FIG. 29 is an embodiment of a segment having one or a plurality of bubbles formed therein.

FIG. 29 is an embodiment of a segment 87 having one or a plurality of bubbles 90 formed therein. The size, shape, pattern, and manner of incorporating one bubble 90 or a plurality of bubbles 90 into the segment 87 may be selected based upon the size of the filter or filter component to which the segment 87 will be attached. The bubbles 90 may be formed within the segment sidewall, near the surface of the segment sidewall or near the inner surface of the sidewall. The bubble or bubbles 90 may be formed in any pattern, spacing or orientation as described herein.

Figure 30:
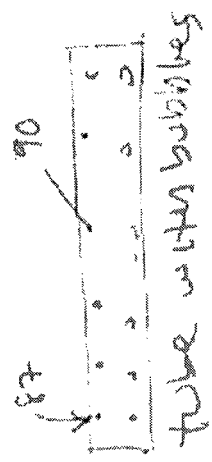
FIG. 30 is an embodiment of a segment having one or a plurality of dimples formed therein.

FIG. 30 is an embodiment of a segment 87 having one or a plurality of dimples 91 formed therein. The diameter and the shape of the dimples may be selected based upon the size of the filter or filter component to which the segment 87 will be attached. The dimples 91 may be formed in any pattern, spacing or orientation as described herein.

Figure 31:
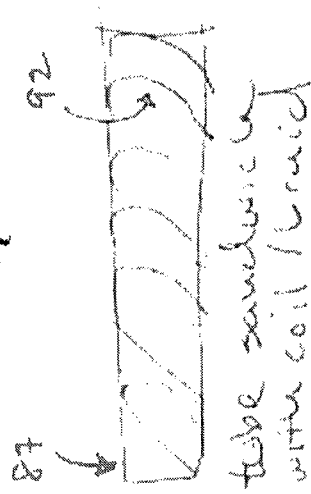
FIG. 31 is an embodiment of a segment having a coil or braided structure within or about the segment.

FIG. 31 is an embodiment of a segment 87 having a coil or braided structure 92 within or about the segment 87. The size, shape, pattern, and manner of incorporating the coil or braid 92 into the segment 87 may be selected based upon the size of the filter or filter component to which the segment 87 will be attached. The coil or braid 92 may be formed within the segment sidewall, near the surface of the segment sidewall or near the inner surface of the sidewall. The coil or braid 92 may be part of a sandwich structure as illustrated and described in FIG. A. The coil or braid 92 may be formed in any pattern, spacing or orientation as described herein to enhance the echogenic characteristics of the filter or filter portion attached to the segment 87. The coil or braid 92 may be continuous along the entire length of a segment 87 or, alternatively, the coil or braid 92 may be in short lengths selected so that a plurality of coils or braids are provided within a single segment 87.

Figure 32:
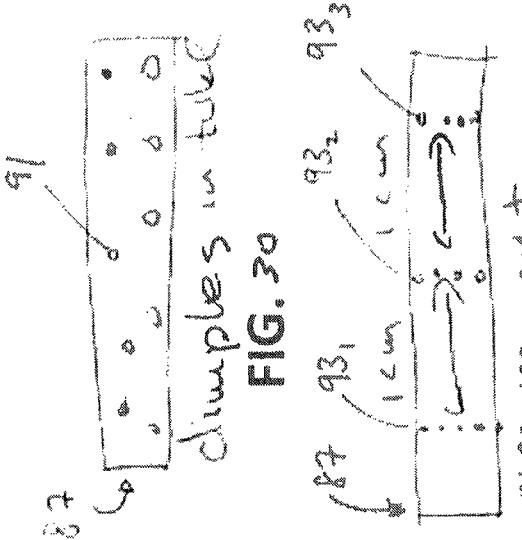
FIG. 32 is an embodiment of a segment having a plurality of echogenic markers arrayed in rings about the segment to provide an indication of measurement via the spacing between adjacent rings.

FIG. 32 is an embodiment of a segment 87 having a plurality of echogenic markers 93 arrayed in rings 93.1, 93.2 and 93.3. For purposes of illustration the rings are shown in an orientation that is generally orthogonal to the central longitudinal axis of the segment 87. The rings are shown with a sample spacing of 1 cm between them. The spacing may be any suitable distance based on the factors described herein such as filter size and physiological environment. Similarly, the rings may be angled in other orientations relative to the longitudinal axis of the segment. For example, some ring may be in one angular orientation while other rings may be in a different angular orientation where the angular orientation or patent of orientation is utilized to provide one or more of the filter functionality or echogenic characteristics described herein. In some specific configurations, the spacing and sizes used are in the millimeter range. In some specific configurations, the spacing and sizes are in the micron range. In some specific configurations, the size and/or spacing of a ring or between adjacent rings are in a combination of mm and micron ranges for sizes, spacings and features. The size and spacing of the echogenic markers 93 may be selected based upon the size of the filter or filter component to which the segment 87 will be attached. The markers 93 may be formed in any pattern, spacing or orientation as described herein in order to facilitate a measurement using the markers. Still further, the markers 93.1, 93.2 and 93.3 may be utilized for provide for other filter characteristics as described herein.

Figure 33:
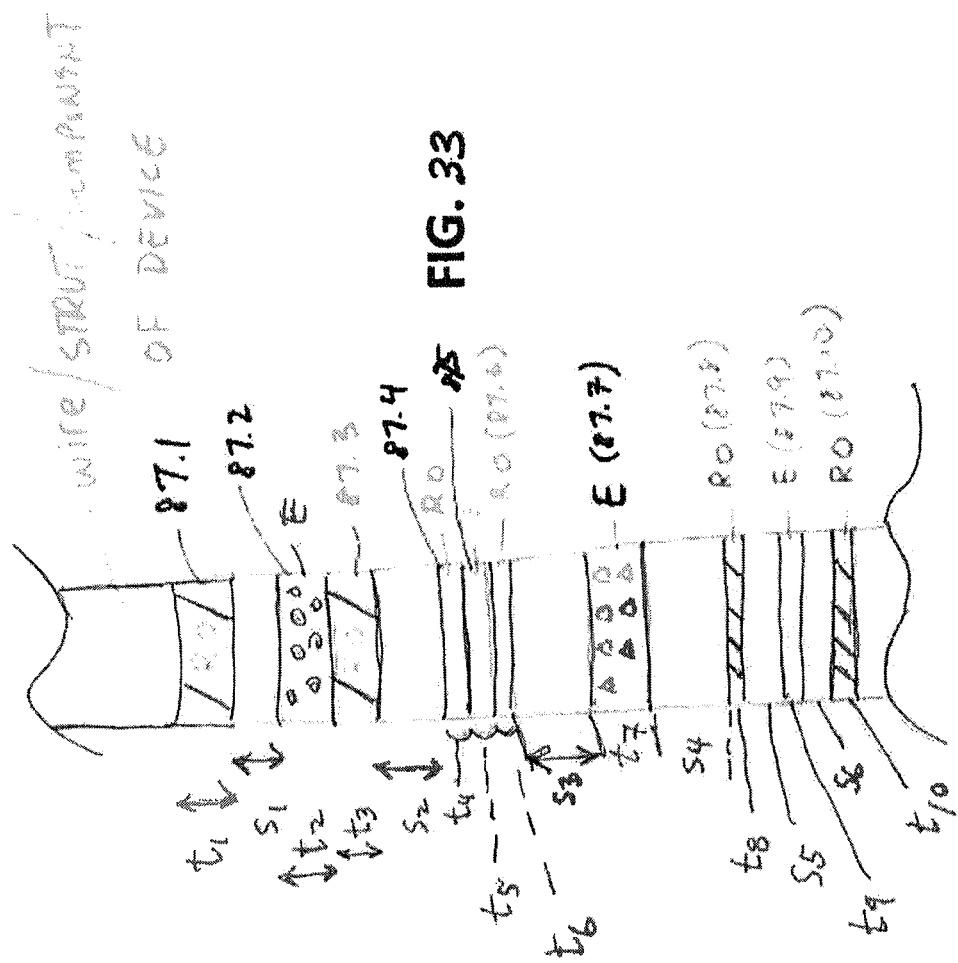
FIG. 33 illustrates various alternative configurations for a segment used alone or in conjunction with other segments.

FIG. 33 illustrates various alternative configurations for a segment used alone or in conjunction with other segments. The segments are illustrated along an exemplary wire, strut, or component of a filtering device. The segments may have different characteristics to enable the segment to be more readily imaged by a medical imaging modality used externally, internally or intraluminally. In one aspect, the segment characteristics are selected to provide for imaging enhancements for a filter being used within a vein or an artery. In another aspect, the segments may have different characteristics to enable the segment to be readily imaged by intravascular ultrasound as described herein. In still another aspect, the segments are oriented and positioned in order to facilitate IVUS imaging via an IVUS probe borne by a filter deployment or retrieval catheter, snare, or other implement. In one illustrative embodiment, the segments are selected and arrayed to facilitate imaging utilizing IVUS and an external medical imaging modality. In one exemplary embodiment, the external imaging modality is x-ray.

Also illustrated in FIG. 33 is the use of a combination of different echogenic characteristics (designated E) and radio-opaque characteristics (designated RO). These characteristics may be any of those described herein in any combination. The echogenic characteristic of a segment may be the same as another segment in a grouping such as in the E segments 87.9 and 87.5. Alternatively, the echogenic characteristic of a segment may be different from those in an adjacent group as with segments 87.2, 87.5 and 87.7.

FIG. 33 also illustrates not only that different characteristic and properties of segments may be used but also how variable segment dimensions may be used to aid in echogenic enhancement of a filter. As illustrated, the segments have different widths or thicknesses as indicated along the longitudinal axis of the wire, strut or component. As such, FIG. 33 illustrates a series of imagine enhancing segments 87.1-87.10 having a variety of width or thickness values t1-t10. In one embodiment, the segments are configured as short rings or bands. The thickness of segments in groups may be similar as illustrated in segments 87.1, 87.2 and 87.3 where the thicknesses t1, t2 and t3 are about the same. Similarly, segments 87.4, 87.5 and 87.6 illustrate segments of similar width or thickness where t4, t5 and t6 are about the same value. Similarly, segments 87.8, 87.9 and 87.10 illustrate segments of similar width or thickness where t8, t9 and t10 are about the same value.

FIG. 33 also illustrates how segments within a group or groups of segments may have a variety of different spacing (s1=s6) to provide enhancements to a filter for improving medical imaging modality characteristics. For example, in the segment grouping of 87.1, 87.2 and 87.3, there is a spacing s1 between segment 87.1 and segment 87.2 but then no spacing between segments 87.2 and 87.3. A spacing s2 is shown between segment 87.3 but then no spacing in the combination segment grouping formed by segments 87.4, 87.5 and 87.6. A spacing of s3 is shown between the three segment combination of 87.4, 87.5 and 87.6 to the single segment 87.7. The single segment 87.7 is spaced apart by spacing s4 from the equally sized (i.e., t8=t9=t10) and equally spaced (i.e., s5=s6) group of segments 87.8, 87.9 and 87.10. It is to be appreciated that in various alternative embodiments, the spacing used in groups of segments or between groups of segments may be the same or variable.

FIG. 34 is a view of an exemplary filter illustrating various alternative aspects of providing a filter with improved echogenic characteristics. The filter illustrated is a conical filter. It is to be appreciated that the filter of FIG. 34 is merely representative of one type of filter. It is to be appreciated that the various alternative enhancement, modifications and treatments described herein may be provided to any intravascular or intraluminal filter. The exemplary filter is dividing into three general sections A, B and C. Sections A, B and C may be the same type of enhancement or have an enhancement different from one another section. In addition, the type of enhancement in each section may be the same or different from one another in detection, response or appearance under ultrasound. In addition, a tag, feature or enhancement may be different within a section. Circles 3402 are used to indicate exemplary locations for an echogenic feature, tag, marker or modification to an enhanced filter 10. The illustrative embodiment in FIG. 34 also illustrates a continuous echogenic layer, feature or modification or treatment 3408. The illustrative embodiment in FIG. 34 also illustrates an echogenic attribute on/near an inflection point 3406 in an enhanced filter structure 10. The illustrative embodiment in FIG. 34 also illustrates a segmented echogenic layer, feature or modification or treatment 3404 on an enhanced filter structure 10. Section A is considered the apex, tip, distal portion or terminal end depending upon filter configuration. Section B is considered the mid-strut, middle, filtration portion, debris capture portion, or thrombus collection or lysing portion depending upon specific filter configuration. Section C is considered the rear portion, proximal portion, proximal terminal portion, anchor, fixation or perforation portion depending upon a specific filter configuration. It is to be appreciated as well that the echogenic features, tags, markers or modifications illustrated for sections A, B and/or C may be of the same type or different types depending upon the echogenic signature or attribute intended for that section, group or sections or filter. As such, the echogenic features, tags, markers or modifications for a particular section may be selected from any of the various alternatives described herein.

Echogenic characteristics may be added to each of the sections based on the type of function being measured or characterized. For example, echogenic markers, features or tags may be added to Section A in order to provide, for example: identification of the terminal end, end portion or retrieval portion of a filter. Echogenic characteristics of Section A may also be used for determinations related to Section A specifically or the filter generally of filter position, positioning, attitude within the lumen, localization of the filter within the vasculature and other traits common to the characterization of intravascular devices. For example, echogenic markers, features or tags may be added to Section B in order to provide, for example: identification of the mid strut portion, middle or capture region. Echogenic characteristics of Section B may also be used for determinations related to Section B such as for sizing, centering, symmetry of implantation, placement, apposition of implant to vessel walls, clot burden, deployment status or completion, gauge of filter capacity and/or filter contents as well as filter position, positioning, attitude within the lumen, localization of the filter within the vasculature and other traits common to the characterization of intravascular devices. For example, echogenic markers, features or tags may be added to Section C in order to provide, for example: identification of the rear portion, terminal end, retrieval feature, anchor location or depth of insertion, perforation indication or other aspects of the rear or proximal portion of a filter. Echogenic characteristics of Section C may also be used for determinations related to Section C such as for sizing, centering, symmetry of implantation or placement of legs struts and the like, as well as for determination of wall apposition, anchor penetration or perforation. Still further, the markers or tags may be added to aid in determining or evaluating filter position, positioning, attitude within the lumen, localization of the filter within the vasculature and other traits common to the characterization of intravascular devices.

A filter having enhanced echogenic properties is illustrated in FIG. 34 as it appears when it is in operative position within the vasculature. In one specific aspect the filter is in use in a large blood vessel. One exemplary vessel is the vena cava. Still further, a modified filter may be employed in a different vein or even an artery. The filter is designated generally by reference numeral 10, and the wall of the blood vessel in which it is located is designated by reference numeral 12. The filter 10 includes an apical hub 14 of overall egg-shaped or tear drop configuration and which has a generally hemispherically shaped end portion 14*a*.

The filter 10 includes a plurality of elongated legs 16 which are of equal length and are identically configured to each other. The legs 16 are collectively arrayed in a conical geometric configuration so that the legs converge to the apical hub 14, and are symmetrically spaced about a central axis extending through the hub. Each of the legs is of equal diameter over its entire length and is made of a relatively resilient material, such as tempered stainless steel wire or the like. In addition to the echogenic attributes described herein, the legs may be coated with a polymeric, synthetic resin material having anti-thrombogenic properties. FIG. 34 illustrates an echogenic marker at the tip 14. Exemplary continuous echogenic layers, features or modifications are also illustrated along one or more legs of the filter. In addition, FIG. 34 illustrates the use of echogenic tags, features or markers at, along or near inflection points in a filter element or component. In addition, FIG. 34 illustrates to application of echogenic markers, tags or features near the fixation elements of the filter.

In still other alternative embodiments, there is provided a material capture structure having one or more echogenic enhancements alone or in combination with radiopaque enhancements. In one aspect, the filter structure used in a filter includes both echogenic and radio opaque enhancements.

An one aspect, the filter includes material capture structure in the IVC filter will be viewable under fluoroscopic and ultrasound imaging modalities, including appropriate echogenic characteristics to enhance the view of the status or condition of the material capture structure while using IVUS. Enabling the material capture structure to be viewed will allow the physician to appropriately center and verify placement of a filter.

In one aspect, the filter elements or structures are doped to incorporate one or more of echogenic or radio opaque materials or treatments. In one aspect, the membrane, filaments or strands or other structures used to form the filter structure or webbing of the filter includes a radiopaque material having high echogenic properties, such as tungsten or gold, but not limited to either.

In other embodiments, one or more membranes, filaments or portions of a filament within a material capture structure includes one or more non-metallic echogenic features, such as those described elsewhere in this specification. For example, a membrane or filament or portion thereof may include air pockets either added to the material or by the use of materials with entrained air or gas that are used. Another example may include a membrane with a plurality of holes. In one embodiment, an ePTFE suture has echogenic properties due to air content of the ePTFE material. In other aspects, a suture material or a filament or polymer strand may also include dimpled/roughened/matrix/sponge materials, additives, or modifications to provide or enhance the overall echogenic nature of the suture, filament, material or material capture structure, in whole or in part.

In one aspect, these additional materials may assist the physician in centering or placing a filter within a vessel. In another aspect, this improvement is used in conjunction with IVUS will enable the adequate viewing of the filter portion of the filter and will allow for co-registration of filter placement along with an accurate entry/removal of the catheter through the webbing of the filter.

The advantages of this inventive aspect of a filter include, for example and not limitation, filter placement, accurate representation of filter location, ease of introducing/retracting catheter, more viewable space for more accurate assessments, ability to co-register filter location with IVUS and/or ability to better place filter in desired location.

Still other aspects of the use of the innovative filter include, for example, deployment of filters, positioning of filters, sizing of filters, and estimated treatment lengths as well as suture and/or material capture structure visibility. In still other aspects of the use of the innovative filter include, for example, deployment of a vena cava filter, positioning of an IVC filter, sizing of an IVC filter, and estimated treatment lengths as well as enhanced suture visibility.

In one embodiment, there is an IVC filter delivery system with an enclosed IVC filter. This filter would have a mesh, suture, web or other material capture structure suited to the anticipated filter use. The mesh, suture, web or other material capture structure has one or more components that is doped with a highly radiopaque material for better visibility under fluoro and good echogenicity for better viewing under IVUS guidance. In still further alternative embodiments, the techniques described above may be applied to one or more material capture structure described in U.S. Patent Application Publication US 2008/0147111 entitled "Endoluminal Filter with Fixation" filed Jun. 4, 2008 as U.S. patent application Ser. No. 11/969,827, (the "'7111 publication") incorporated herein by reference in its entirety for all purposes. In one particular aspect, the filament/strand/suture 461 shown in FIG. 58 of the '7111 publication may be coated or doped as described above alone or in combination with the illustrated pharmacological coating 466.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto. Any feature described in any one embodiment described herein can be combined with any other feature of any of the other embodiment whether preferred or not.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A system for providing embolic protection, the system comprising:
 a guidewire having a proximal end, a distal end, and a first pressure sensor disposed between the proximal end and the distal end of the guidewire;
 a first sheath having a proximal end, a distal end, and a first sheath lumen, and a port between the proximal end and the distal end of the first sheath, wherein the port is in fluid communication with the first sheath lumen, the first sheath lumen configured to receive the guidewire;
 a first distal protection filter attached to a distal portion of the first sheath;
 a second sheath having a proximal end, a distal end and a second sheath lumen, the first sheath disposed within the second sheath lumen;
 a second distal protection filter attached to a distal portion of the second sheath; and
 an outer sheath disposed over both the first sheath and the second sheath,
 whereupon being in a pre-deployed configuration, the first pressure sensor is axially disposed proximally of the first distal protection filter and the second distal protection filter, and whereupon being in a deployed configuration, the first pressure sensor is axially disposed between the first distal protection filter and the second distal protection filter and axially aligned with the port.

2. The system of claim 1, wherein the first distal protection filter comprises a self-expanding frame with a slidable crossover point that defines a proximal loop and a distal loop, and a filter element attached to one of the proximal loop or distal loop of the self-expanding frame of the first distal protection filter, wherein the crossover point is proximate to the filter element, and wherein the second distal protection filter comprises a self-expanding frame with a slidable crossover point that defines a proximal loop and a distal loop, and a filter element attached to the proximal loop of the self-expanding frame of the second distal protection filter, wherein the crossover point is proximal to the filter element.

3. The system of claim 1, further comprising an intravascular ultrasound transducer disposed at the distal end of the outer sheath.

4. The system of claim 1, further comprising an intravascular ultrasound transducer disposed on an atraumatic tip, the atraumatic tip extending from the distal end of the first sheath.

5. The system of claim 1, further comprising one or more echogenic features disposed on each of the first distal protection filter and the second distal protection filter.

6. The system of claim 1, further comprising a second pressure sensor located on a distal portion of the outer sheath proximally of the second distal protection filter in the pre-deployed configuration.

7. The system of claim 6, further comprising a third pressure sensor located on first sheath distally of the first distal protection filter in the pre-deployed configuration.

8. The system of claim 6, further comprising a third pressure sensor located on the first sheath proximally of the first distal protection filter and proximate to the first distal protection filter, and a fourth pressure sensor located on the second sheath proximally of the second pressure sensor in the pre-deployed configuration.

9. The system of claim 6, further comprising a third pressure sensor located on the first sheath within the first distal protection filter, and a fourth pressure sensor located on the second sheath within the second distal protection filter in the pre-deployed configuration.

10. A system for providing embolic protection, the system comprising:
 a first elongate member having a proximal end and a distal end;
 a first distal protection filter attached to a distal portion of the first elongate member;
 a first sheath having a proximal end, a distal end and a lumen, the first sheath disposed over the first elongate member;
 a second distal protection filter attached to a distal portion of the first sheath;
 an outer sheath disposed over both the first elongate member and the first sheath, the distal portion of the outer sheath comprising a rapid exchange guidewire lumen; and
 a first pressure sensor disposed within the first elongate member, whereupon being in a pre-deployed configuration, the first pressure sensor is axially disposed proximally of the first distal protection filter and the second distal protection filter, and whereupon being in a deployed configuration, the first pressure sensor is axially disposed between the first distal protection filter and the second distal protection filter.

11. The system of claim 10, further comprising a guidewire disposed within the rapid exchange guidewire lumen, wherein the first pressure sensor is located of a guidewire.

12. The system of claim 11, wherein the guidewire further comprises a second pressure sensor located distally of the first pressure sensor and the first distal protection filter.

13. The system of claim 12, wherein the guidewire further comprises a third pressure sensor located between the first pressure sensor and the second pressure sensor.

14. The system of claim 10, further comprising an intravascular ultrasound transducer located on the outer sheath distally of the rapid exchange guidewire lumen.

15. A system for providing embolic protection, the system comprising:
 a guidewire having a proximal end and a distal end;
 a first sheath having a proximal end, a distal end and a lumen, the lumen configured to receive the guidewire;
 a first distal protection filter attached to a distal portion of the first sheath;
 a second sheath having a proximal end, a distal end and a lumen, the second sheath disposed over the first sheath, wherein the distal end of the second sheath is located proximally the first distal protection filter;
 a second distal protection filter attached to a distal portion of the second sheath;
 an outer sheath disposed over both the first sheath and the second sheath;
 an intravascular ultrasound transducer disposed at the distal end of the outer sheath: and
 a first pressure sensor, whereupon being in a pre-deployed configuration, the first pressure sensor is axially disposed proximally of the first distal protection filter and the second distal protection filter, and whereupon being in a deployed configuration, the first pressure sensor is axially disposed between the first distal protection filter and the second distal protection filter.

16. The system of claim 1, further comprising: an intravascular ultrasound transducer disposed on an atraumatic tip, the atraumatic tip extending from the distal end of the first sheath.

* * * * *